(12) United States Patent
Kim et al.

(10) Patent No.: US 10,517,925 B2
(45) Date of Patent: *Dec. 31, 2019

(54) COMPOSITION COMPRISING KAI1 POLYPEPTIDE OR GENE ENCODING THE SAME FOR INHIBITING ANGIOGENESIS, AND USE THEREOF

(71) Applicant: SEOUL NATIONAL UNIVERSITY R & DB FOUNDATION, Seoul (KR)

(72) Inventors: Hyo-Soo Kim, Seoul (KR); Jin Hur, Seoul (KR); Jae Il Choi, Seoul (KR)

(73) Assignee: SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/571,723

(22) PCT Filed: May 4, 2016

(86) PCT No.: PCT/KR2016/004701
§ 371 (c)(1),
(2) Date: Nov. 3, 2017

(87) PCT Pub. No.: WO2016/178511
PCT Pub. Date: Nov. 10, 2016

(65) Prior Publication Data
US 2018/0153961 A1     Jun. 7, 2018

(30) Foreign Application Priority Data

May 6, 2015   (KR) ........................ 10-2015-0063202

(51) Int. Cl.
| | | |
|---|---|---|
| *A61K 38/17* | (2006.01) | |
| *A61K 48/00* | (2006.01) | |
| *A61P 27/02* | (2006.01) | |
| *A61P 35/00* | (2006.01) | |
| *A61P 9/00* | (2006.01) | |
| *G01N 33/50* | (2006.01) | |
| *G01N 33/566* | (2006.01) | |
| *G01N 33/574* | (2006.01) | |

(52) U.S. Cl.
CPC .......... *A61K 38/1709* (2013.01); *A61K 38/17* (2013.01); *A61K 38/177* (2013.01); *A61P 9/00* (2018.01); *A61P 27/02* (2018.01); *A61P 35/00* (2018.01); *G01N 33/50* (2013.01); *G01N 33/5023* (2013.01); *G01N 33/566* (2013.01); *G01N 33/574* (2013.01)

(58) Field of Classification Search
CPC .. A61K 38/17; A61K 38/1709; A61K 38/177; A61K 48/00; A61P 27/02; A61P 35/00; A61P 9/00
USPC .......... 514/1.1, 9.3, 19.5, 19.6, 21.2
See application file for complete search history.

(56) References Cited

U.S. PATENT DOCUMENTS

| | | | | |
|---|---|---|---|---|
| 5,595,756 A | * | 1/1997 | Bally ................... | A61K 9/1272 264/4.1 |
| 2005/0250102 A1 | | 11/2005 | Dong et al. | |
| 2010/0169990 A1 | | 7/2010 | Clarke et al. | |
| 2017/0290882 A1 | * | 10/2017 | Andronova .......... | A61K 9/0019 |
| 2017/0360955 A1 | * | 12/2017 | Janssen ............. | A61K 47/6849 |

OTHER PUBLICATIONS

Hait WN, "Anticancer drug development: the grand challenges," Nature Reviews, 2010, 9: 253-254.*
Sporn et al, "Chemoprevention of cancer," Carcinogenesis, 2000, 21(3): 525-530.*
Auerbach et al, "Angiogenesis assays: Problems and pitfalls," Cancer and Metastasis Reviews, 2000, 19: 167-172.*
Gura T, "Systems for Identifying New Drugs Are Often Faulty," Science, 1997, 278: 1041-1042.*
Jain RK, "Barriers to Drug Delivery in Solid Tumors," Scientific American, 1994, 58-65.*
Neidle, Stephen. ed., Cancer Drug Design and Discovery, Elsevier/Academic Press, 2008, 427-431.*
Bandyopadhyay et al, "Interaction of KAI1 on tumor cells with DARC on vascular endothelium leads to metastasis suppression," Nature Medicine, 2006, 12(8): 933-938.*
Wei et al., 'CD82 restrains pathological angiogenesis by altering lipid raft clustering and CD44 trafficking in endothelial cells' Circulation, vol. 130, No. 17, pp. 1493-1504 (2014), pp. 1493-1494.
Park et al., 'KAI1 suppresses HIF-1α and VEGF expression by blocking CDCP1-enhanced Src activation in prostate cancer' BMC cancer, vol. 12, No. 81, pp. 1-14 (2012).
GenBank: AAH00726.1, CD82 molecule [*Homo sapiens*] (Jul. 15, 2006).
NCBI Reference Sequence: NP_031682.1, CD82 antigen [Mus musculus] (Mar. 27, 2013).

(Continued)

*Primary Examiner* — Julie Ha
(74) *Attorney, Agent, or Firm* — Vorys, Sater, Seymour & Pease LLP; Mih Suhn Koh

(57) ABSTRACT

Provided are a composition including a Kang AI 1 (KAI1) polypeptide or a gene encoding the same, for inhibiting angiogenesis, and a use thereof, and more specifically, a composition including a KAI1 polypeptide or a gene encoding the same, for inhibiting angiogenesis, and a pharmaceutical composition for preventing and treating cancer. Further, KAI1, which is expressed in a pericyte rather than in an endotheliocyte, can inhibit angiogenesis by functioning as a negative angiogenic regulator, and thus the subject matter can inhibit angiogenesis due to a known angiogenesis factor by various methods such as a method using a supernatant in a pericyte which forcefully increases KAI1 or in which KAI1 is forcefully increased, a method using a KAI1 protein, or a method for inhibiting a Src-Pkc pathway provoking the degradation of KAI1. Further, the subject matter can identify the severity of a cancer patient by identifying the expression of KAI1 in a pericyte.

5 Claims, 78 Drawing Sheets
Specification includes a Sequence Listing.

(56) References Cited

OTHER PUBLICATIONS

Tsai et al., 'Dissecting the Diverse Functions of the Metastasis Suppressor CD82/KAI1' FEBS lett., vol. 585(20), pp. 3166-3173 (2011; 2012 PMC available, pp. 1-16).
NCBI Reference Sequence: NP_001116423.1, Duffy antigen/chemokine receptor isoform a [*Homo sapiens*] (Jul. 1, 2013).
NCBI Reference Sequence: NP_034175.2, atypical chemokine receptor 1 [Mus musculus] (Dec. 15, 2015).
Iiizumi et al., "Interaction of Duffy antigen receptor for chemokines and KAI1: a critical step in metastasis suppression" Cancer Research, vol. 67, No. 4, pp. 1411-1414 (2007), See abstract and p. 1411.

\* cited by examiner

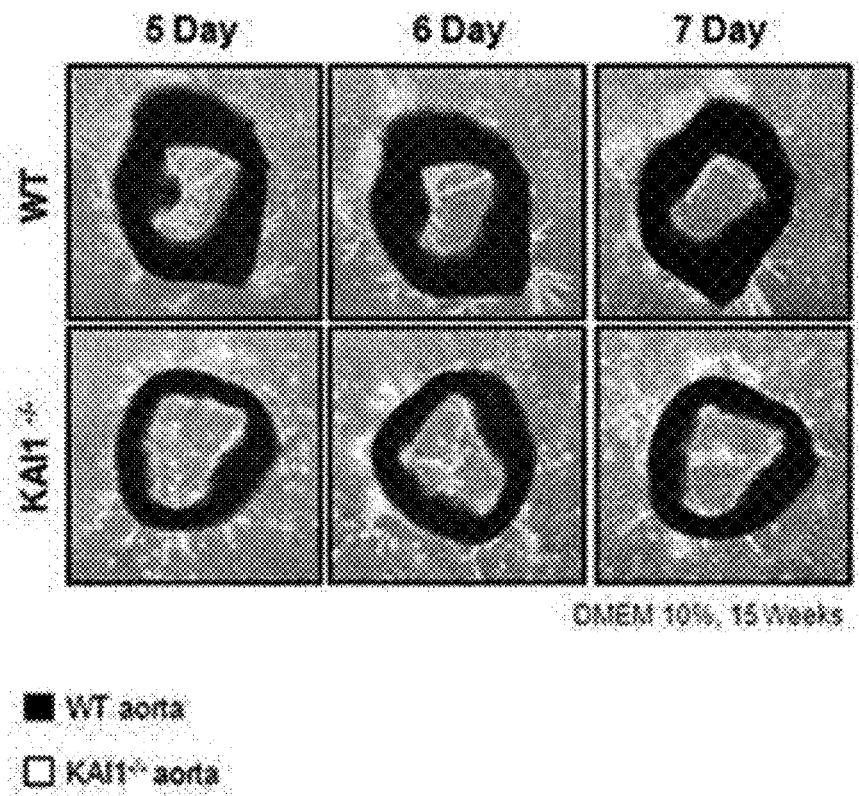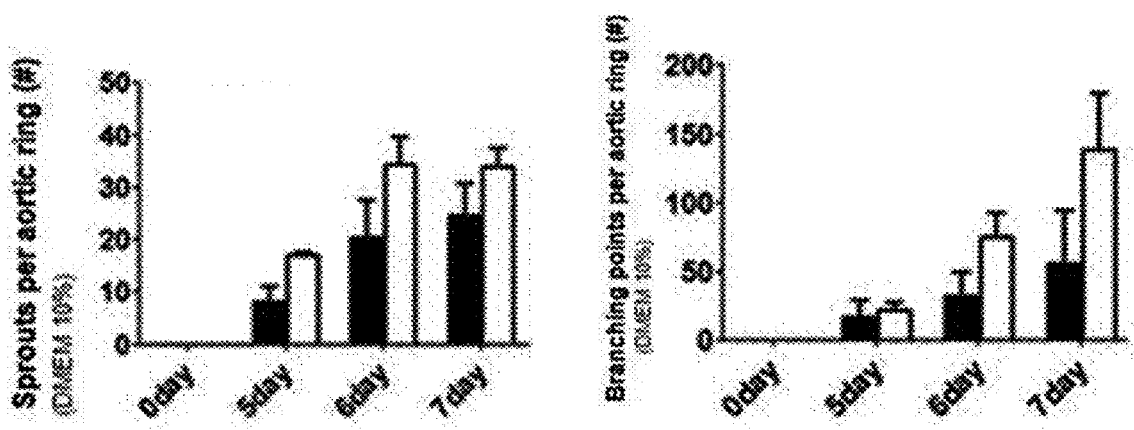
FIG. 8B

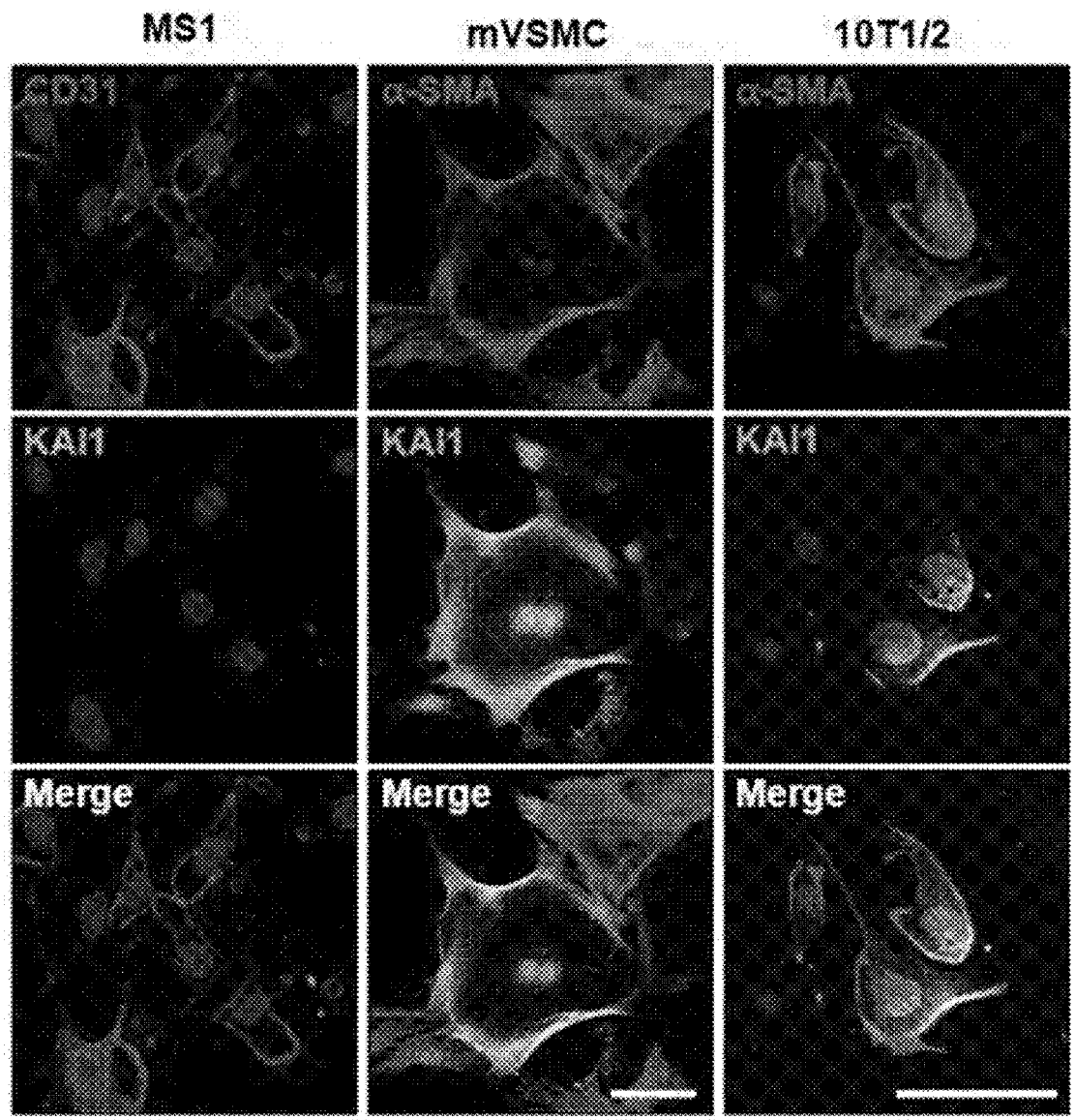

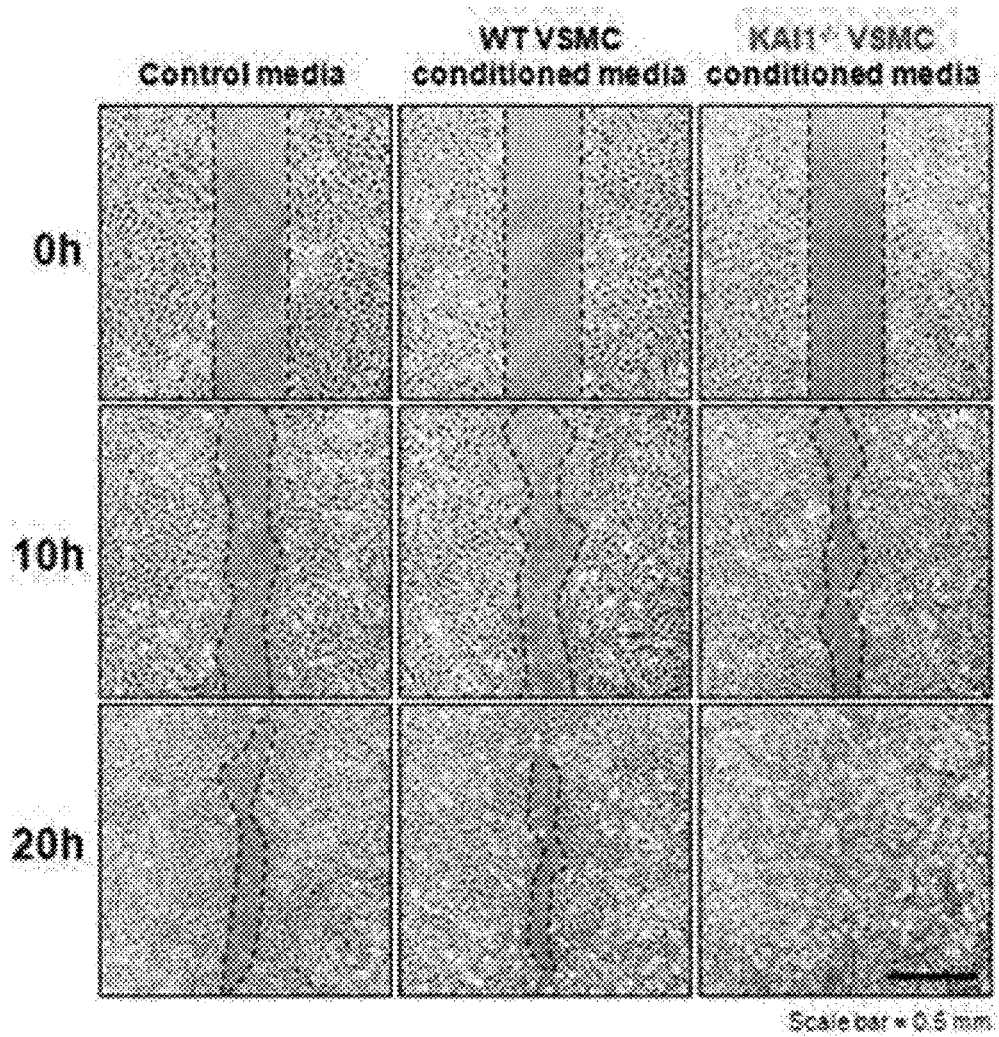

FIG. 24
10T1/2 [Mouse Pericyte] Supernatant
Adenovirus - Mock
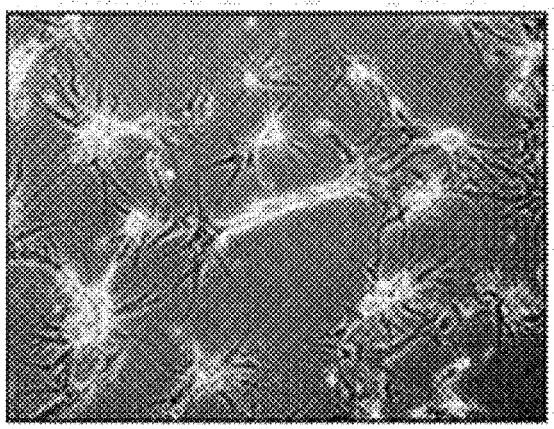
Adenovirus – KAI1
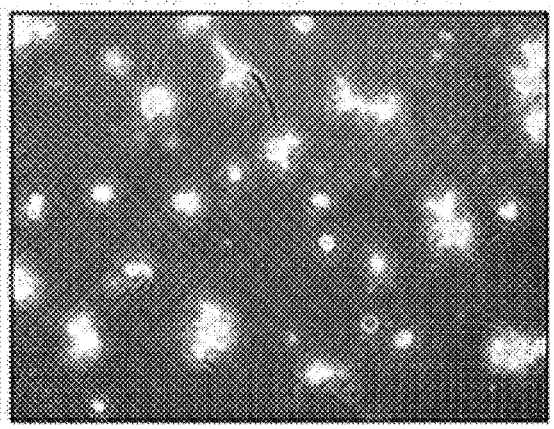
Adenovirus – KAI1
+ Goat IgG [Iso]
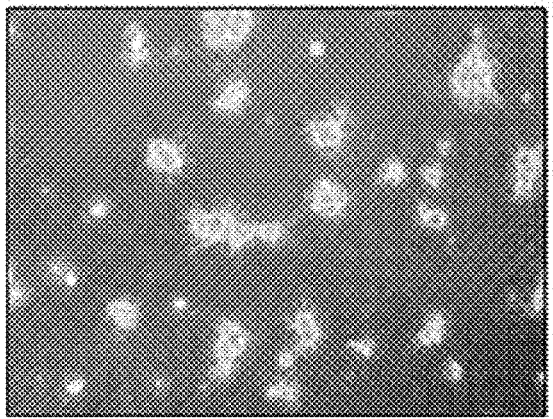
Adenovirus – KAI1
+ Anti-LIF [Neutral]
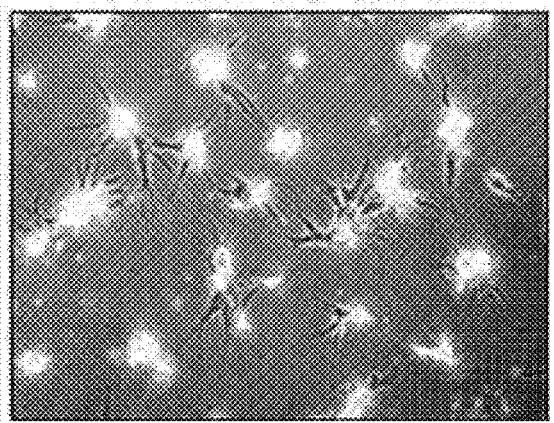

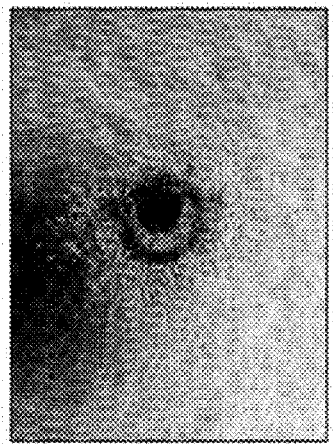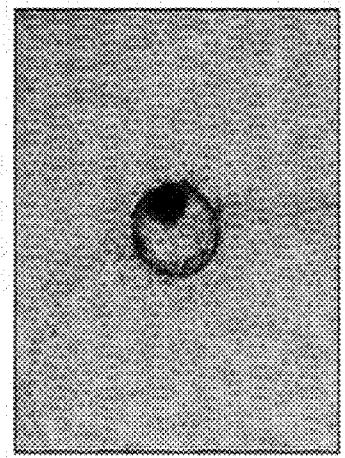
FIG. 45

FIG. 49
Human Colon tissue 1st
DAPI KAI1 SMA
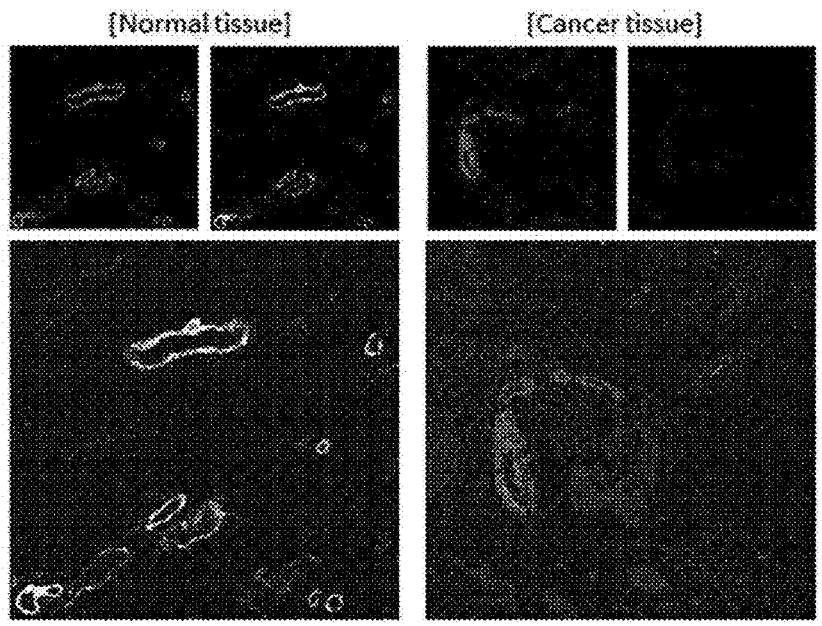
Human Prostate tissue 1st
DAPI KAI1 SMA
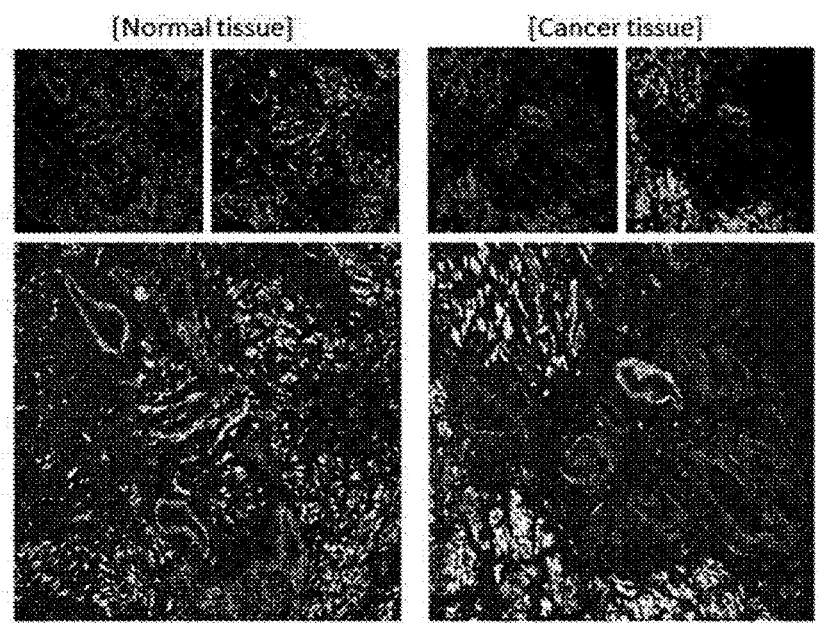

COMPOSITION COMPRISING KAI1 POLYPEPTIDE OR GENE ENCODING THE SAME FOR INHIBITING ANGIOGENESIS, AND USE THEREOF

STATEMENT REGARDING GOVERNMENT RIGHTS

The present invention was undertaken with the support of "Studying regulation mechanisms of retinal angiogenesis and developing an innovative therapy for wet age-related macular degeneration using membrane protein K" No. 1711069302 grant funded by the National Research Foundation of Korea (NRF).

CROSS-REFERENCE TO RELATED APPLICATION

This application claims priority to and the benefit of Korean Patent Application No. 10-2015-0063202 filed on May 6, 2015 and International Patent Application No. PCT/KR2016/004701, filed on May 4, 2016, the disclosure of which is incorporated herein by reference in its entirety.

SEQUENCE LISTING

The Sequence Listing submitted in text format (.txt) filed on Jun. 28, 2019, named "CorrectedSequenceListing.txt", created on Jun. 28, 2019 (21.3 KB), is incorporated herein by reference.

TECHNICAL FIELD

The present invention relates to a composition for inhibiting angiogenesis, which includes a KAI1 polypeptide or a gene encoding the same, and a use thereof, and more particularly to a pharmaceutical composition for inhibiting angiogenesis, which includes a KAI1 polypeptide or a gene encoding the same and a pharmaceutical composition for preventing or treating cancer.

BACKGROUND ART

Vasculogenesis or angiogenesis is the formation of new vessels, and is important in the embryo stage and also in adults. In the embryo stage, mesoderm-derived endothelial precursors (angioblasts) differentiate into endothelial cells, thereby forming a vessel. Angiogenesis also occurs in adults, and generally an angiogenic cytokine, particularly, a growth factor such as vascular endothelial growth factor (VEGF), directly acts on a reporter of vascular endothelial cells to promote angiogenesis. Particularly, VEGF-A of the VEGF family stimulates VEGFR2, which is a receptor thereof in a vascular endothelial cell, to provoke angiogenesis. Such an angiogenesis-stimulating cytokine may be secreted by blood cells or stromal cells.

Therefore, research has been conducted for developing an agent for treating a disease caused by angiogenesis by neutralizing a vessel-promoting factor or inhibiting a receptor thereof, and as a critical material for treating a disease caused by angiogenesis, an anti-VEGF agent has been used. For example, treatment agents targeting VEGF-A are critical in their use in cancers or retinal diseases, and particularly, Bevacizumab (trade name: Avastin) is an antibody of VEGF-A that has been proven to prevent recurrence and to extend of life in colon cancer and thus is expected to be effective on other types of cancer. However, an anti-VEGF agent reduces integrity of vessels and causes bleeding, and has side effects such as an increasing blood pressure (Elice F et al., Thrombosis Research (2012)).

For this reason, a substance capable of minimizing such side effects and inhibiting functions of various angiogenesis-stimulating factors while inhibiting VEGF has become a major subject for research, however the research that has been carried out and has still not produced sufficient results.

DISCLOSURE

Technical Problem

To solve the above-mentioned problems, the present invention is directed to providing a pharmaceutical composition for inhibiting angiogenesis, which includes a KAI1 polypeptide or a gene encoding the same, and a pharmaceutical composition for preventing or treating cancer.

The present invention is also directed to providing a method for screening an angiogenesis inhibitor or an agent for treating cancer, which includes the following steps:

(a) analyzing KAI1 expression after an isolated biological specimen is treated with a test material; and (b) determining the specimen as an angiogenesis inhibitor or an agent for treating cancer when the KAI1 expression of the specimen after treatment of the test material is greater than that of a biological specimen which is not treated with the test material.

The present invention is also directed to providing a method of screening an angiogenesis stimulant, which includes the following steps:

(a) analyzing KAI1 expression after an isolated biological specimen is treated with a test material; and (b) determining the specimen as an angiogenesis stimulant when the KAI1 expression of the specimen after treatment of the test material is decreased than that of a biological specimen which is not treated with the test material.

However, technical problems to be solved in the present invention are not limited to the above-described problems, and other problems which are not described herein will be fully understood by those of ordinary skill in the art from the following description.

Technical Solution

To achieve the objects of the present invention, the present invention provides a pharmaceutical composition for inhibiting angiogenesis, which includes a KAI1 polypeptide or a gene encoding the same.

The present invention provides a pharmaceutical composition for preventing or treating cancer or an ischemic disease, which includes a KAI1 polypeptide or a gene encoding the same.

In one exemplary embodiment of the present invention, the composition may further include a DARC polypeptide or a gene encoding the same.

In another exemplary embodiment of the present invention, the KAI1 polypeptide may consist of amino acids of SEQ ID NO: 1 or 2.

In still another exemplary embodiment of the present invention, the DARC polypeptide may consist of amino acids of SEQ ID NO: 3 or 4.

In yet another exemplary embodiment of the present invention, angiogenesis may be involved in tumor growth and metastasis, ischemic heart disease, Buerger's disease, age-related macular degeneration, rheumatoid arthritis, diabetic foot, diabetic retinopathy, psoriasis, central serous (chorio)retinopathy, chronic inflammation, vascular calcification, or critical limb ischemia.

In yet another exemplary embodiment of the present invention, the KAI1 polypeptide may be expressed in pericytes and thus inhibit angiogenesis.

In yet another exemplary embodiment of the present invention, the pericytes may improve organ transplantation or regeneration ability.

In yet another exemplary embodiment of the present invention, the cancer may be colon cancer, pancreatic cancer, colorectal cancer, prostate cancer, kidney cancer, melanoma, bone metastasis of prostate cancer, ovarian cancer, or blood cancer.

The present invention provides a method of screening for an angiogenesis inhibitor, which includes the following steps:

(a) analyzing KAI1 expression after an isolated biological specimen is treated with a test material; and (b) determining the specimen as an angiogenesis inhibitor when the KAI1 expression of the specimen after treatment of the test material is greater than that of a biological specimen which is not treated with the test material.

The present invention provides a method for screening an agent for treating cancer, which includes the following steps:

(a) analyzing KAI1 expression after an isolated biological specimen is treated with a test material; and (b) determining the specimen as an agent for treating cancer when the KAI1 expression of the specimen after treatment of the test material is greater than that of a biological specimen which is not treated with the test material.

The present invention provides a method for screening an angiogenesis stimulant, which includes the following steps:

(a) analyzing KAI1 expression after an isolated biological specimen is treated with a test material; and (b) determining the specimen as an angiogenesis stimulant when the KAI1 expression of the specimen after treatment of the test material is lesser than that of a biological specimen which is not treated with the test material.

The present invention provides a method for preventing or treating cancer or an ischemic disease, which includes administering a pharmaceutically acceptable amount of the pharmaceutical composition to a subject.

The present invention provides a method for inhibiting angiogenesis, which includes administering a pharmaceutically acceptable amount of the pharmaceutical composition to a subject.

The present invention provides a method for providing information to diagnose the severity of cancer, which includes confirming KAI1 expression of a pericyte in an isolated biological specimen.

The present invention provides a use of the pharmaceutical composition to prevent or treat cancer or an ischemic disease.

The present invention provides a use of the pharmaceutical composition to inhibit angiogenesis.

Advantageous Effects

According to the present invention, KAI1 expressed in pericytes rather than vascular endothelial cells can inhibit angiogenesis as a negative angiogenic regulator. Therefore, in the present invention, angiogenesis resulting from a conventionally known angiogenesis-stimulating factor can be inhibited using various techniques including a method for forcefully increasing KAI1 or using a supernatant from pericytes in which KAI1 is forcefully increased, a method for using a KAI1 protein, or a method for inhibiting Src and Pkc pathways to induce KAI1 degradation.

In addition, while having a different targeting mechanism from the conventional method, the KAI1 of the present invention can minimize side effects of a conventional therapy product by directly acting on vascular endothelial cells, and exhibit synergistic effects in combination with the conventional therapy product.

Moreover, the KAI1 of the present invention blocks functions of various growth factors as well as VEGF, and thus can be applied to a wide range of vessel-related diseases including one or two undefined retinal diseases or various types of cancer. In addition, the severity of a patient's cancer can be confirmed by identifying KAI1 expression of a pericyte.

DESCRIPTION OF DRAWINGS

FIGS. 7A and 7B and FIGS. 8A and 8B show the result of comparing aortic ring sprouting over time between KAI1$^{-/-}$ mice and WT under conditions of 5% DMEM (FIGS. 7A and 7B) and 10% DMEM (FIGS. 8A and 8B).

FIGS. 12A and 12B and FIG. 13 show the results of RT-PCR, Western blotting, and immunostaining to confirm KAI1 expression of a mouse EC line MS-1, a mouse primary vascular smooth muscle cell (mVSMC), and a mouse pericyte cell line 10T1/2.

FIGS. 17A and 17B shows the result of a scratch wound healing assay for MS-1 using culture media for culturing WT or KAI1$^{-/-}$ mVSMC (WT or KAI1$^{-/-}$ mVSMC conditioned media), to confirm whether the inhibition of angiogenic tendency of MS-1 by mVSMC is caused by a paracrine effect.

FIG. 24 shows the result of a tube formation assay performed on a matrigel to visualize an EC sprouting inhibitory effect by LIF.

FIGS. 45 and 46 show the result of confirming EC sprouting according to the experimental process of FIG. 44.

FIG. 49 shows confocal images of KAI1(488) and SMA (555) stained with an antibody to compare KAI1 expression patterns in vascular pericytes of normal tissue and tumor tissue.

MODES OF THE INVENTION

Figure 1:
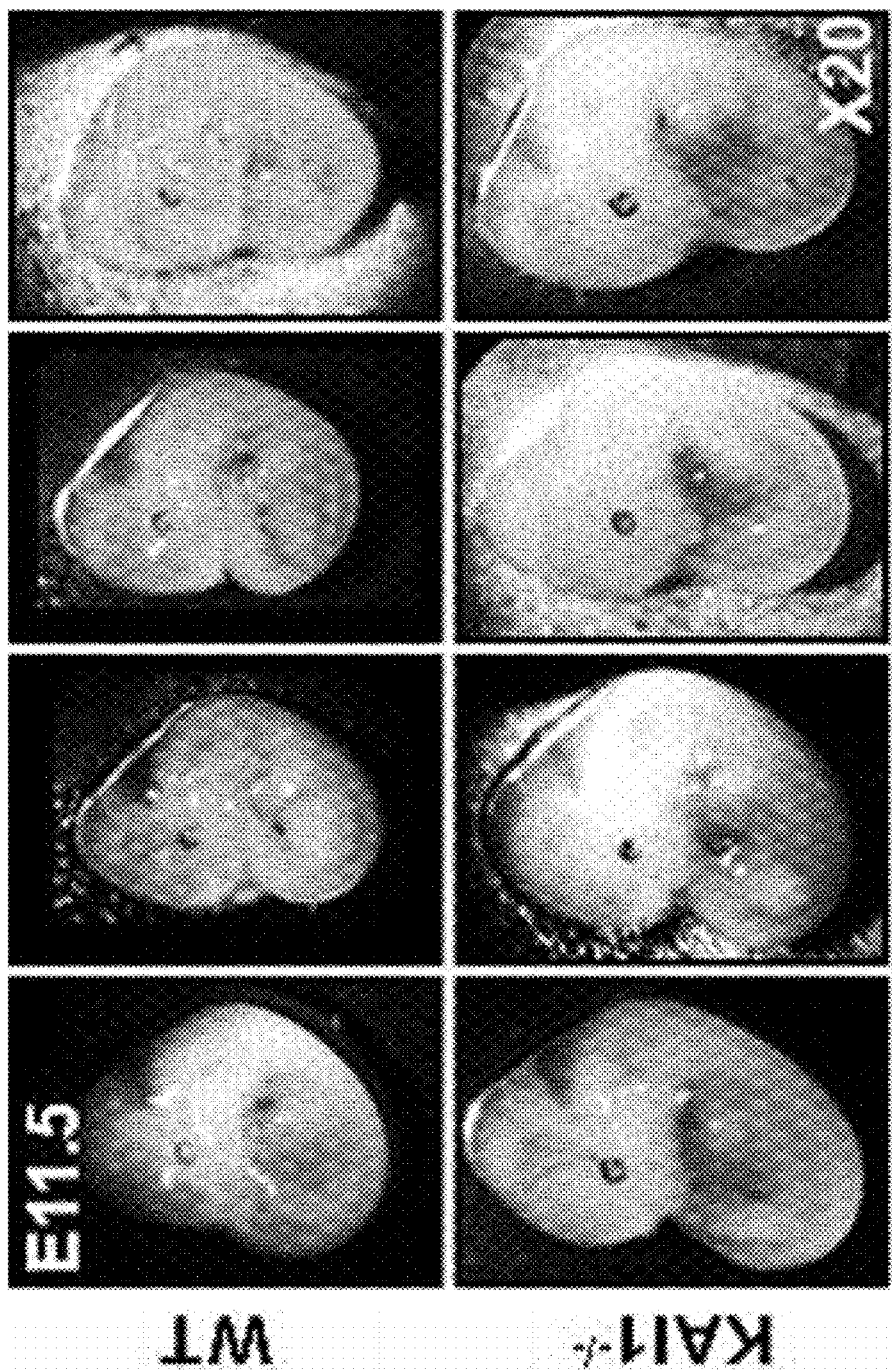
FIG. 1 shows comparison of development processes of WT and KAI1$^{-/-}$ mice in an embryonic stage.

According to research for a substance capable of regulating angiogenesis, the inventors confirmed that KAI1 was expressed in pericytes around epithelial cells (ECs) a maximum of tens of times higher than that expressed in ECs, and thus functions as a negative angiogenic regulator, and based on this the present invention was accomplished.

Hereinafter, the present invention will be described in detail.

The present invention provides a pharmaceutical composition for inhibiting angiogenesis, which includes a KAI1 polypeptide or a gene encoding the same.

The term "angiogenesis" used herein refers to the phenomenon in which new capillaries are formed by degradation of the extracellular matrix, the migration, division, and differentiation by ECs of existing vessels, which is distinguished from lymphangiogenesis. That is, the circulatory system of a mammal is divided into two large systems such as the blood vascular system and the lymphatic system. Angiogenesis is the phenomenon in which new vessels are grown from existing vessels in the blood vascular system as described above. However, lymphangiogenesis is the phenomenon in which new lymph vessels are formed in the lymphatic system, and is a very important process for maintenance of immune functions and inhibition of inflammation. The vessels and the lymph vessels have different markers and stimulating factors, and different phenotypes. The lymph vessels express prospero-related homeobox-1 (Prox1), which significantly affects lymphatic development, in a lymphatic epithelial cell differentiation stage unlike vessels. When VEGF-A significantly affects angiogenesis, VEGF-C significantly affects lymphangiogenesis. VEGF-C mainly acts on VEGFR3 of lymphatic epithelial cells. VEGF-D is also crucial in formation of lymph vessels, but does not necessarily affect lymph vessel development.

In the present invention, unlike a general angiogenesis mechanism, angiogenesis is inhibited by increasing KAI1 of a pericyte, not vascular endothelial cells, functioning as a target. In addition, such pericytes may improve organ transplantation or regeneration ability.

In the present invention, the KAI1(CD82) polypeptide may consist of a human-derived amino acid sequence of SEQ ID NO: 1 or a mouse-derived amino acid sequence of SEQ ID NO: 2, but the present invention is not limited thereto. The present invention may include a protein represented by an amino acid sequence having 70% or more, preferably 80% or more, more preferably 90% or more, and most preferably 95% or more homology with the above-mentioned amino acid sequence. In addition, in the present invention, the gene may be any gene capable of encoding a KAI1 polypeptide having the amino acid sequence of SEQ ID NO: 1 or 2.

In addition, the composition of the present invention may further include a DARC polypeptide or a gene encoding the same, and the DARC polypeptide may consist of a human-derived amino acid sequence of SEQ ID NO: 3 or a mouse-derived amino acid sequence of SEQ ID NO: 4, but the present invention is not limited thereto. The composition may include a protein represented by an amino acid sequence having 70% or more, preferably 80% or more, more preferably 90% or more, and most preferably 95% or more homology with the above-mentioned amino acid sequence.

In one exemplary embodiment of the present invention, it was confirmed that KAI1 is expressed in pericytes wrapping around the periphery of endothelial cells (ECs), not the endothelial cells themselves (refer to Example 2). In addition, it was confirmed that, in all of embryonic, postnatal and adult stages, angiogenesis was inhibited in a KAI1-expressed mouse group (refer to Example 1), angiogenic tendency was inhibited by KAI1 expression (refer to Examples 3 and 10), and KAI1 expression in pericytes was reduced in angiogenic conditions, which were accomplished via Src and Pkc signalings (refer to Example 8).

In another exemplary embodiment of the present invention, as a result of confirming a renal disease-treating effect of a KAI1-expressed pericyte, when a KAI1 protein was injected and comparing to a control, it was confirmed that angiogenesis was inhibited in the presence of VEGF (refer to Example 12). In addition, as a result of confirming an effect of a KAI1-expressed pericyte on inhibiting tumor growth, it was confirmed that tumor growth was considerably inhibited in a KAI1-expressed mouse group (refer to Example 11).

From such experimental results, it can be seen that KAI1 expressed in pericytes, not endothelial cells, functions as a negative angiogenic regulator, thereby inhibiting angiogenesis. In addition, it can be seen that KAI1 has an anticancer effect by inhibiting angiogenesis. Therefore, a substance for increasing KAI1 or KAI1 expression may be effective in angiogenesis inhibition and tumor treatment.

In the present invention, angiogenesis may be involved in tumor growth and metastasis, ischemic heart disease, Buerger's disease, age-related macular degeneration, rheumatoid arthritis, diabetic foot, diabetic retinopathy, psoriasis, central serous (chorio)retinopathy, chronic inflammation, vascular calcification, or critical limb ischemia, but the present invention is not limited thereto.

In another aspect of the present invention, the present invention may further include a pharmaceutical composition for preventing or treating cancer or an ischemic disease, which includes a KAI1 polypeptide or a gene encoding the same, and may further include a DARC polypeptide or a gene encoding the same.

The term "prevention" used herein refers to all actions of inhibiting cancer or an ischemic disease or delaying the onset thereof by administration of the pharmaceutical composition according to the present invention.

The term "treatment" used herein refers to all actions involved in alleviating or beneficially changing symptoms of cancer or an ischemic disease by administration of the pharmaceutical composition according to the present invention.

The "cancer," which is a disease to be ameliorated, prevented, or treated by the composition of the present invention, encompasses diseases caused by cells having an aggressive characteristic such that cells are divided and grown by ignoring a normal growth limit, an invasive characteristic such that cells are infiltrated into peripheral tissue, and a metastatic characteristic such that cells are spread to other parts of the body. In the present invention, examples of cancer may include colon cancer, pancreatic cancer, colorectal cancer, prostate cancer, kidney cancer, melanoma, bone metastasis of prostate cancer, ovarian cancer, and blood cancer, but the present invention is not limited thereto. In addition, the ischemic disease may be selected from the group consisting from myocardial damage, myocardial ischemia, primary cardiac arrest, angina pectoris, myocardial infarction, arrhythmia, cerebral infarction, diabetic foot ulcer, diabetic nephropathy, ischemic heart failure, ischemic renal failure, ischemic liver failure, and ischemic stroke, but the present invention is not limited thereto.

The pharmaceutical composition of the present invention may further include a pharmaceutically acceptable carrier. The pharmaceutically acceptable carrier may include saline, polyethyleneglycol, ethanol, vegetable oil, isopropylmyristate, etc., but the present invention is not limited thereto.

The composition of the present invention, which includes a KAI1 polypeptide or gene encoding the same as an active ingredient, may include the active ingredient at 0.0001 to 50 wt % with respect to the total weight.

A preferable dosage of the pharmaceutical composition of the present invention may be determined by one of ordinary skill in the art according to a condition and body weight of an individual, severity of a disease, a drug form, an administration route, and duration. However, the pharmaceutical composition of the present invention is preferably administered at 0.001 to 100 mg/kg, and more preferably 0.01 to 30 mg/kg a day. The pharmaceutical composition of the present invention may be administered once or several times a day.

The pharmaceutical composition of the present invention may be administered to mammals such as rats, mice, livestock, or humans via various routes. All methods of administration may be expected, and the pharmaceutical composition of the present invention may be administered, for example, orally, or by rectal, intravenous, intramuscular, subcutaneous, epidural, or intracerebroventricular injection.

The pharmaceutical composition of the present invention may be prepared in various pharmaceutical forms, and thus there is no limit to a drug form.

In a still another aspect of the present invention, the present invention provides a method for preventing or treating cancer or an ischemic disease by administering a pharmaceutically effective amount of the pharmaceutical composition into a subject. The term "subject" refers to a target to be treated, and more specifically, a mammal such as a human, or a non-human primate, a mouse, a rat, a dog, a cat, a horse, and a cow. In addition, it is apparent to those of ordinary skill in the art that the "pharmaceutically effective amount" used herein may be adjusted within various ranges according to a body weight, age, sex, or health condition of a patient a diet, the duration of administration, an administration route, an excretion rate, and the severity of a disease.

In addition, according to the present invention, KAI1, functioning as a negative angiogenic regulator, is expressed in pericytes rather than endothelial cells, and thereby angiogenesis is inhibited. A substance for increasing KAI1 expression is selected from unknown substances, thereby screening an angiogenesis inhibitor.

In yet another aspect of the present invention, the present invention provides a method for screening an angiogenesis inhibitor, which includes the following steps:
(a) analyzing KAI1 expression after an isolated biological specimen is treated with a test material; and
(b) determining the specimen as an angiogenesis inhibitor when the KAI1 expression of the specimen after treatment of the test material is greater than that of a biological specimen which is not treated with the test material.

Moreover, according to the present invention, when KAI1 is expressed, angiogenesis is inhibited, and thus tumor growth may be inhibited. A substance for increasing KAI1 expression is selected from unknown substances, thereby screening for an agent for treating cancer.

In yet another aspect of the present invention, the present invention provides a method for screening an agent for treating cancer, which includes the following steps:
(a) analyzing KAI1 expression after an isolated biological specimen is treated with a test material; and
(b) determining the specimen as an angiogenesis inhibitor when the KAI1 expression of the specimen after treatment of the test material is greater than that of a biological specimen which is not treated with the test material.

In addition, according to the present invention, an angiogenesis stimulant may be screened for by selecting a substance for decreasing KAI1 expression from unknown substances.

Therefore, as a yet another aspect of the present invention, the present invention provides a method for screening an angiogenesis stimulant, which includes the following steps:
(a) analyzing KAI1 expression after an isolated biological specimen is treated with a test material; and
(b) determining the specimen as an angiogenesis stimulant when the KAI1 expression of the specimen after treatment of the test material is lesser than that of a biological specimen which is not treated with the test material.

Hereinafter, to help in understanding the present invention, exemplary embodiments will be disclosed. However, the following examples are merely provided to more easily understand the present invention, and the scope of the present invention is not limited to the examples.

EXAMPLES

Example 1. Verification of KAI1 Functioning as Negative Angiogenic Regulator 1-1. Confirmation Through Mouse Growth Process To identify KAI1 as a negative angiogenic regulator, processes of growing a WT mouse (C57 mouse) and a KAI1$^{-/-}$ mouse were compared.

First, in an embryonic stage, genesis was compared between WT and KAI1$^{-/-}$ mice. More specifically, embryonic day 0.5 (E0.5) was determined at approximately 8 a.m on the day after mating mice, which was the day on which a mating plug was confirmed from a hen. An embryo was taken from a maternal body on the day of E11.5 and observed, and the result is shown in FIG. 1. As shown in FIG. 1, it can be confirmed that the overall size, and particularly, a head size, of KAI1$^{-/-}$ embryo (E11.5) was larger than that of a WT embryo. In addition, significant vessel formation and hemorrhaging in the heart was observed.

Figure 2A:
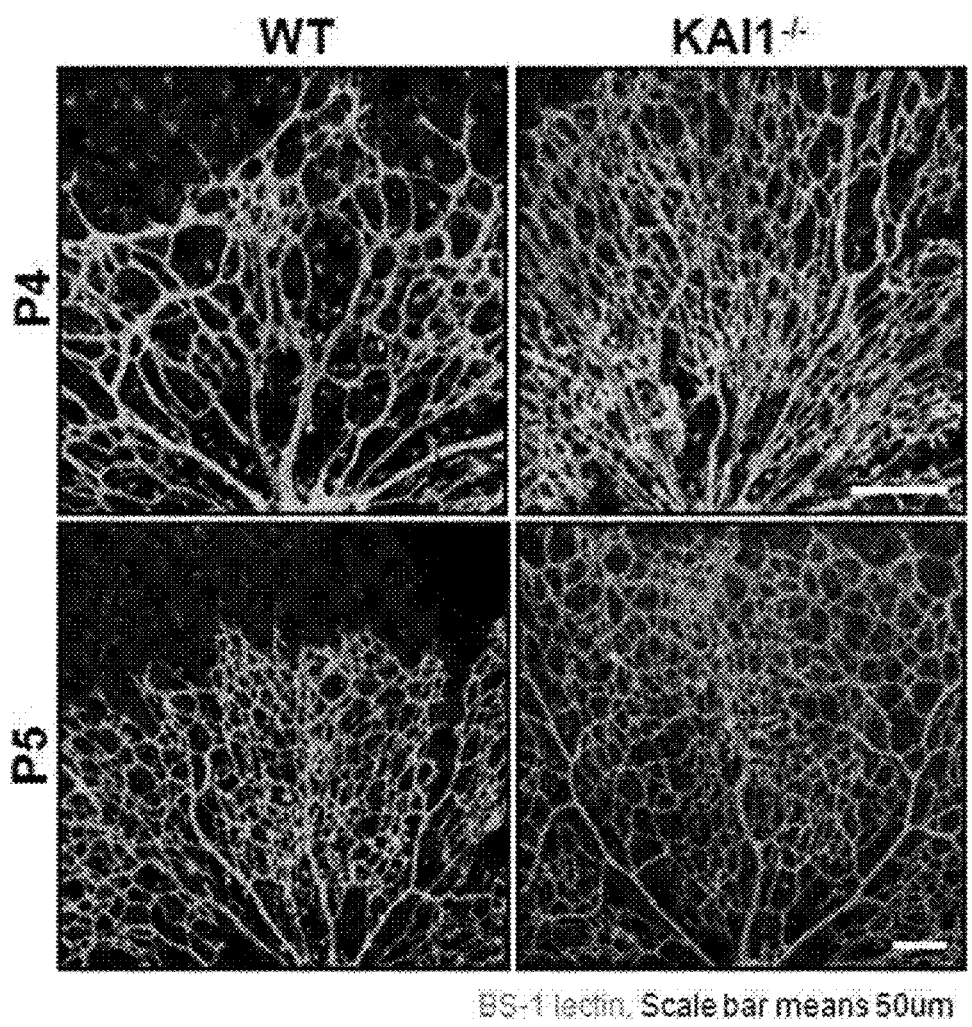
FIGS. 2A and 2B show the result of confirming retinal vessel development ability of KAI1$^{-/-}$ postnatal mice (P4 and P5) in a postnatal stage.
Figure 2B:
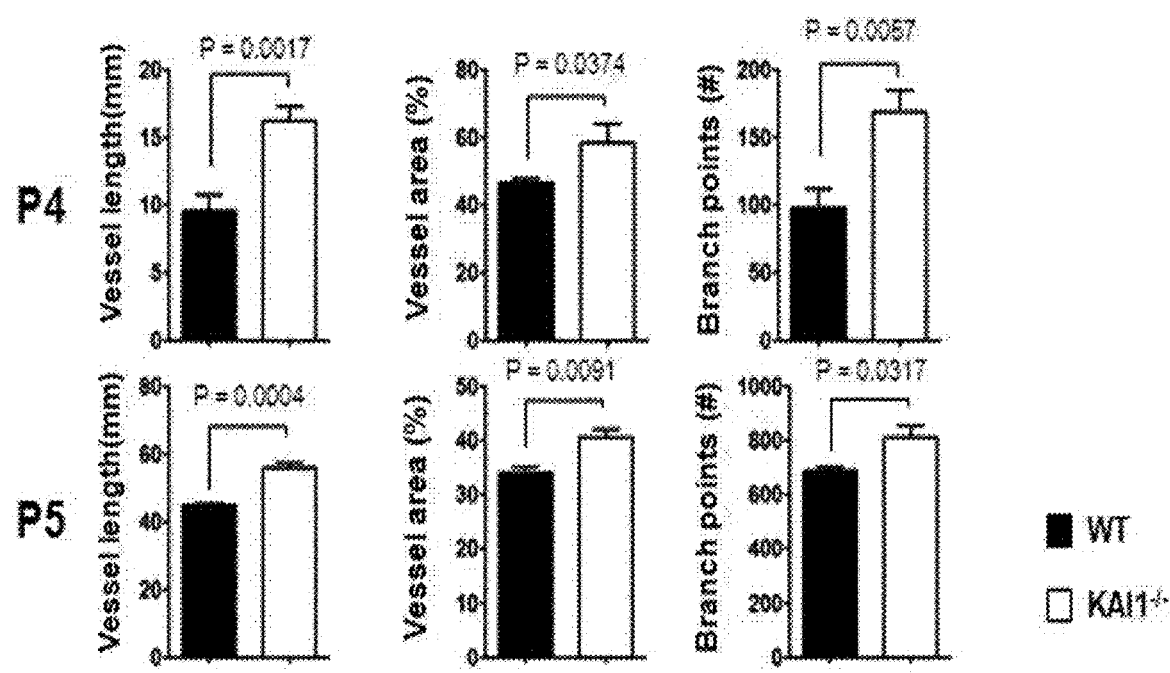

Then, in a postnatal stage, retinal vessel development ability of KAI1$^{-/-}$ postnatal mice (P4 and P5) was identified. More specifically, a mouse subject (P4 or P5) selected 4 to 5 days after birth was sacrificed to extract the retina, and then the retina was stained with BS-lectin and then observed. The result is shown in FIGS. 2A and 2B. As shown in FIGS. 2A and 2B, it can be confirmed that the retinal vessel development ability of KAI1$^{-/-}$ postnatal mice (P4 and P5) was higher than that of WT.

Figure 3A:
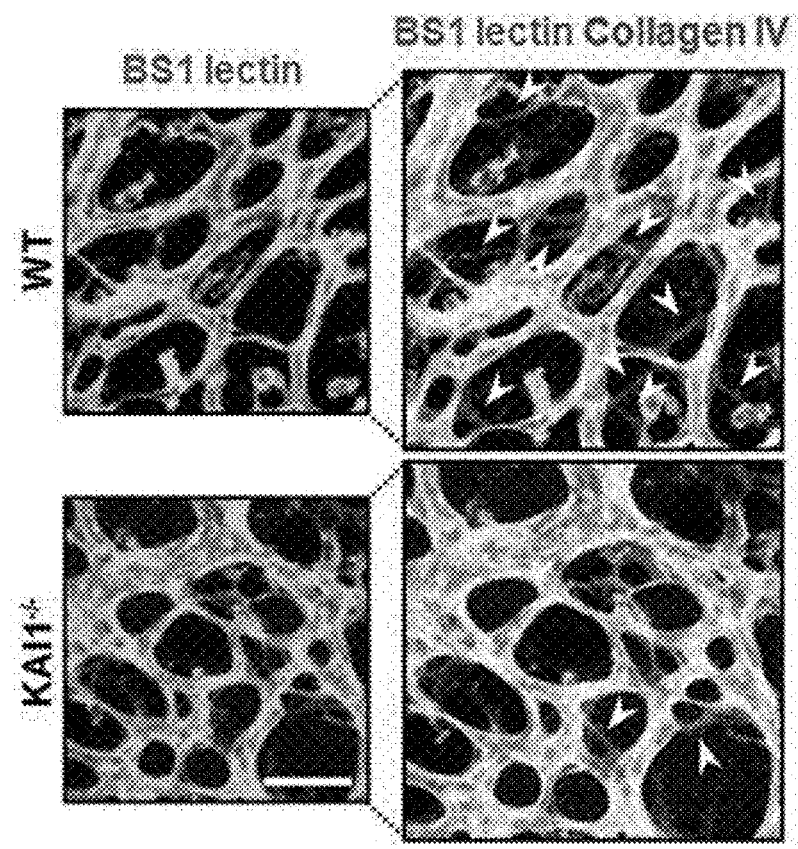
FIGS. 3A and 3B show the result of comparing vessel regression by identifying empty sleeves of the retinas of KAI1$^{-/-}$ postnatal mice (P5) and WT.
Figure 3B:
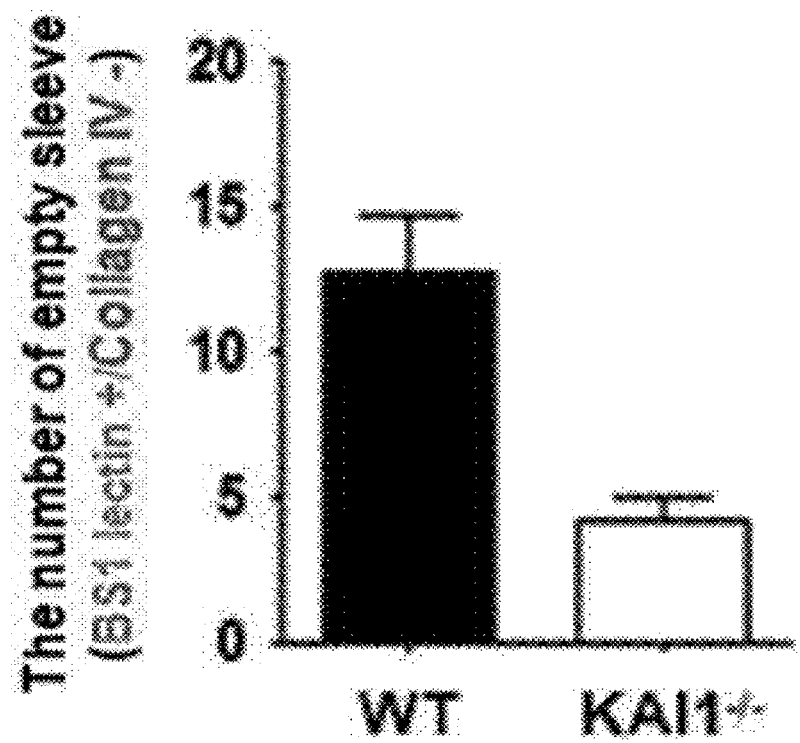
Figure 4A:
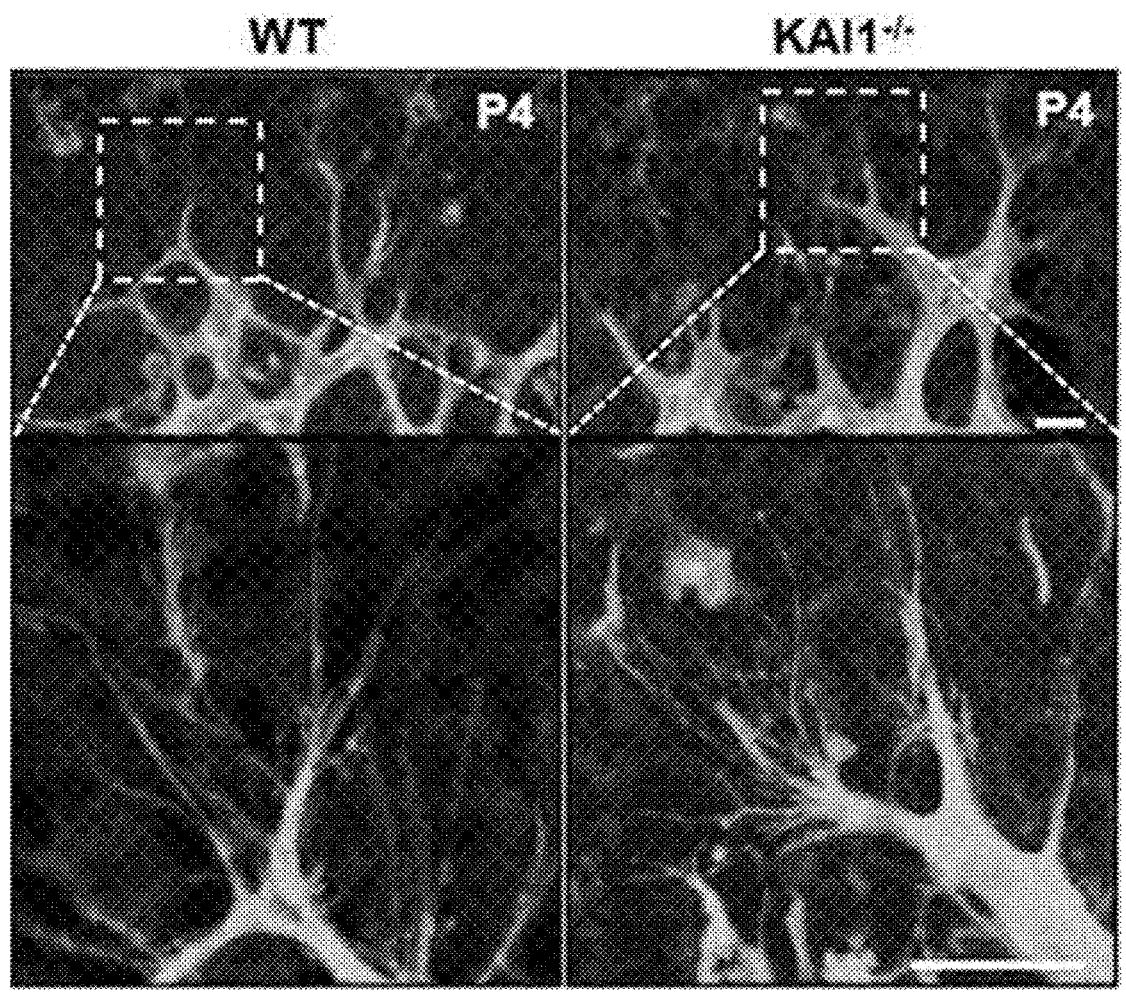
FIGS. 4A and 4B and FIGS. 5A and 5B show the result of comparing filopodia between KAI1$^{-/-}$ postnatal mice (P4) and WT.
Figure 4B:
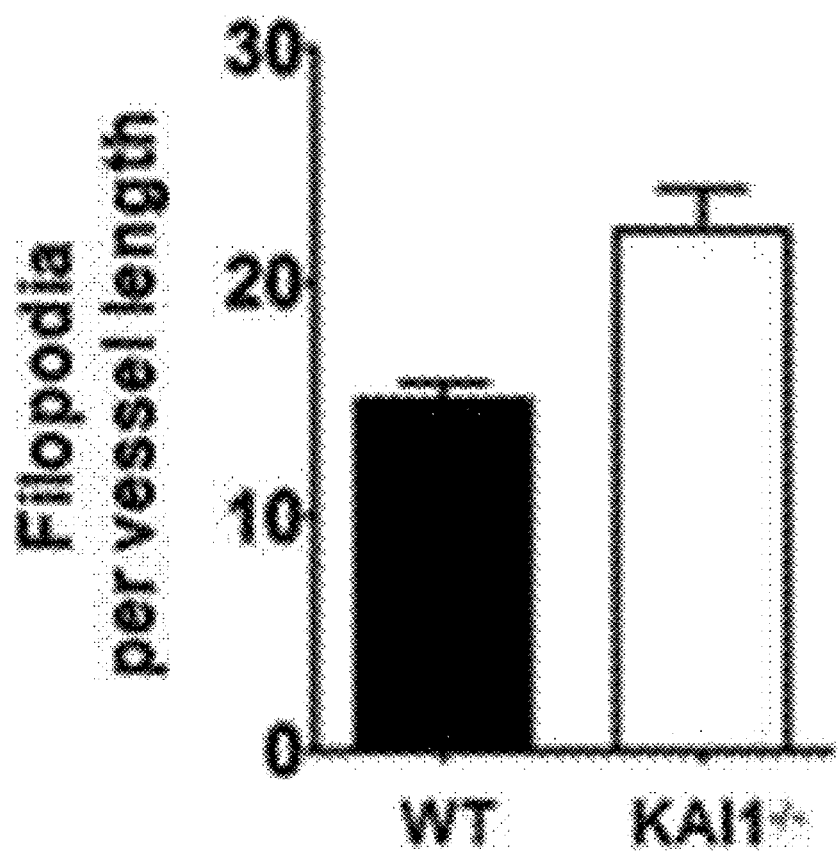
Figure 5A:
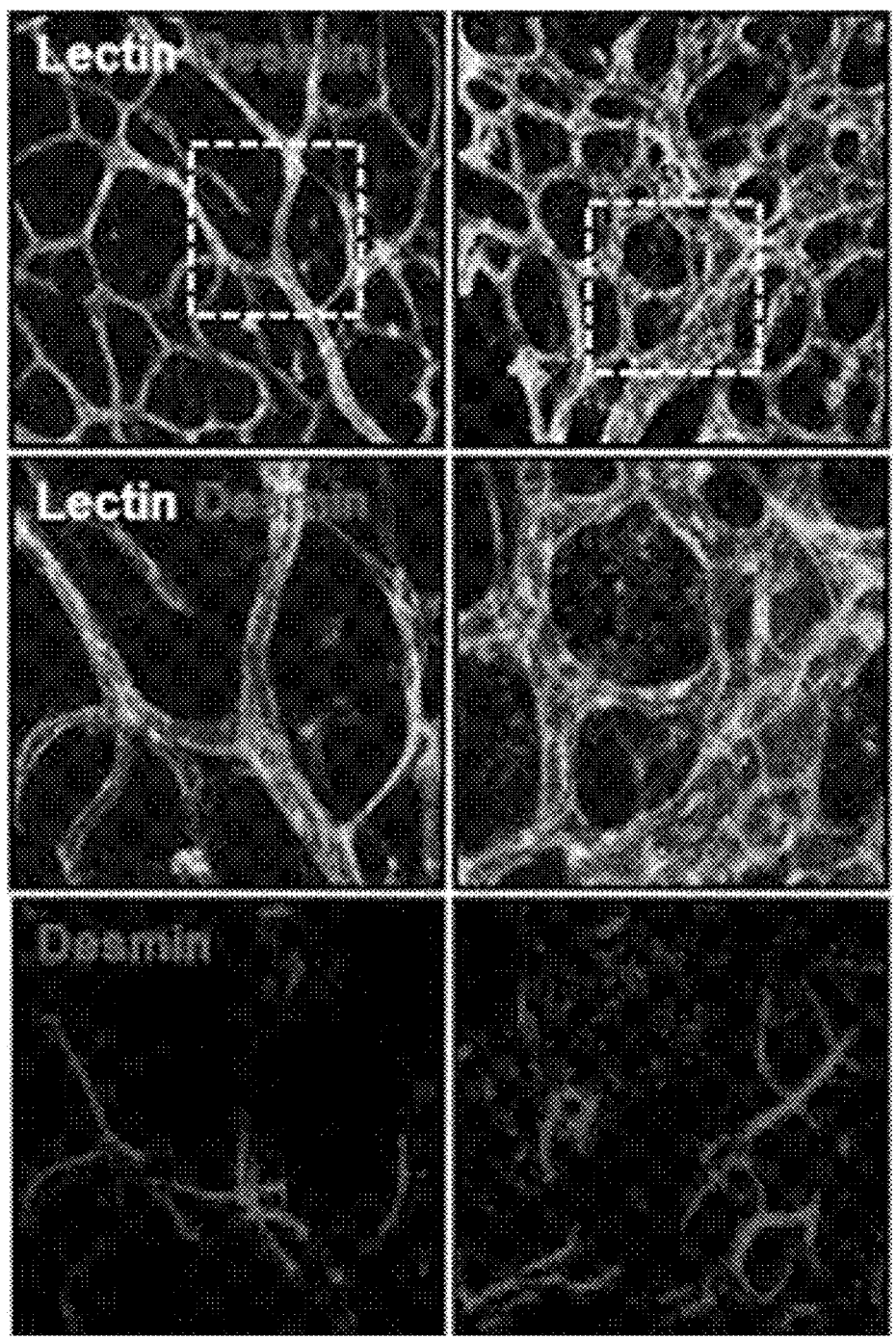
Figure 5B:
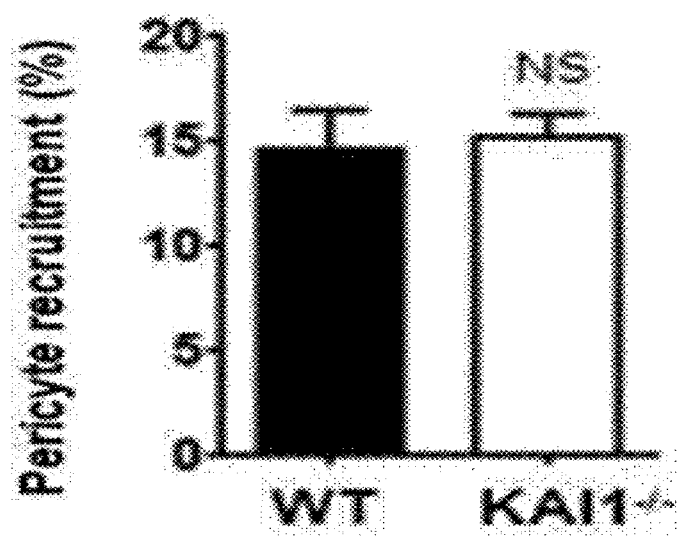

In addition, the retinas of the KAI1$^{-/-}$ postnatal mice (P5) and WT were stained with BS-1 lectin (green) and collagen IV (red) to identify empty sleeves (BS-1 lectin-/collagen IV+), thereby comparing vessel regression, and the result is shown in FIGS. 3A and 3B. As shown in FIGS. 3A and 3B, it was confirmed that the number of empty sleeves of the KAI1$^{-/-}$ postnatal (P5) mice was less than that of WT, and it can be seen from the result that there was less vessel regression in the KAI1$^{-/-}$ postnatal mice (P5) than in WT.

Additionally, the filopodia was compared between the KAI1$^{-/-}$ postnatal mice (P4) and WT. More specifically, a mouse subject (P4 or P5) selected 4 to 5 days after birth was sacrificed to extract the retina, and then the retina was stained with BS-lectin and then observed. The result is shown in FIGS. 4A and 4B and FIGS. 5A and 5B. As shown in FIGS. 4A and 4B and FIGS. 5A and 5B, it can be confirmed that the filopodia of the KAI1$^{-/-}$ postnatal mice (P4) was more well developed compared to those of WT, and it can be seen from the result that KAI1$^{-/-}$ postnatal retinal vessels were better able to be formed compared to WT.

Figure 6A:
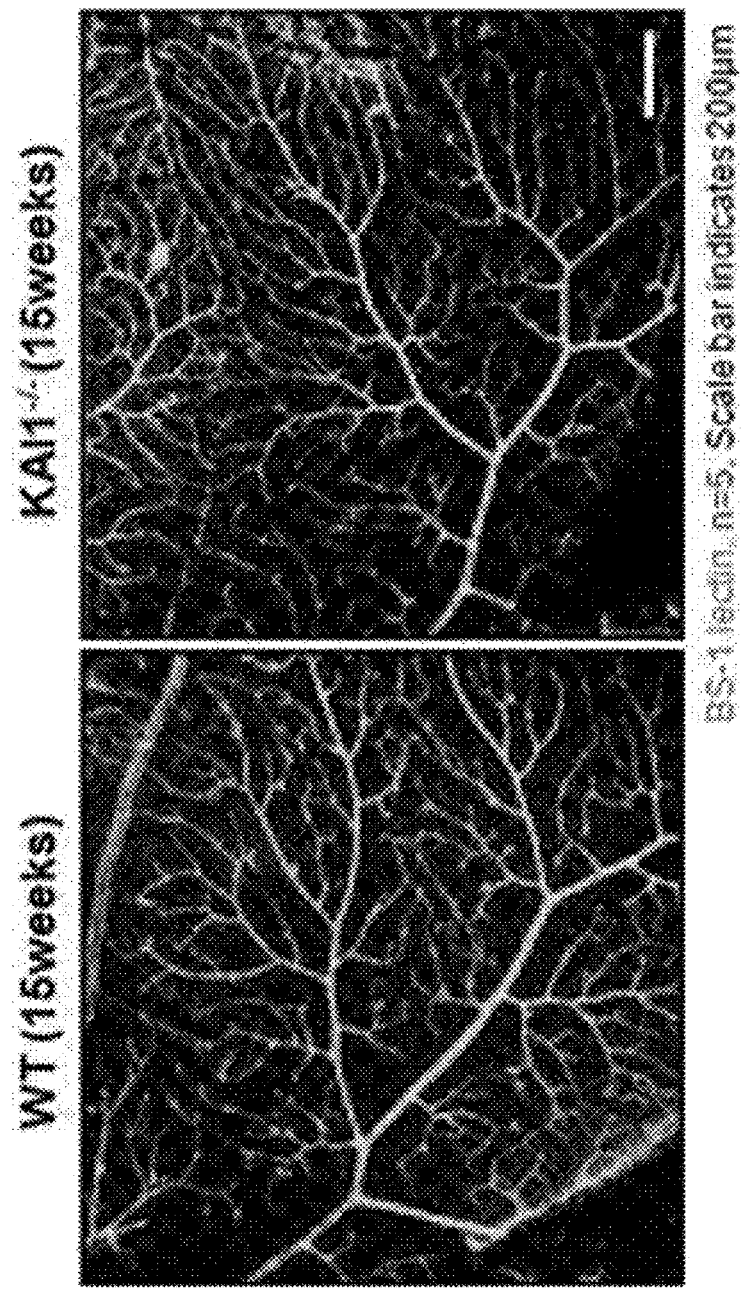
FIGS. 6A and 6B show the result of identifying adult retinal vessel networking in KAI1$^{-/-}$ mice and WT at an adult (15-week-old) stage.
Figure 6B:
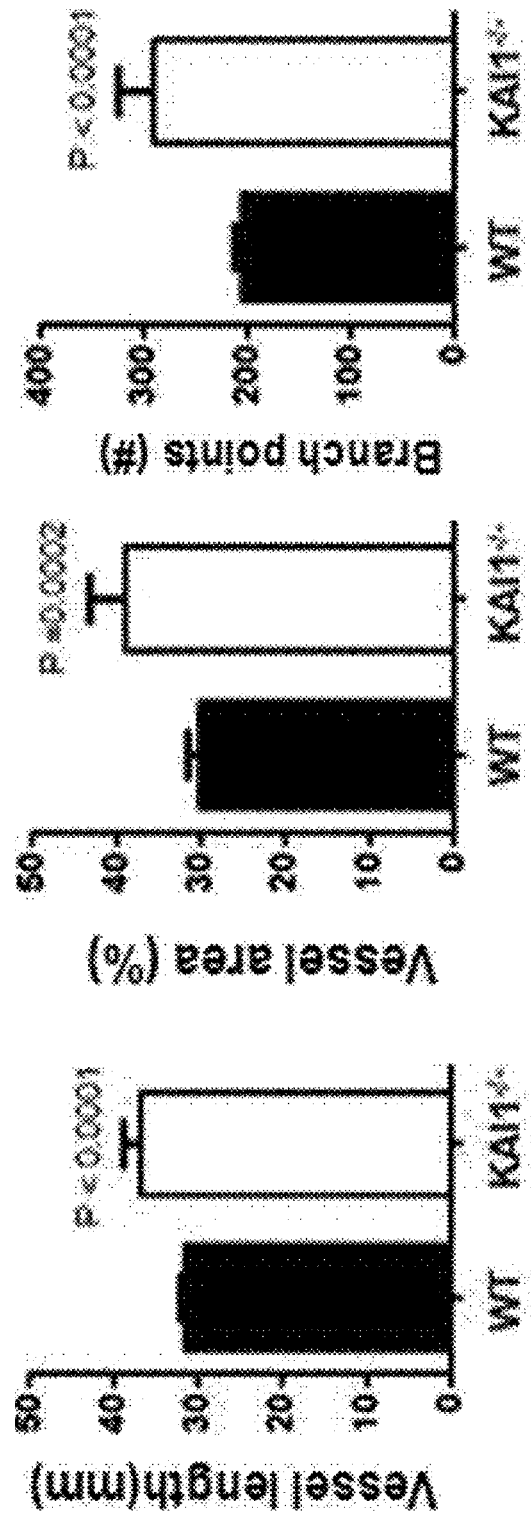
Figure 7A:
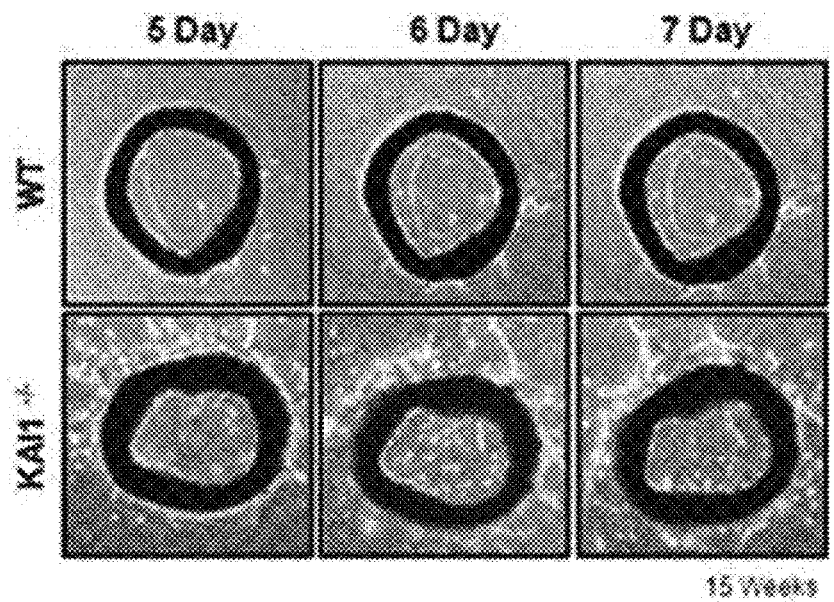
Figure 7B:
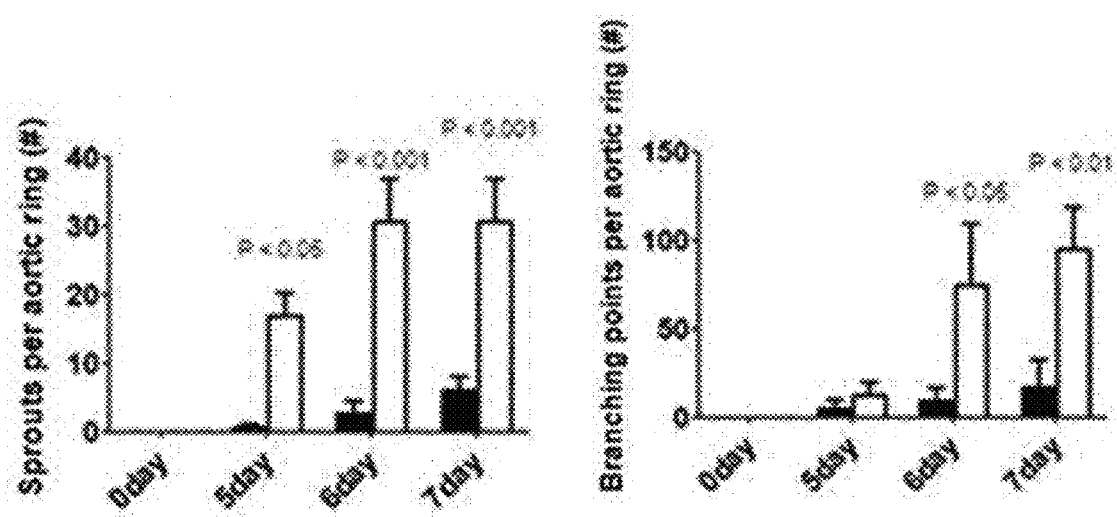
Figure 9A:
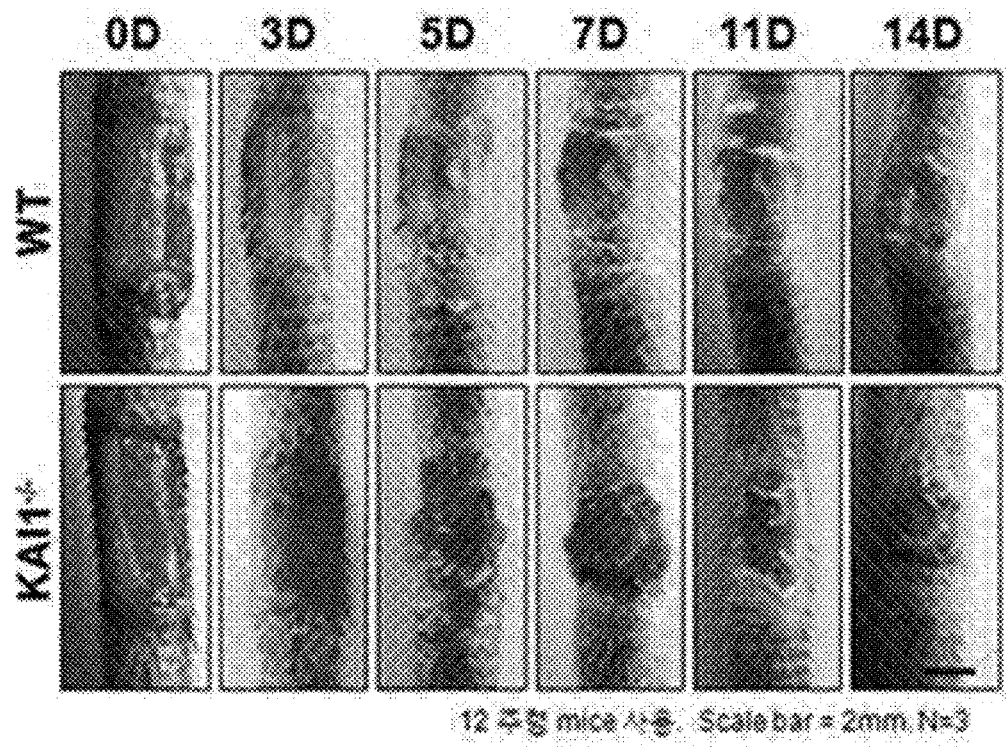
FIGS. 9A and 9B and FIGS. 10A and 10B show the result of comparing wound healing states of the tails of KAI1$^{-/-}$ mice and WT over time, indicating a wound healing rate (FIGS. 9A and 9B) and a degree of angiogenesis (FIGS. 10A and 10B).
Figure 9B:
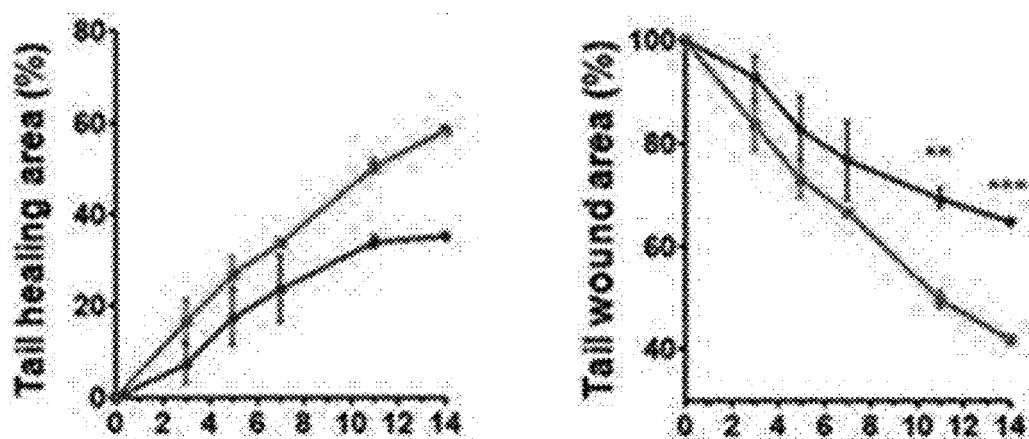
Figure 10A:
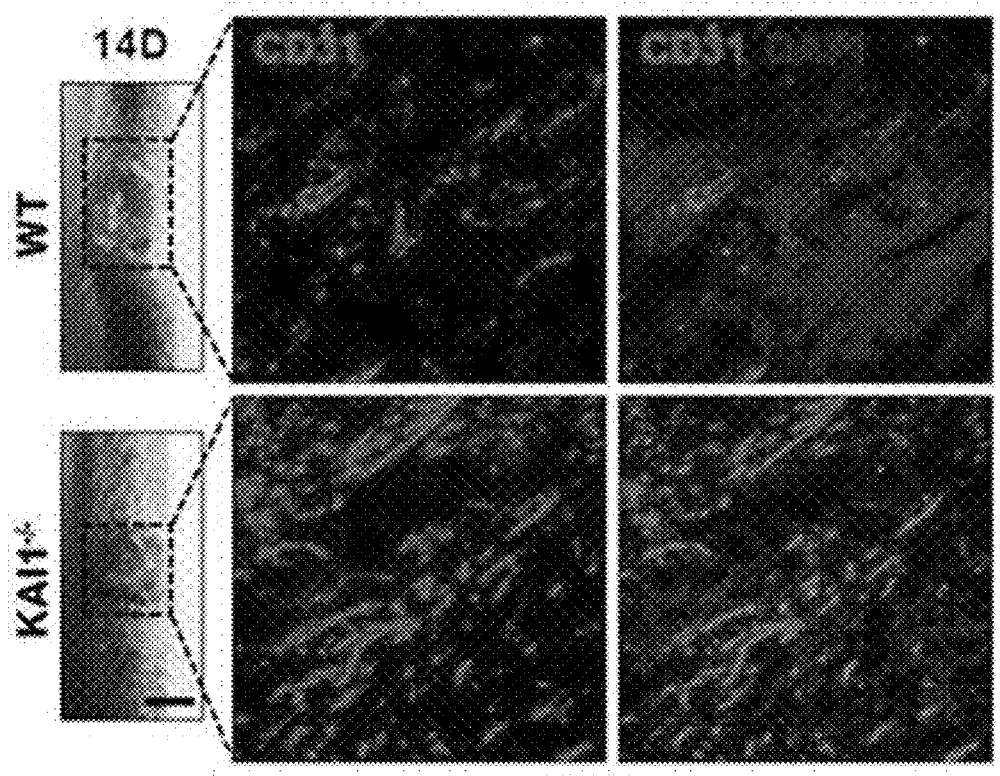
Figure 10B:
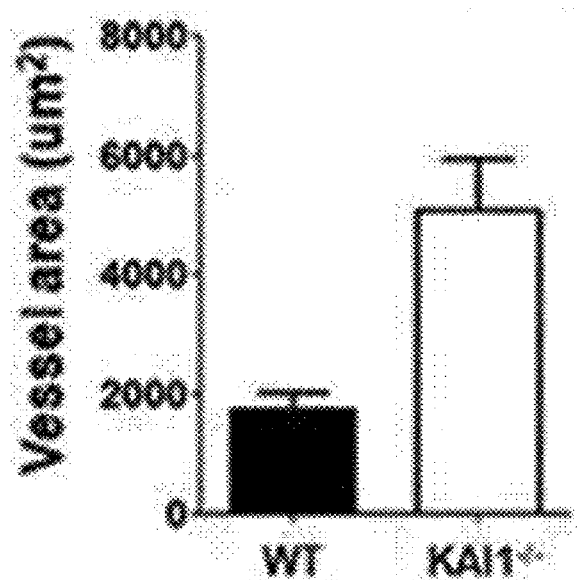

Subsequently, in an adult (15-week-old) stage, adult retinal vessel networking was identified in KAI1$^{-/-}$ mice and WT. More specifically, the retina of a 15-week-old adult mouse was stained with lectin, the length, area and branching point of the stained vessel were quantified, and the result is shown in FIGS. 6A and 6B. As shown in FIGS. 6A and 6B, it can be confirmed that the adult retinal vessel networking in the KAI1$^{-/-}$ mice was better than that in the WT mice, and it can be seen from the result that the formation of KAI1$^{-/-}$ adult retinal vessels in the KAI1$^{-/-}$ mice was greater than that of WT.

1-2. Confirmation Through Mouse Aortic Ring Assay

Aortic ring sprouting over time was compared between KAI1$^{-/-}$ mice and WT. More specifically, aortas of the mouse were seeded on a matrigel, and cultured in DMEM media under 5% and 10% FBS conditions to observe a degree of angiogenesis, and the result is shown in FIGS. 7A and 7B and FIGS. 8A and 8B. As shown in FIGS. 7A and 7B and FIGS. 8A and 8B, it can be confirmed that the aortic ring sprouted more rapidly in the KAI1$^{-/-}$ mouse than in WT in an in vitro angiogenic environment.

1-3. Confirmation Through Tail Wound Assay

Wound healing states of tails over time were compared between KAI1$^{-/-}$ mice and WT. More specifically, a wound was made to a size of 2 mm (width)×1 cm (length) in each of the tails of the WT and KAI1−/− mice and then a degree of wound healing was compared for 2 weeks, and the results are shown in FIGS. 9A and 9B and FIGS. 10A and 10B. As shown in FIGS. 9A and 9B and FIGS. 10A and 10B, it can be confirmed that in vivo tail wound healing occurred more rapidly in the KAI1$^{-/-}$ mouse than in WT, and a high degree of angiogenesis in the KAI1−/− mouse was also confirmed.

It can also be seen from the above results that when there was no KAI1 expression, angiogenesis was stimulated in vitro and in vivo.

Example 2. Identification of KAI1 Expression Subject

Figure 11:
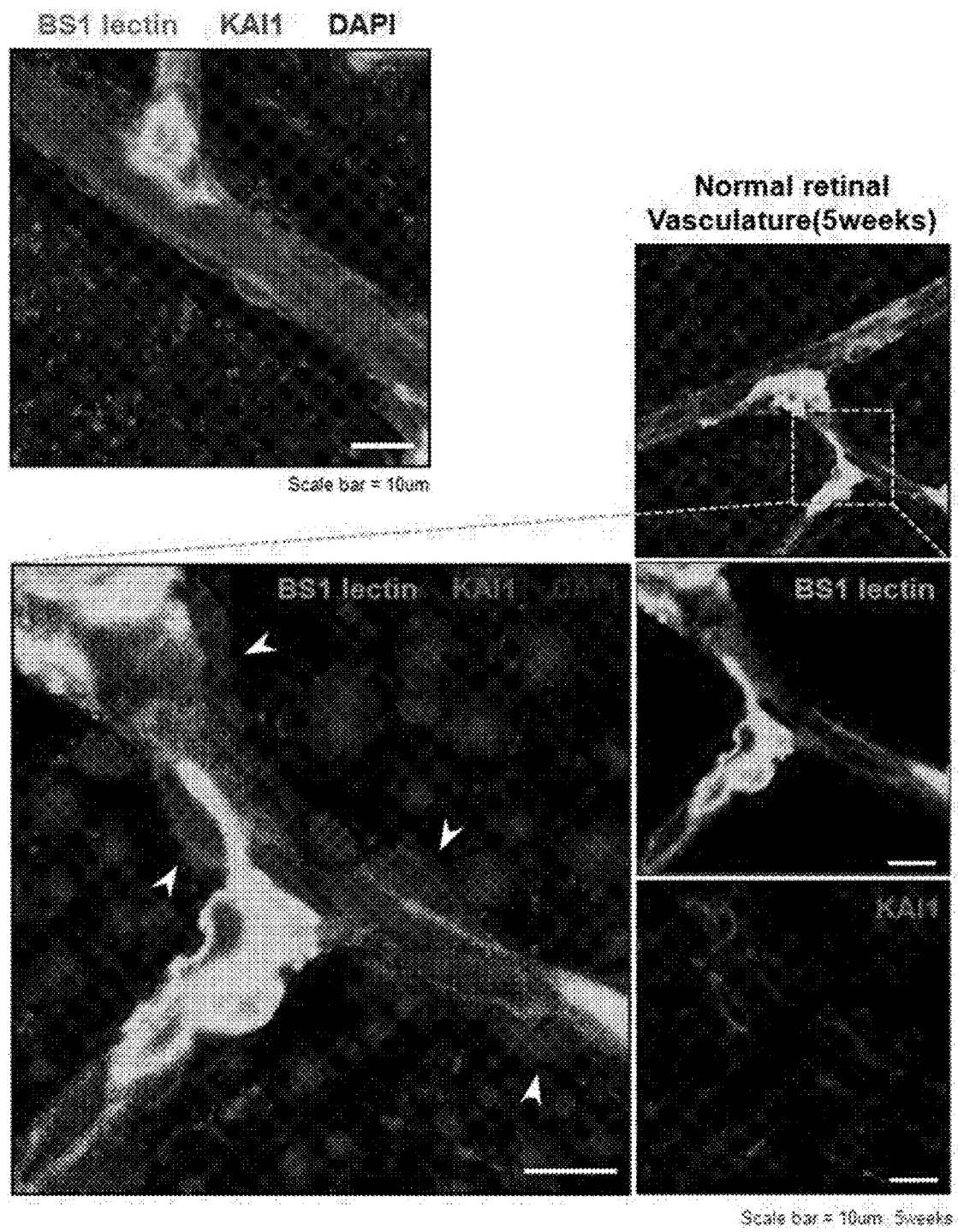
FIG. 11 shows the result of observing immunostaining on BS-1 Lectin, KAI1, and DAPI after fixing the retina of a C57 mouse with 4% PFA to identify a subject of KAI1 expression.

To identify a subject of KAI1 expression, the retina of a 5-week-old C57 mouse was fixed with 4% PFA and immunostained with BS-1 lectin (EC marker, using 488 nm wavelengths), KAI1 (using 555 nm wavelengths), and DAPI (nucleus, using UV) to obtain confocal images, and the result is shown in FIG. 11. As shown in FIG. 11, it can be confirmed that KAI1 was expressed in pericytes wrapping around ECs, rather than the ECs themselves.

In addition, KAI1 expressions in a mouse EC line MS-1, a mouse primary vascular smooth muscle cells (mVSMCs), and a mouse pericyte cell line 10T1/2 were identified using RT-PCR, Western blotting, and immunostaining. More specifically, RNA for RT-PCR was obtained using TRIzol (Invitrogen) according to a protocol provided by the manufacturer, and the RNA was used again to synthesize cDNA using a Primescript 1st strand cDNA synthesis kit (Takara). Afterwards, RT-PCR was performed using primers listed in Table 1 below, and an expression level of each gene was determined by electrophoresis. Here, glyceraldehyde-3-phosphate dehydrogenase (GAPDH), widely known as a housekeeping gene, was used as an endogenous control indicating that the total amount of cDNA to be analyzed was the same per cell line. For Western blotting, proteins were obtained using a cell lysis buffer (Cell Signaling) according to the guideline provided by the manufacturer. Afterwards, protein concentrations were measured through a BCA assay to isolate the same amount of protein per cell line through SDS-PAGE, and KAI1 expression levels were compared through an antibody reaction. Beta actin, also known as a housekeeping molecule, was used as an endogenous control indicating the total amount of protein to be analyzed was the same per cell line. Meanwhile, as a positive control for the KAI1 expression in RT-PCR and Western blotting, mouse brain tissue was used.

TABLE 1

| Type | | Primer sequence |
|---|---|---|
| KAI1 | FW(Forward) | 5'-CAGCCACTACAACTGGACAGAG-3' (SEQ ID NO: 5) |
| | RV(Reverse) | 5'-TACTTGGGGACCTTGCTGTAGT-3' (SEQ ID NO: 6) |
| αSMA | FW(Forward) | 5'-CTGACAGAGGCACCACTGAA-3' (SEQ ID NO: 7) |
| | RV(Reverse) | 5'-ATCTCACGCTCGGCAGTAGTA-3' (SEQ ID NO: 8) |
| Desmin | FW(Forward) | 5'-TGCAGCCACTCTAGCTCGTA-3' (SEQ ID NO: 9) |
| | RV(Reverse) | 5'-CTCATCAGGGAGTCGTTGGT-3' (SEQ ID NO: 10) |
| CD31 | FW(Forward) | 5'-GAATGACACCCAAGCGTTTT-3' (SEQ ID NO: 11) |
| | RV(Reverse) | 5'-GGCTTCCACACTAGGCTCAG-3' (SEQ ID NO: 12) |
| VE-CAD | FW(Forward) | 5'-ATTGAGACAGACCCCAAACG-3' (SEQ ID NO: 13) |
| | RV(Reverse) | 5'-ATTCGGAAGAATTGGCCTCT-3' (SEQ ID NO: 14) |
| GAPDH | FW(Forward) | 5'-CCCTTCATTGACCTCAACTACAT-3' (SEQ ID NO: 15) |
| | RV(Reverse) | 5'-CATTGCTGACAATCTTGAGTGAG-3' (SEQ ID NO: 16) |

Figure 12A:
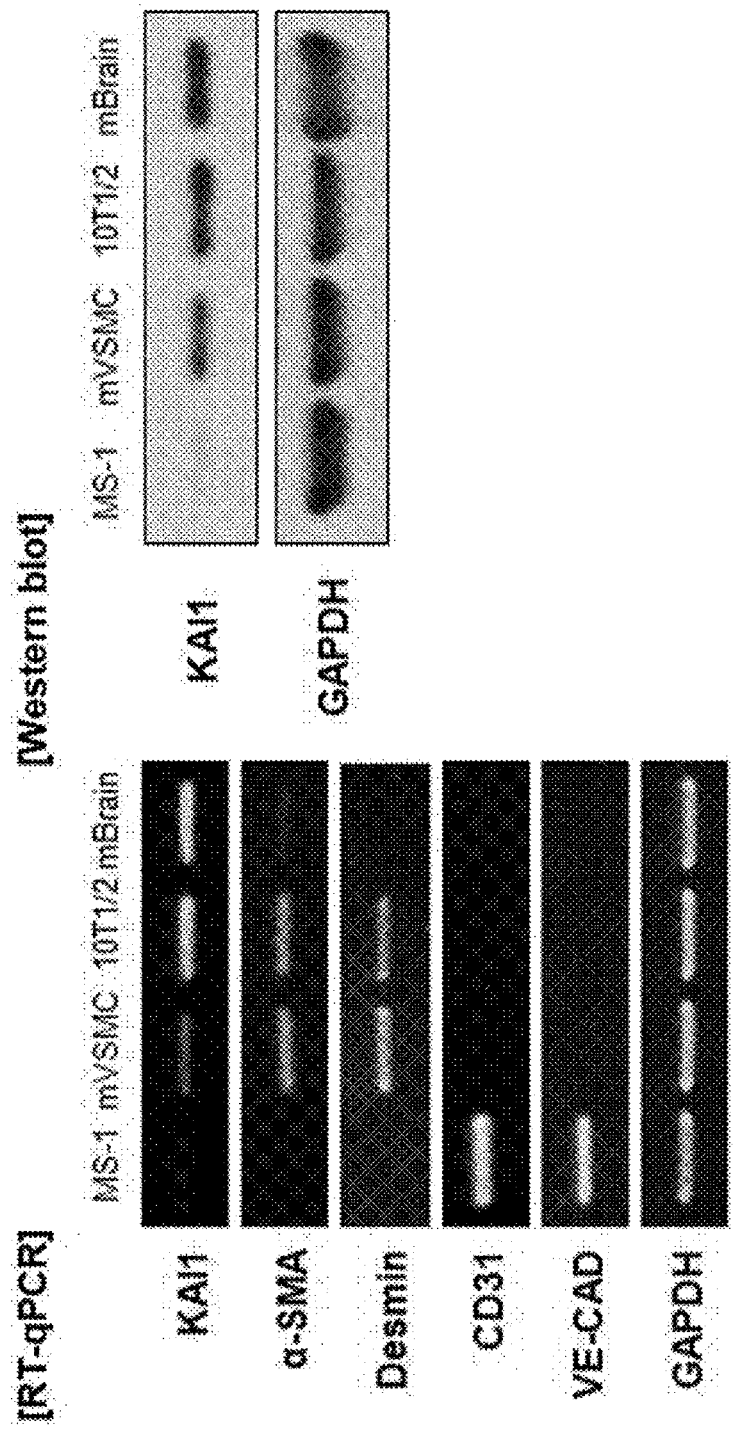
Figure 12B:
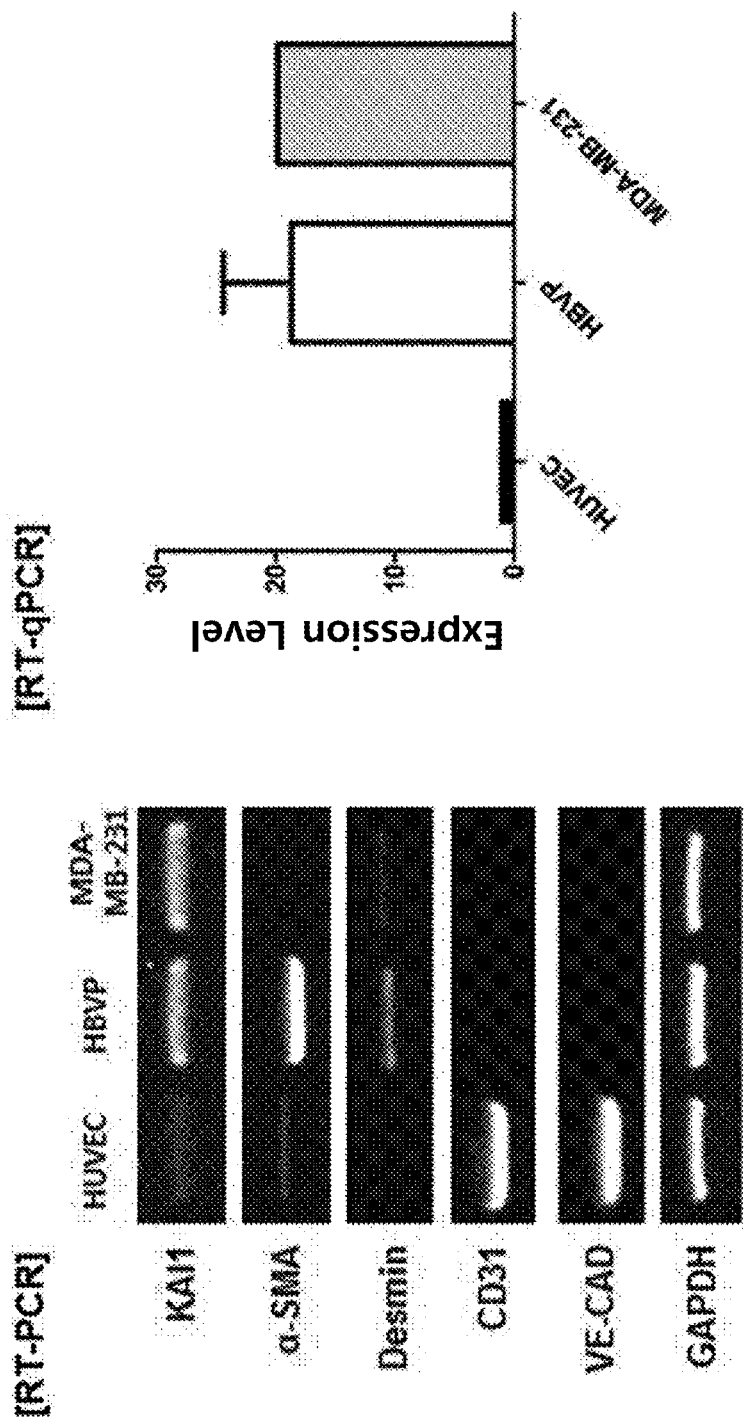

As a result, as shown in FIGS. 12A and 12B and FIG. 13, it can be confirmed that KAI1 was expressed in neither MS-1 positive nor EC markers such as CD31 and VE-CAD, whereas KAI1 was expressed in α-SMA, Desmin-positive mVSMC, and 10T1/2, and it can be seen from the result that KAI1 was expressed in pericytes wrapping around ECs, rather than the ECs themselves.

Figure 14A:
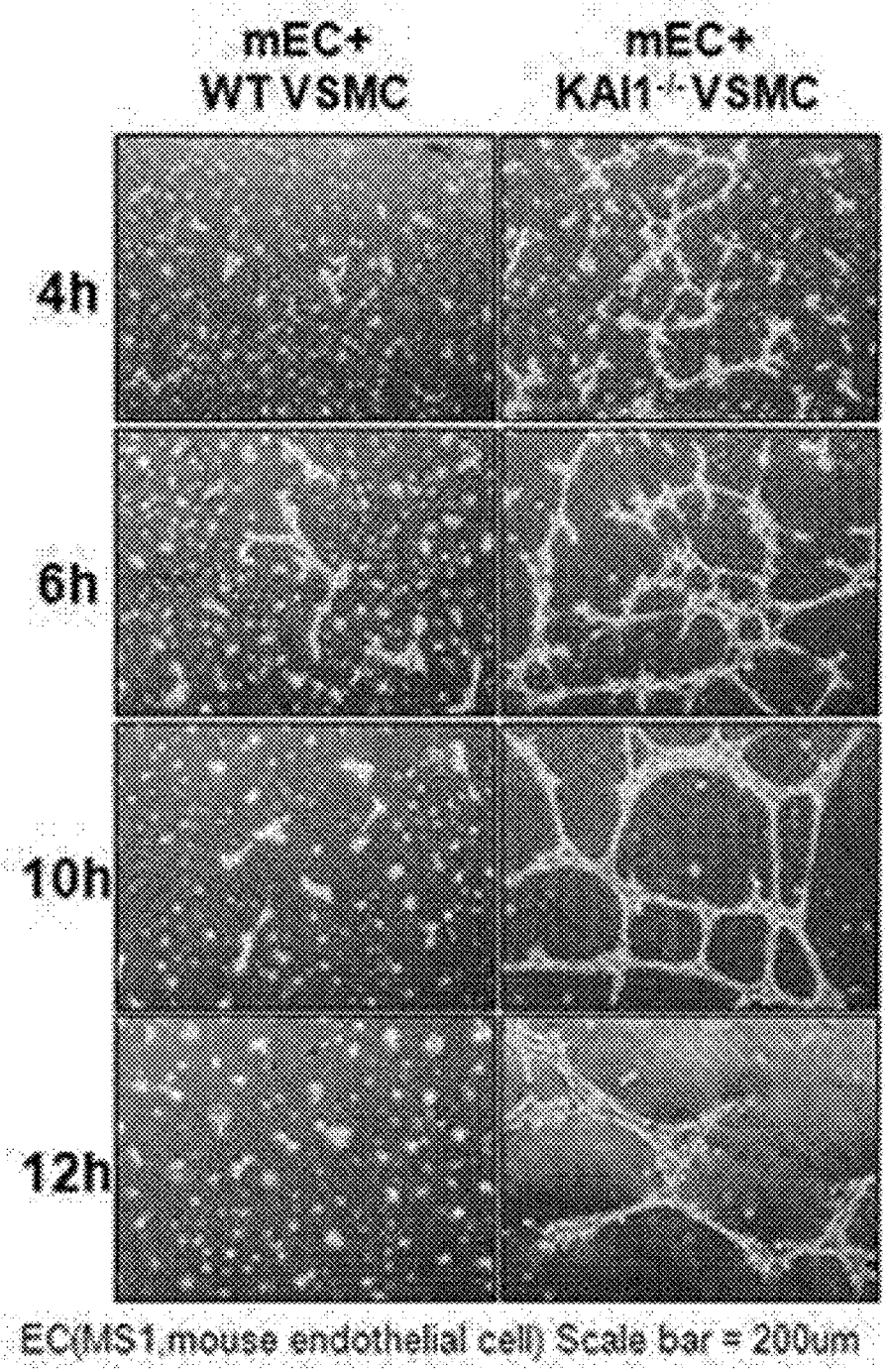
FIGS. 14A and 14B show the result of a co-tube formation assay for MS-1 in WT or KAI1$^{-/-}$ mVSMC in an in vitro angiogenic environment.
Figure 14B:
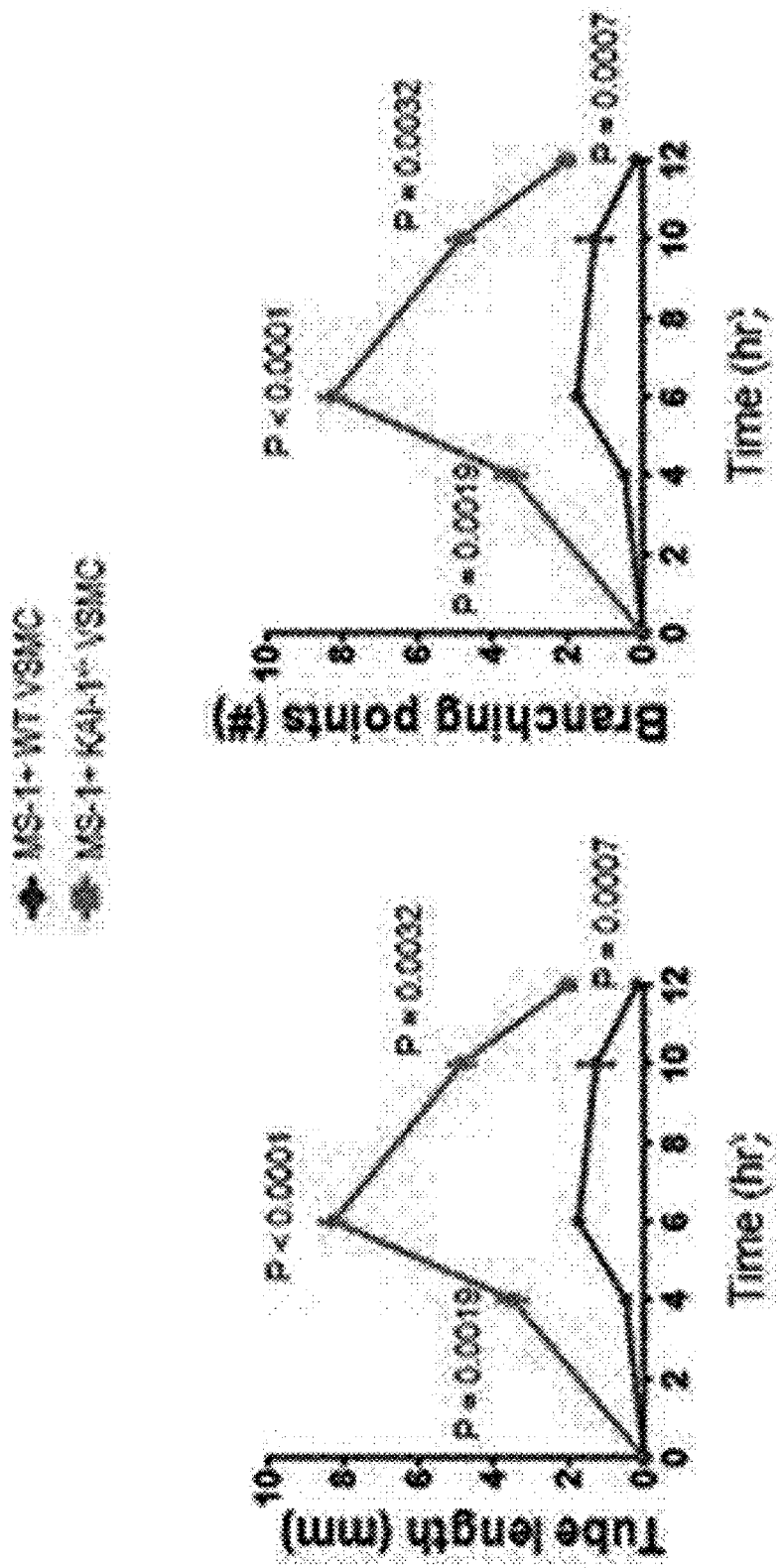
Figure 15A:
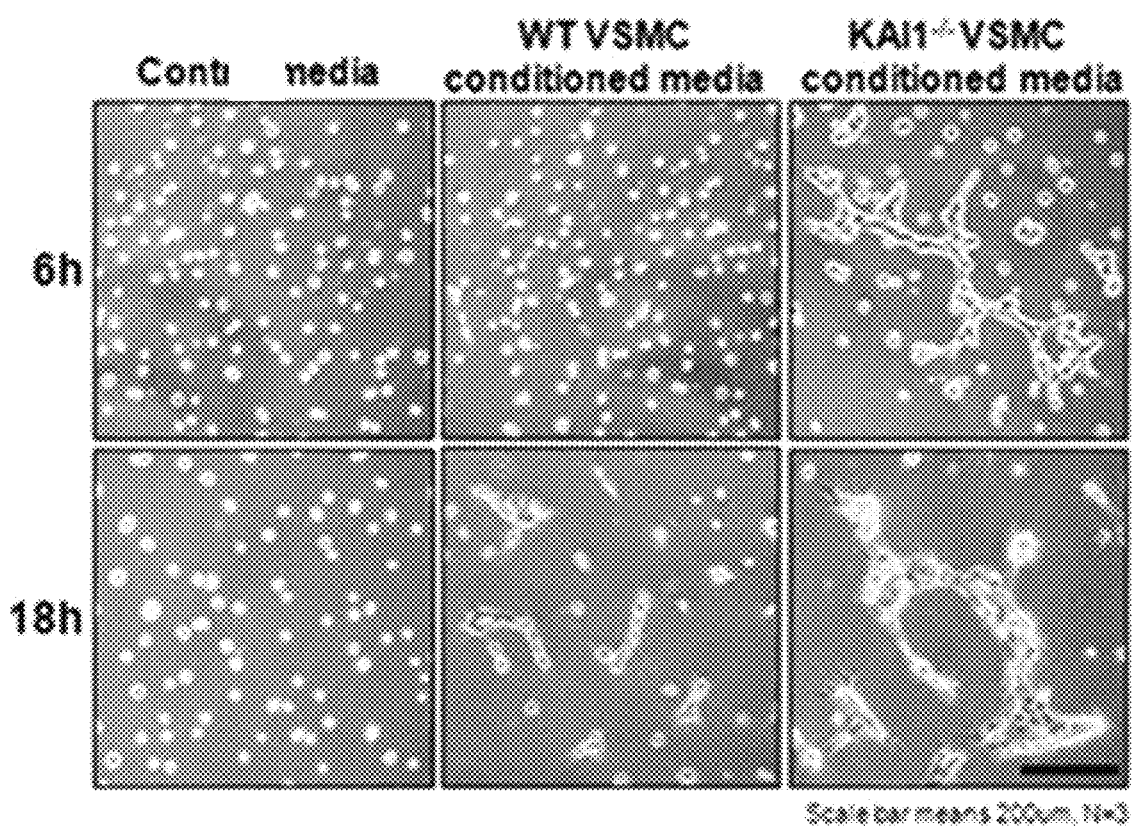
FIGS. 15A and 15B and FIGS. 16A and 16B show the result of analyzing a tube length and the number of branching points (FIGS. 15A and 15B) and sprouting tip cells and their lengths (FIGS. 16A and 16B) through an MS-1 tube-formation assay using culture media for culturing WT or KAI1$^{-/-}$ mVSMC (WT or KAI1$^{-/-}$ mVSMC conditioned media), to confirm whether the inhibition of an angiogenic tendency of MS-1 by mVSMC is caused by a paracrine effect.
Figure 15B:
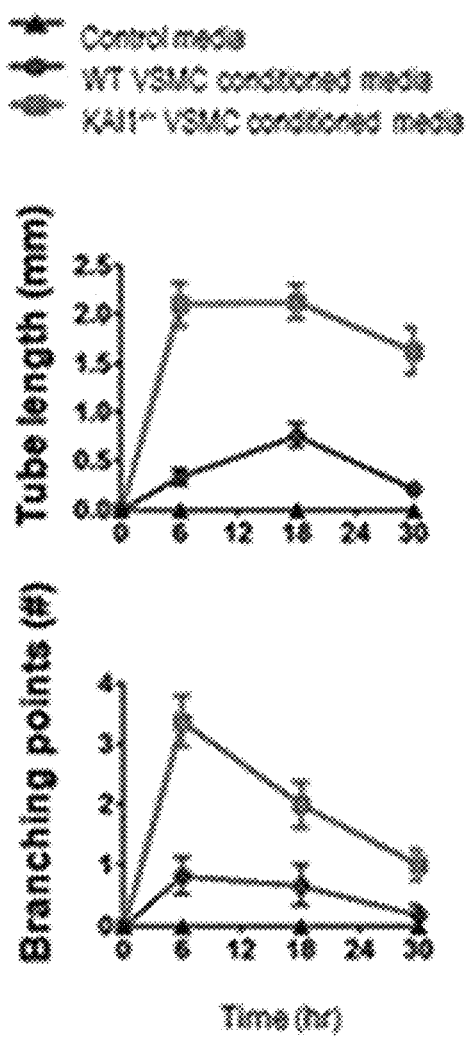
Figure 16A:
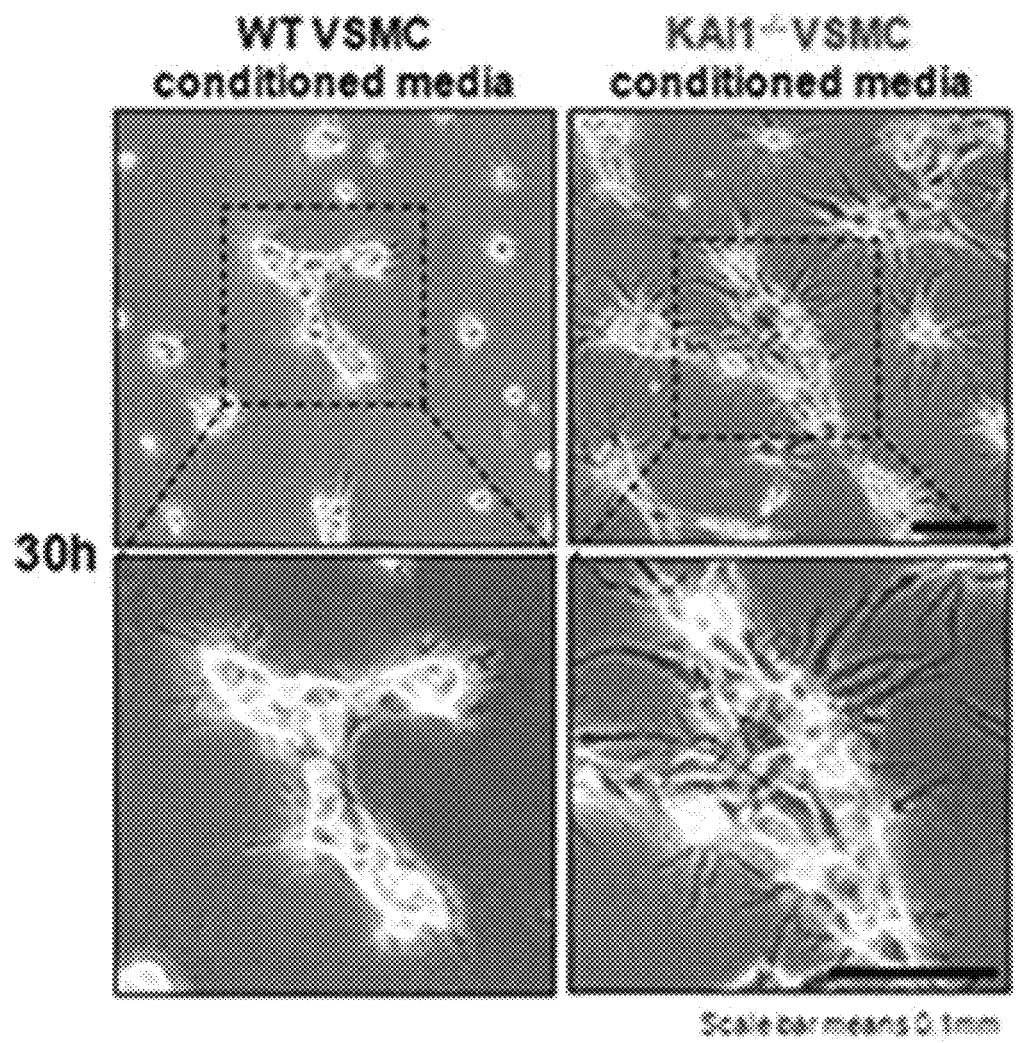
Figure 16B:
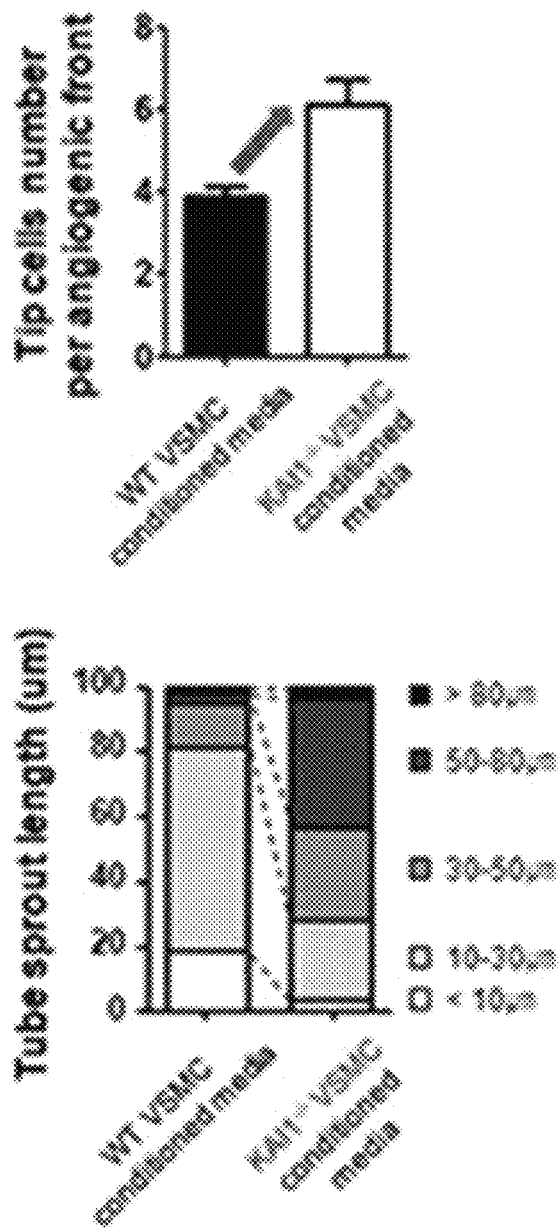

Example 3. Confirmation of Inhibition of Angiogenetic Tendency of ECs of KAI1 Expressed-mVSMC To identify an effect of KAI1 expression of mVSMC on MS-1 angiogenesis, a co-tube formation assay was performed to compare a degree of tube formation by culturing WT or KAI1$^{-/-}$ mVSMC together with MS-1 on a matrigel in an in vitro angiogenic environment, and the result is shown in FIGS. 14A and 14B. The WT or KAI1$^{-/-}$ mVSMC used in the experiment was prepared by isolating primary VSMC from the aorta of a WT mouse or a KAI1$^{-/-}$ mouse using 2 mg/ml of collagenase A, and proliferating the isolated primary VSMC by culturing with DMEM 20% FBS 1× antibiotics-antimycotics. As shown in FIGS. 14A and 14B, in terms of the tube length and the number of branching points, it can be confirmed that tube formation was more inhibited in the group subjected to co-tube formation with WT mVSMC than in the KAI1$^{-/-}$ group.

Figure 17B:
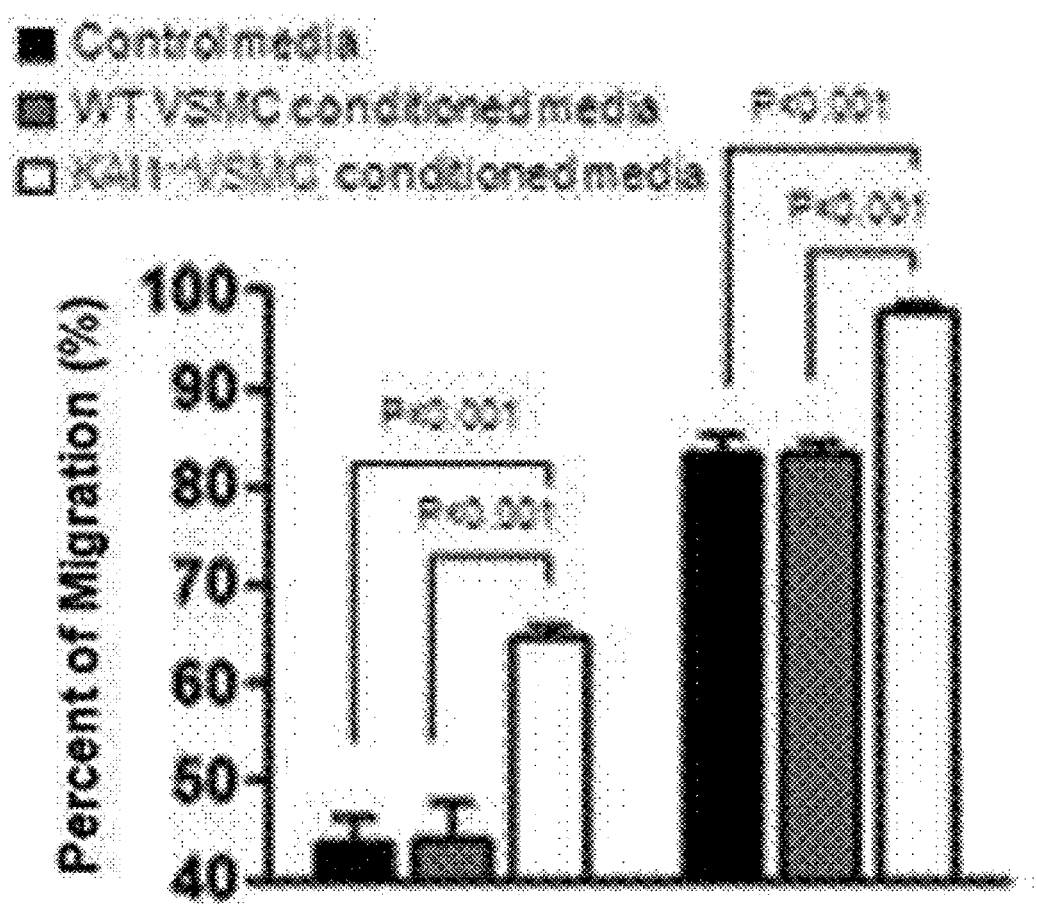

In addition, to confirm whether the inhibition of the angiogenic tendency of MS-1 by the mVSMC expressing KAI1 was caused by a paracrine effect, a degree of tube formation on a matrigel by MS-1 was compared using culture media for culturing WT or KAI1−/− mVSMC (WT or KAI1$^{-/-}$ mVSMC conditioned media), and a wound healing degree was compared after the MS-1 monolayer was wounded using a 200p tip, and the results are shown in FIGS. 15A, 15B, 16A, 16B, 17A and 17B, respectively. As shown in FIGS. 15A, 15B, 16A and 16B, it can be confirmed that, compared to the KAI1$^{-/-}$ group, the tube length and number of branching points were smaller and the number of sprouting tip cells and the length of the tip cells were smaller in the tube formation performed in the WT mVSMC conditioned media. In addition, as shown in FIGS. 17A and 17B, it can be confirmed through a scratch wound healing assay that the WT mVSMC conditioned media inhibited MS-1 migration more than the KAI1$^{-/-}$ group.

Figure 19:
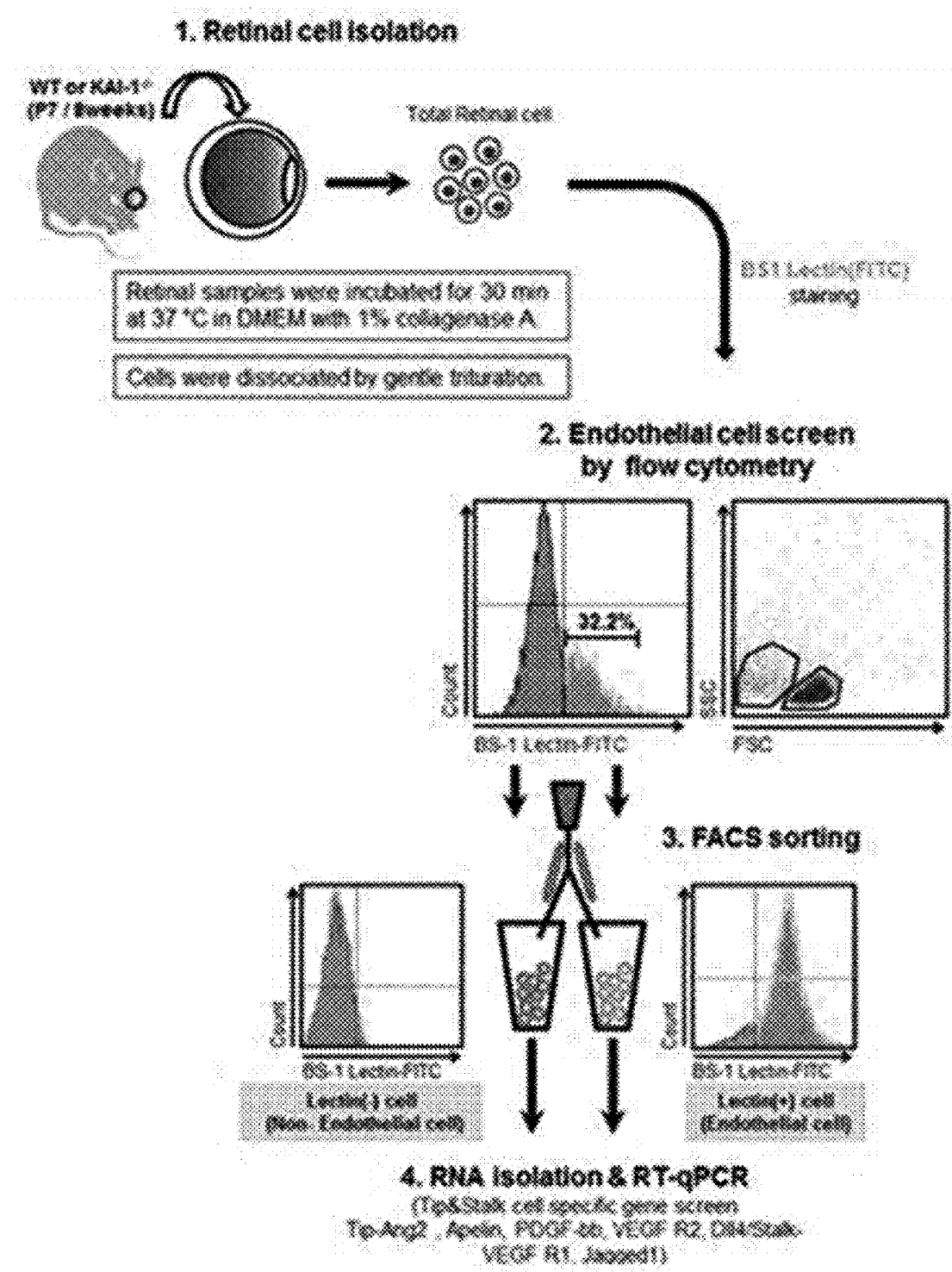
FIG. 19 shows a schematic process of an experiment to compare tip and stalk cell-specific gene expression in EC according to KAI1 expression.
Figure 20A:
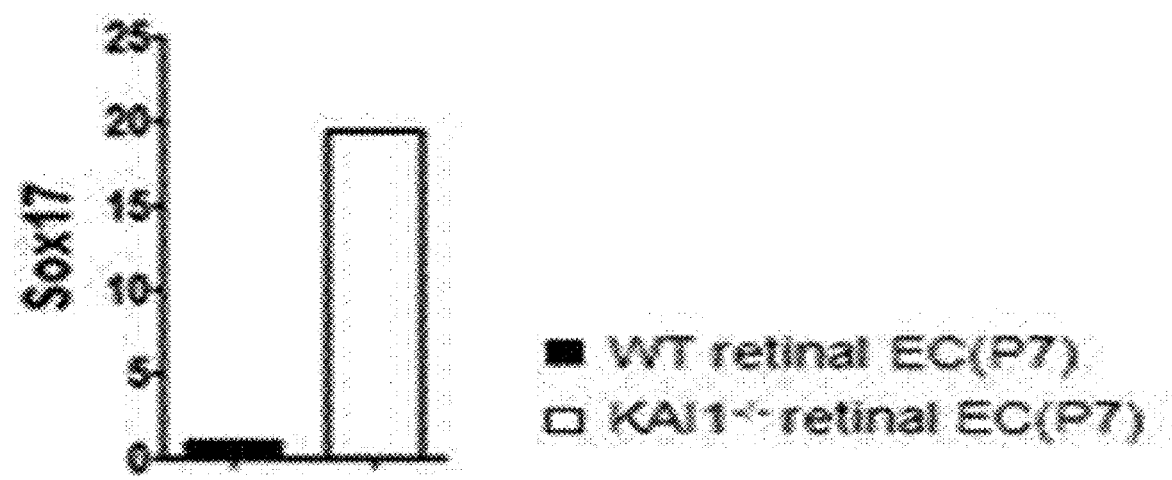
FIGS. 20A and 20B show the result of tip and stalk cell-specific gene screening according to the experimental process of FIGS. 18A and 18B.
Figure 20B:
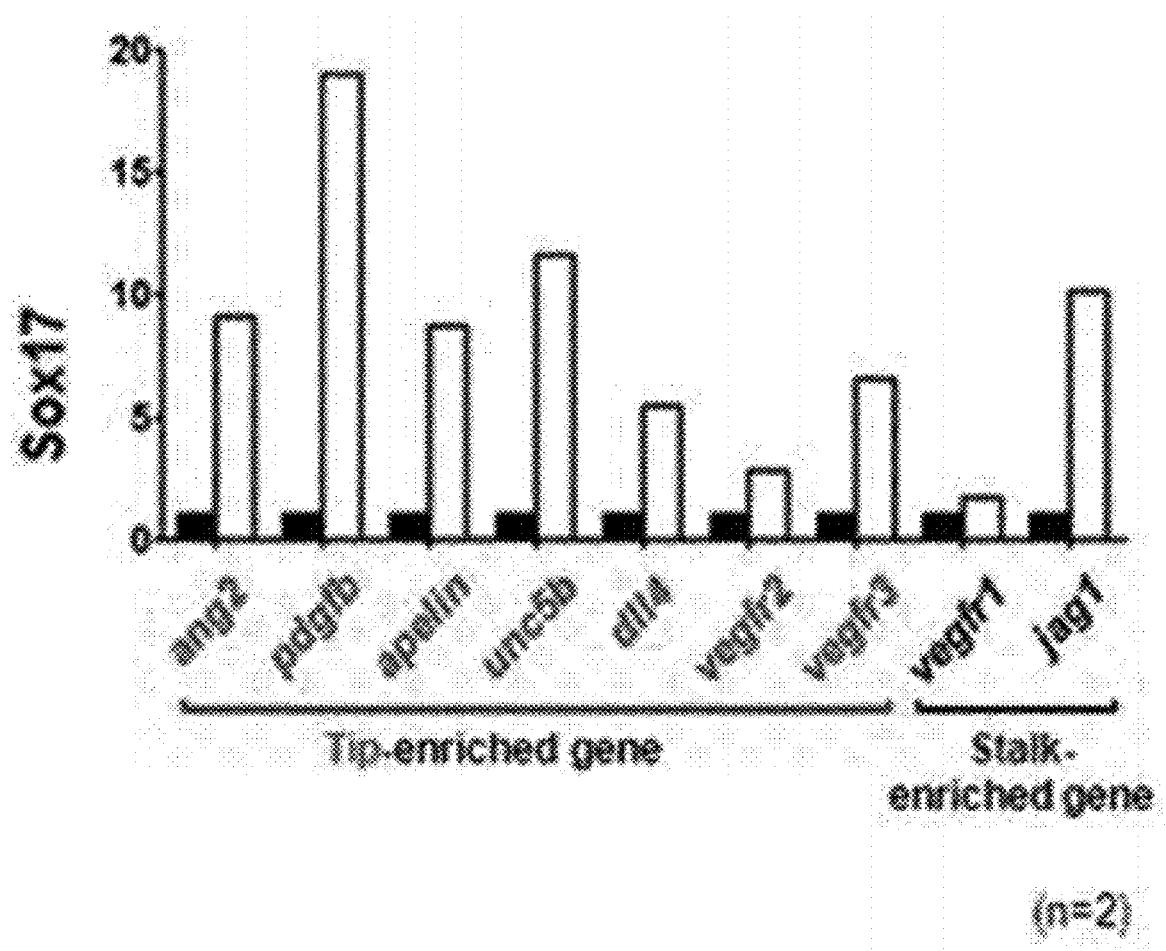

More specifically, as shown in FIG. 19, a 7-day-old WT or KAI1$^{-/-}$ mouse which was known that vasculogenesis actively occurred therein was harvested and cultured in 1% collagenase A-containing DMEM medium at 37° C. for 30 minutes. To isolate ECs from the retinal cells obtained therefrom, the retinal cells were stained with BS-1 lectin to sort a BS-1 lectin-positive group through FACS, and tip and stalk cell-specific gene screening was performed using RT-qPCR. The result is shown in FIGS. 20A and 20B. Primer information used herein is listed in Table 2 below.

TABLE 2

| Type | | Primer sequence |
|---|---|---|
| Ang2 | FW(Forward) | 5'-GAAGGACTGGGAAGGCAACGA-3' (SEQ ID NO: 17) |
| | RV(Reverse) | 5'-CCACCAGCCTCCTGAGAGCAT-3' (SEQ ID NO: 18) |
| PDGFb | FW(Forward) | 5'-ACAGGGAAGTGGACTCCGATACT-3' (SEQ ID NO: 19) |
| | RV(Reverse) | 5'-ACATCCGTGTCCTGTTCCCGA-3' (SEQ ID NO: 20) |
| Apelin | FW(Forward) | 5'-CGAGTTGCAGCATGAATCTGAG 3' (SEQ ID NO: 21) |
| | RV(Reverse) | 5'-TGTTCCATCTGGAGGCAACATC-3' (SEQ ID NO: 22) |
| Unc5b | FW(Forward) | 5'-GAGTGGCTATGCTTGTGATTTGG-3' (SEQ ID NO: 23) |
| | RV(Reverse) | 5'-CATAGCAAAGCCTTTCCCTGTG-3' (SEQ ID NO: 24) |
| Dll4 | FW(Forward) | 5'-AGGTGCCACTTCGGTTACAC-3' (SEQ ID NO: 25) |
| | RV(Reverse) | 5'-GGGAGAGCAAATGGCTGATA-3' (SEQ ID NO: 26) |
| VEGFR3 | FW(Forward) | 5'-TGGTACCGGCTCAACCTCTC-3' (SEQ ID NO: 27) |
| | RV(Reverse) | 5'-CACGTTTTTGCAGTCCAGCA-3' (SEQ ID NO: 28) |
| VEGFR1 | FW(Forward) | 5'-GAGGAGGATGAGGGTGTCTATAGGT-3' (SEQ ID NO: 29) |
| | RV(Reverse) | 5'-GTGATCAGCTCCAGGTTTGACTT-3' (SEQ ID NO: 30) |
| Jag1 | FW(Forward) | 5'-GAGGCGTCCTCTGAAAAACA-3' (SEQ ID NO: 31) |
| | RV(Reverse) | 5'-ACCCAAGCCACTGTTAAGACA-3' (SEQ ID NO: 32) |
| GAPDH | FW(Forward) | 5'-TGTCCGTCGTGGATCTGAC-3' (SEQ ID NO: 33) |
| | RV(Reverse) | 5'-CCTGCTTCACCACCTTCTTG-3' (SEQ ID NO: 34) |
| SOX17 | FW(Forward) | 5'-CAGCAAGATGCTGGGAAAGT-3' (SEQ ID NO: 35) |
| | RV(Reverse) | 5'-GTTGGGGTAGTCCTGCATGT-3' (SEQ ID NO: 36) |
| VEGFR2 | FW(Forward) | 5'-ATCGGAGAAGAACGTGGTTAAA 3' (SEQ ID NO: 37) |
| | RV(Reverse) | 5-CAAATGTTCCACCAACTCTGAA-3' (SEQ ID NO: 38) |

Figure 18A:
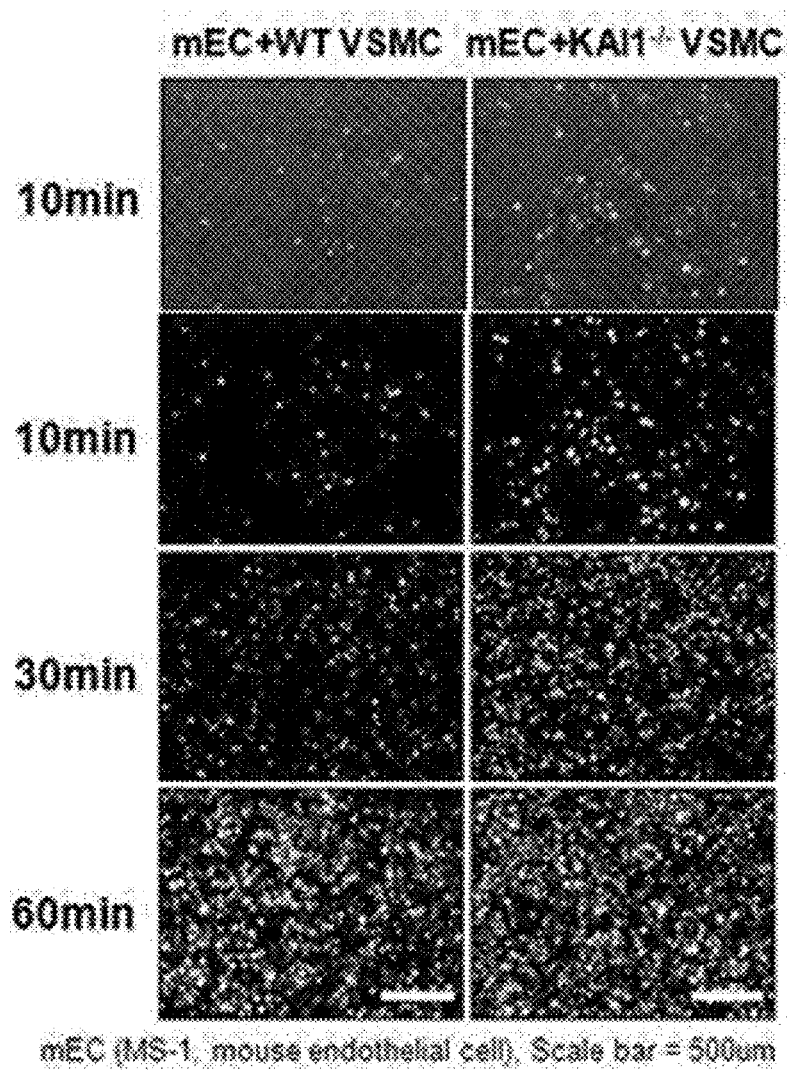
FIGS. 18A and 18B shows the result of comparing adhesion ability of mVSMC with respect to MS-1 after WT or KAI1$^{-/-}$ mVSMC was seeded into an MS-1 monolayer, to confirm the adhesion ability to EC according to KAI1 expression of a pericyte.
Figure 18B:
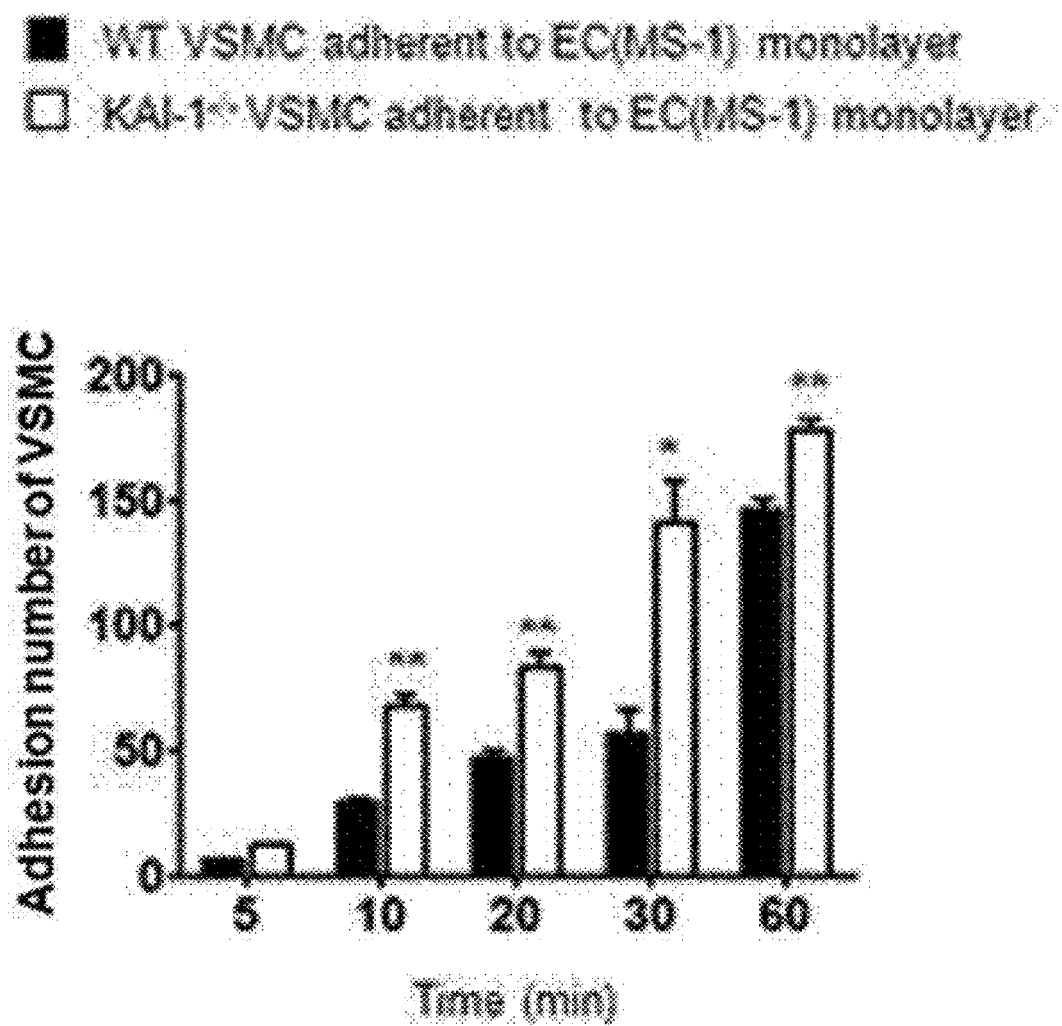

Moreover, to identify an ability of pericytes to be adhered to ECs according to KAI1 expression, WT or KAI1$^{-/-}$ mVSMCs stained in a red color were seeded into an MS-1 monolayer, and after a predetermined time, non-adhered cells were removed and then only adhered VSMCs were observed to compare adhesion abilities of mVSMCs with respect to MS-1. The result is shown in FIGS. 18A and 18B. As shown in FIGS. 18A and 18B, it can be confirmed that the adhesion ability of the WT mVSMC with respect to MS-1 was less than that of the KAI1$^{-/-}$ mVSMC.

From the result, it can be seen that the angiogenic tendency of ECs was inhibited by the KAI1-expressed mVSMCs through both a direct effect and a paracrine effect.

Example 4. Comparison of Tip and Stalk Cell-Specific Genes in ECs According to KAI1 Expression To compare the expressions of tip and stalk cell-specific genes in ECs according to KAI1 expression, an experiment was carried out as follows, and a schematic process of the experiment is shown in FIG. 19.

As shown in FIGS. 20A and 20B, it can be confirmed that expression of Sox17 and genes expression in tip and stalk cells were greater in KAI1$^{-/-}$ retinal ECs than WT retinal ECs. In other words, gene expression in tip and stalk cells of KAI1-expressing ECs were less than that of ECs not expressing KAI1.

Figure 21A:
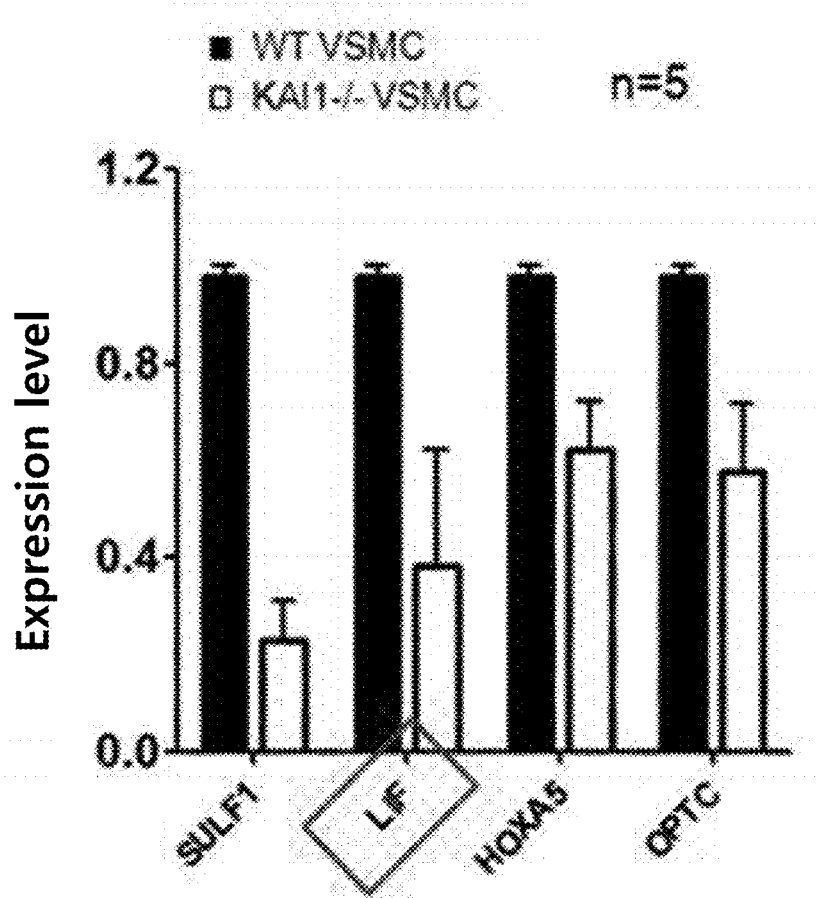
FIGS. 21A and 21B show the result of confirming RNA sequencing using WT and KAI1$^{-/-}$ mVSMC RNA through RT-PCR and Western blotting.
Figure 21B:
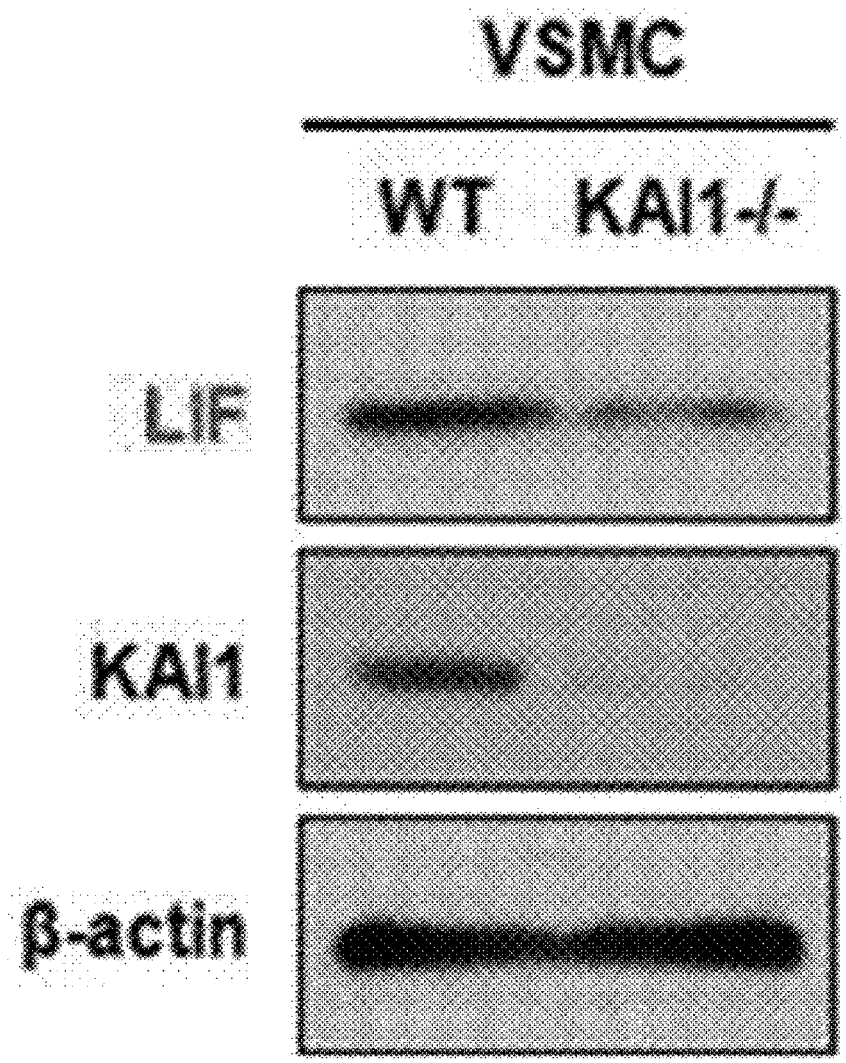

Example 5. Identification of Genetic Difference Between Pericytes According to KAI1 Expression To identify a genetic difference between pericytes expressing KAI1 and pericytes not expressing KAI1, RNA sequencing using WT and KAI1$^{-/-}$ mVSMC RNA isolated from the aortas of a WT mouse and a KAI1$^{-/-}$ mouse using collagenase A was identified through RT-PCR and Western blotting, and the result is shown in FIGS. 21A and 21B. Here, primer information used in the RT-PCR is listed in Table 3 below.

TABLE 3

| Type | | Primer sequence | |
|---|---|---|---|
| OPTC | FW(Forward) | 5'-TGAGGGGGTGTCTAGCTGTC-3' | (SEQ ID NO: 39) |
|  | RV(Reverse) | 5'-TCTGAGGGAGGGGTAGGAGT-3' | (SEQ ID NO: 40) |
| PF4 | FW(Forward) | 5'-AGTCCTGAGCTGCTGCTTCT-3' | (SEQ ID NO: 41) |
|  | RV(Reverse) | 5'-GGCAAATTTTCCTCCCATTC-3' | (SEQ ID NO: 42) |
| HOXA5 | FW(Forward) | 5'-AAAAACTCCCTGGGCAACTC-3' | (SEQ ID NO: 43) |
|  | RV(Reverse) | 5'-TGGGCCACCTATATTGTCGT-3' | (SEQ ID NO: 44) |
| SULF1 | FW(Forward) | 5'-CCAAACGACACAATCCACTG-3' | (SEQ ID NO: 45) |
|  | RV(Reverse) | 5'-TGAAGGGGTGAAGGTGACTC-3' | (SEQ ID NO: 46) |
| Serpinf1 | FW(Forward) | 5'-ACTGCCCCTGAGAAGAACCT-3' | (SEQ ID NO: 47) |
|  | RV(Reverse) | 5'-GCCTGCACCCAGTTGTTAAT-3' | (SEQ ID NO: 48) |
| LIF | FW(Forward) | 5'-TACCGCATAGTCGTGTACCTTG-3' | (SEQ ID NO: 49) |
|  | RV(Reverse) | 5'-ACTGGGGTTGAGGATCTTCTG-3' | (SEQ ID NO: 50) |
| CD59A | FW(Forward) | 5'-AGCCGGAATGCAAGTGTATC-3' | (SEQ ID NO: 51) |
|  | RV(Reverse) | 5'-ATGGTGTCTTCCCCAAGGAT-3' | (SEQ ID NO: 52) |
| CCL2 | FW(Forward) | 5'-CAGGTCCCTGTCATGCTTCT-3' | (SEQ ID NO: 53) |
|  | RV(Reverse) | 5'-TCTGGACCCATTCCTTCTTG-3' | (SEQ ID NO: 54) |
| KLF4 | FW(Forward) | 5'-CCAAAGAGGGGAAGAAGGTC-3' | (SEQ ID NO: 55) |
|  | RV(Reverse) | 5'-CCTGTGTGTTTGCGGTAGTG-3' | (SEQ ID NO: 56) |
| Anigotensin | FW(Forward) | 5'-CCAGACACCCCTGCTACAGT-3' | (SEQ ID NO: 57) |
|  | RV(Reverse) | 5'-TCTGTACTGACCCCCTCCAG-3' | (SEQ ID NO: 58) |
| ADAMTS1 | FW(Forward) | 5'-GGTCACCTTGCAGTGCCTAC-3' | (SEQ ID NO: 59) |
|  | RV(Reverse) | 5'-CCAGTGCACCACAGGGTAGT-3' | (SEQ ID NO: 60) |
| ROCK2 | FW(Forward) | 5'-CAGGGAGGTACGACTTGGAA-3' | (SEQ ID NO: 61) |
|  | RV(Reverse) | 5'-TCGGGAAGGTCTCTACATCG-3' | (SEQ ID NO: 62) |
| ROCK1 | FW(Forward) | 5'-CCTGCCCTAGAGTGTCGAAG-3' | (SEQ ID NO: 63) |
|  | RV(Reverse) | 5'-TCTTGTTGACAGCGTTCGAG-3' | (SEQ ID NO: 64) |
| Thrombospondin2 | FW(Forward) | 5'-GGGTCTGTGGACTTCAGTGG-3' | (SEQ ID NO: 65) |
|  | RV(Reverse) | 5'-GCCAGTACCAGTCGTGGAGT-3' | (SEQ ID NO: 66) |
| STAT1 | FW(Forward) | 5'-CAGCTGAGTTCCGACACCTG-3' | (SEQ ID NO: 67) |
|  | RV(Reverse) | 5'-CACCACGACAGGAAGAGAGG-3' | (SEQ ID NO: 68) |

As shown in FIGS. 21A and 21B, it can be confirmed that the expression of 15 genes of negative angiogenic regulators was less in KAI1$^{-/-}$ mVSMC RNA, and when this was reproduced by real-time PCR, it was confirmed that 4 genes out of the 15 genes, such as LIF, SULF1, HOXA5 and OPTC, were significantly less expressed.

Figure 22A:
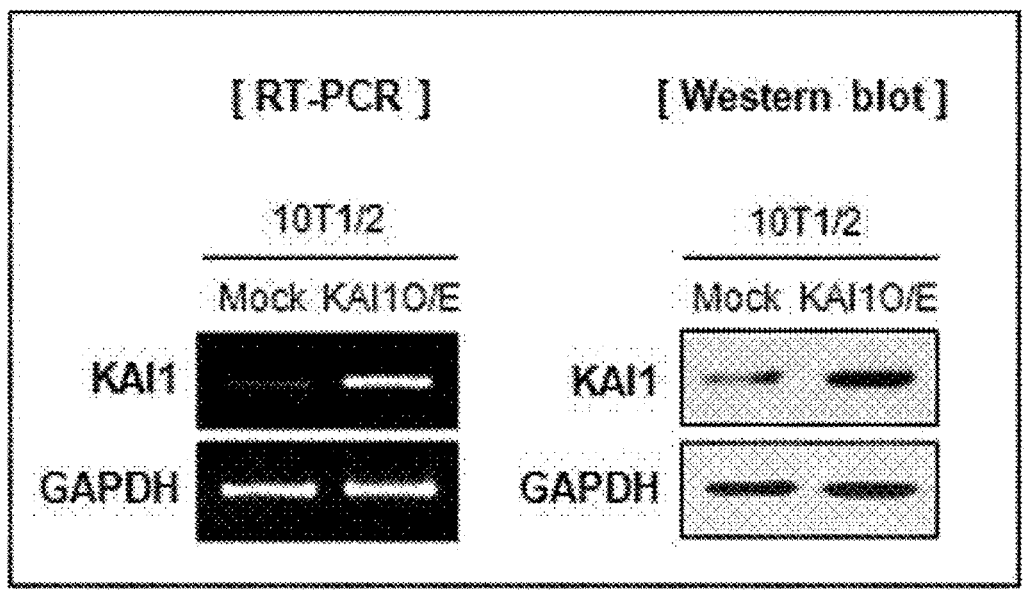
FIGS. 22A to 22C show the results of real-time PCR and Western blotting to confirm the increases in expression of LIF, SULF1, HOXA5, and OPTC of a group in which 10T1/2 is transduced with KAI1 overexpression adenovirus and of a group in which 10T1/2 is transduced with mock adenovirus.
Figure 22B:
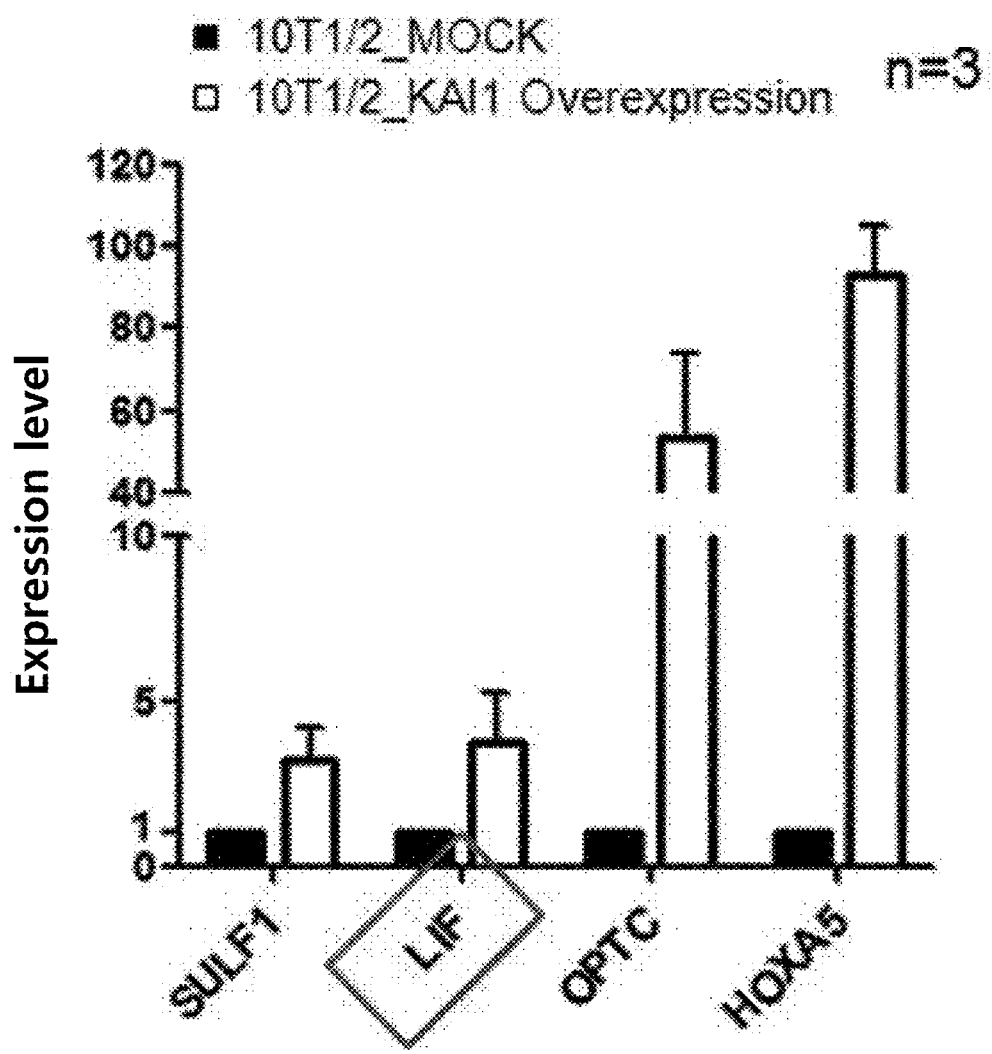
Figure 22C:
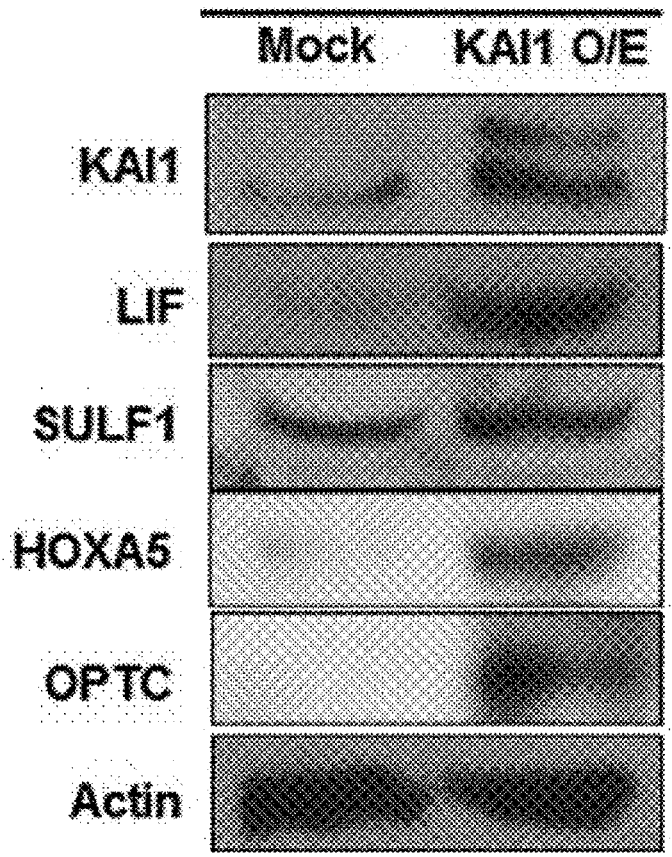

In addition, real-time PCR and Western blotting were used to determine the increase in expression of LIF, SULF1, HOXA5, and OPTC, after KAI1 expression was improved in 10T1/2 by transduction with KAI1 overexpression adenovirus and comparing with a group transduced with mock adenovirus, and the result is shown in FIGS. 22A to 22C. As shown in FIGS. 22A to 22C, it can be confirmed that compared to an un-treated group, expression of LIF, SULF1, HOXA5, and OPTC was greater in the group increased in KAI1 expression.

Example 6. Confirmation of Increase/Decrease in Expression of Anti-Angiogenic Factors of a KAI1-Expression Pericyte To investigate by which mechanism angiogenesis is inhibited, according to gene ontology analysis with data obtained from RNA sequencing performed with primary vascular smooth muscle cells (VSMCs) obtained from both a KAI1 wild type (WT) and a knockout (KO) mouse by the same method as described in Example 5, it was observed that expression levels of genes of a negative angiogenic regulator (GO: 0016525) set as a leukemia inhibitory factor (LIF), homeoboxA5 (HOXA5), sulfatase1 (SULF1) and opticin (OPTC) were significantly greater in KAI1 KO VSMCs. To confirm this in various types of pericytes, "KAI1 WT vs. KO VSMC", "mock vs. KAI1 overexpression 10T1/2", and "control siRNA vs. siKAI11 (when KAI1 gene expression is inhibited by siRNA) 10T1/2" sets were prepared to perform a reverse transcription-quantitative polymerase chain reaction (RT-qPCR).

Meanwhile, to find a link between four anti-angiogenic factors and KAI1, literature research was performed to find whether there are common transcription factors, and therethrough, Pbx1a, which commonly acts on LIF, HOXA5, and SULF1 promoters, was identified. Afterwards, the following experiment was performed while focusing on LIF out of the four anti-angiogenic factors, which was expressed at the highest level and had reproductivity.

Figure 23:
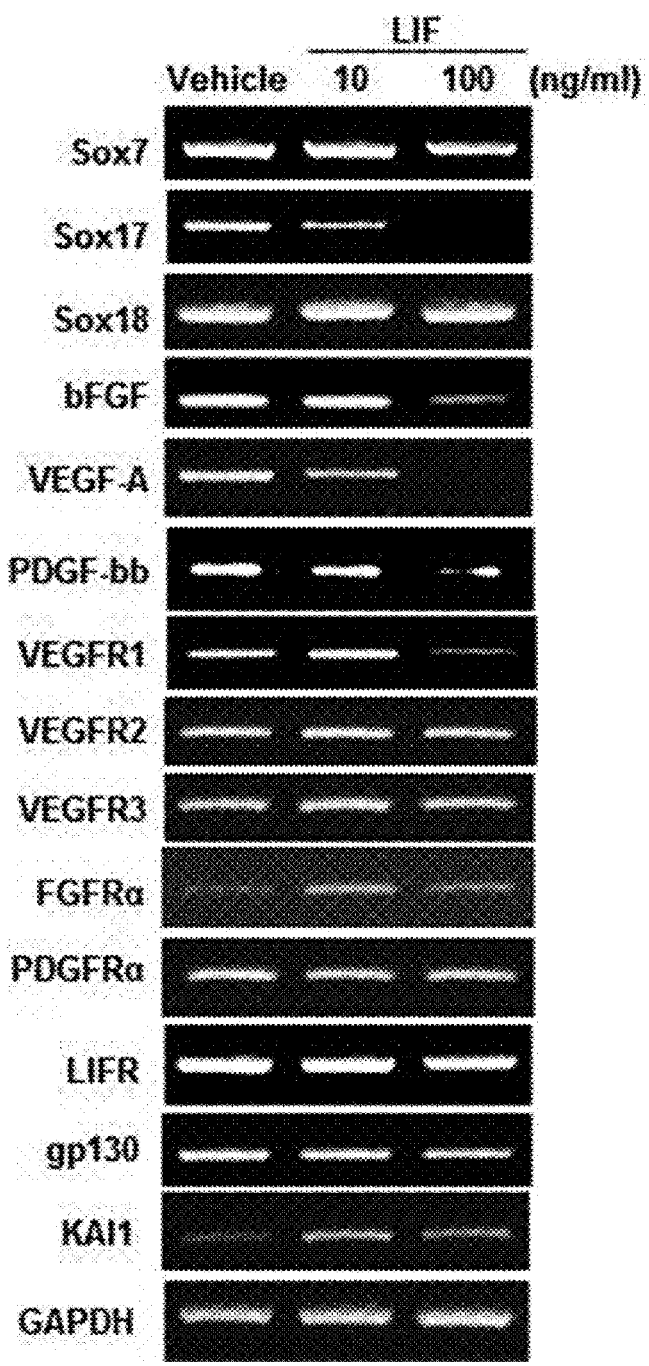
FIG. 23 shows the result of Sox17 gene expression after MS1 is treated with recombinant mouse LIF to observe whether EC sprouting is actually inhibited by LIF.

First, to observe whether LIF actually inhibited EC sprouting, MS1 was treated with recombinant mouse LIF, and thereafter the expression of Sox17 gene, known as a master switch of angiogenesis, was confirmed. The result is shown in FIG. 23. As shown in FIG. 23, when MS1 was treated with recombinant mouse LIF, it can be confirmed that the Sox17 gene was less expressed.

Afterwards, to visualize an inhibitory effect of LIF on EC sprouting, a tube formation assay was performed on a matrigel. More specifically, when KAI1 overexpression 10T1/2 was manufactured using KAI1 adenovirus, and seeded with MS1 onto a matrigel, it can be confirmed that a sprouting inhibitory effect was recovered by KAI1 overexpression in a group treated with a LIF neutralizing antibody (refer to FIG. 24).

Example 7. Confirmation of KAI1 Phosphorylation in Pericyte

Figure 25:
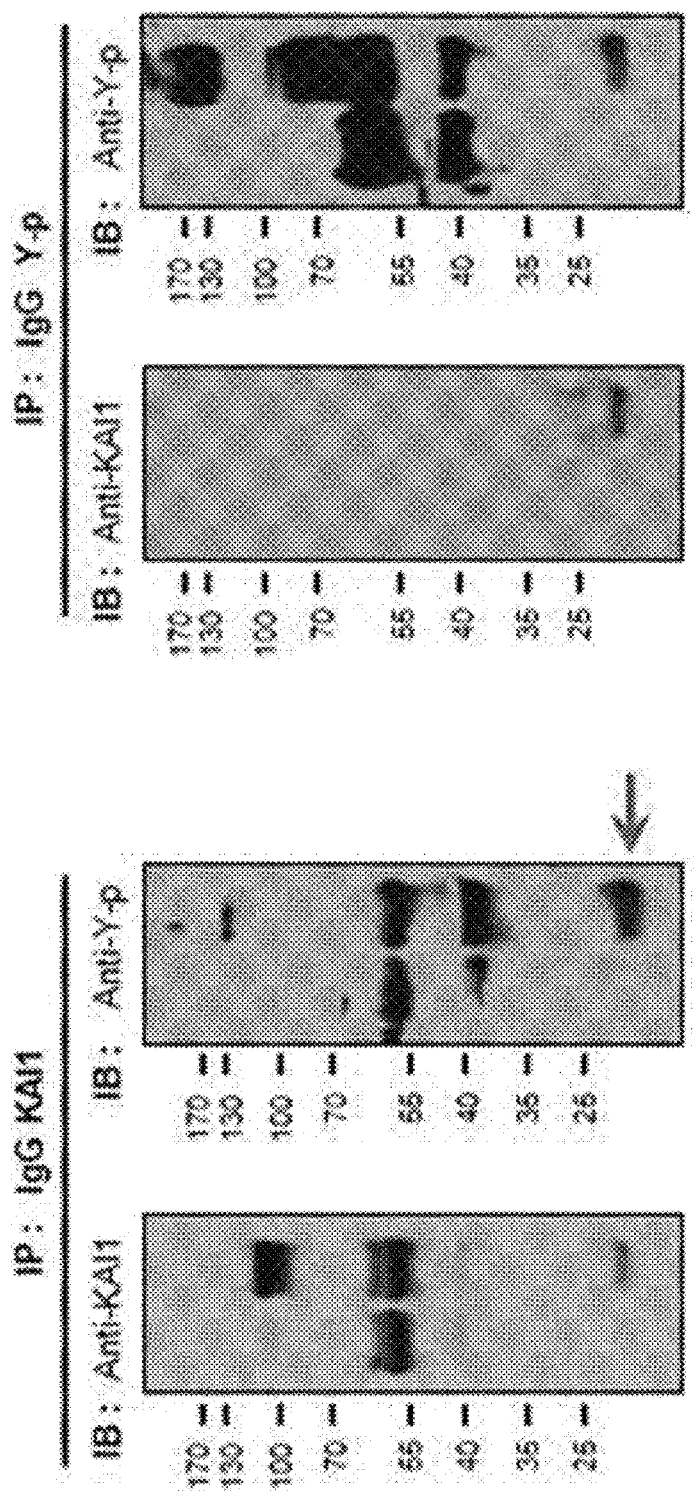
FIG. 25 shows the result of immunoprecipitation for a protein of WT and mVSMC using a KAI1 antibody.

After immunoprecipitation was performed on a protein of WT mVSMCs using a KAI1 antibody, immunoblotting for a phosphorylated tyrosine residue and immunoblotting with Src were performed. More specifically, a protein of WT mVSMC was obtained by the method described in Example 2 and quantified, and after incubated overnight with a predetermined amount of KAI1 antibodies at 4° C., the protein-antibody mixture was incubated with protein A agarose beads again at 4° C. for 2 hours to adhere the KAI1 antibody and the beads together. In addition, the beads were precipitated through centrifugation, and heated at 95° C. for 5 minutes to isolate the protein from the beads, followed by performing SDS-PAGE. As a result, it can be confirmed that, as shown in FIG. 25, KAI1 of WT mVSMC was phosphorylated and bound with total Src.

Figure 26:
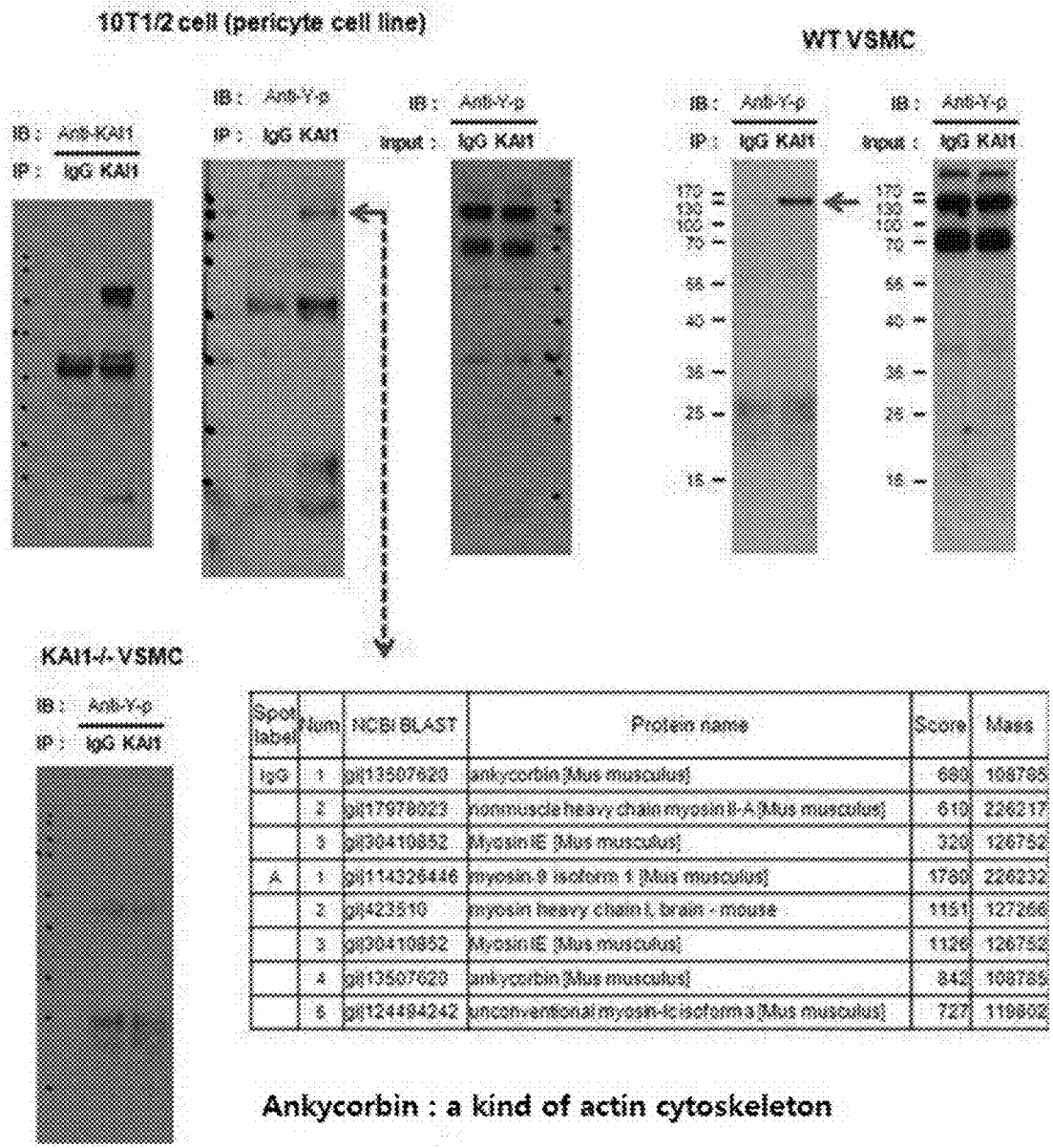
FIG. 26 shows the result of Western blotting using a protein of 10T1/2 in which KAI1 is overexpressed by a lentivirus to confirm how Src phosphorylation is changed according to KAI1 expression.

In addition, to confirm how the Src phosphorylation was changed according to KAI1 expression, Western blotting was performed using a protein of 10T1/2 in which KAI1 was overexpressed by a lentivirus, and the result is shown in FIG. 26. As shown in FIG. 26, although expression of total KAI1 did not change the amount of total Src, it can be confirmed that phosphorylation of Src at tyrosine residue 416 increased. In addition, it can be confirmed that the phosphorylation of Src at the tyrosine residue 416 was greater in a WT mVSMC protein than in a KAI1$^{-/-}$ mVSMC protein.

Example 8. Confirmation of Increase/Decrease in KAI1 Expression of Pericyte in Angiogenic Conditions 8-1. Selection of Optimum Cytokine Concentration Reducing KAI1

Figure 27A:
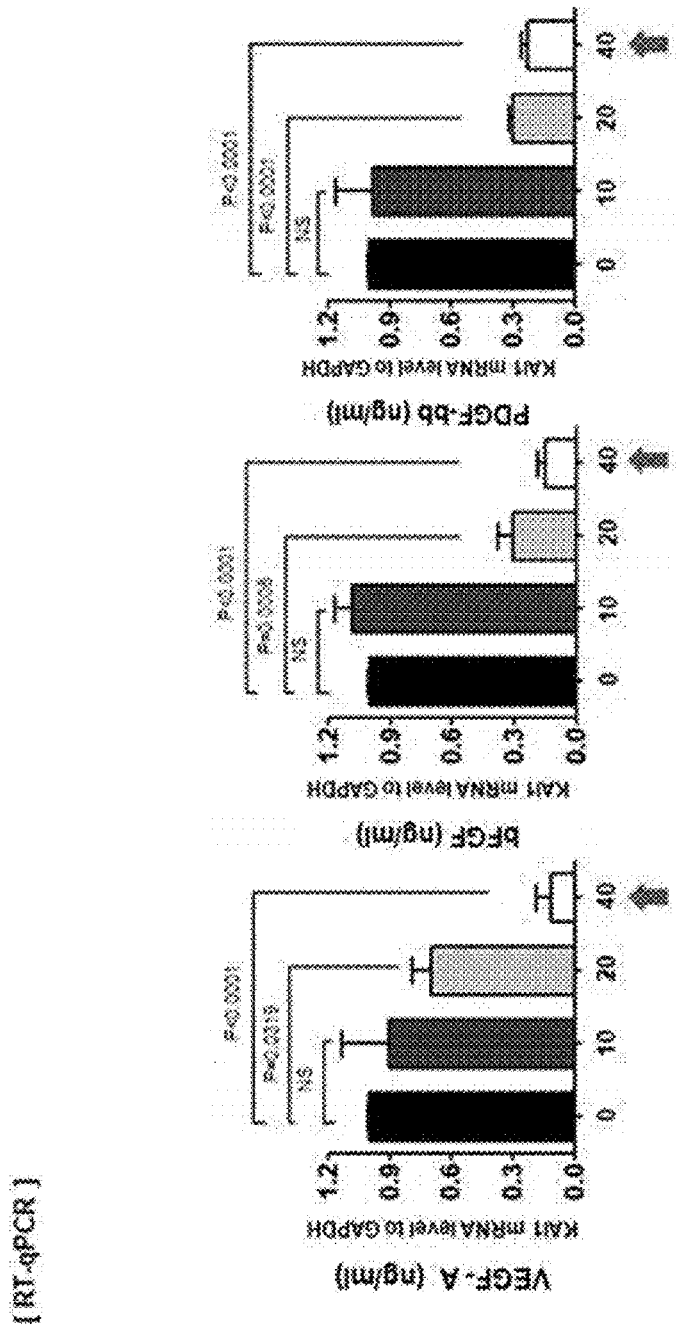
FIGS. 27A and 27B shows the results of qRT-PCR and Western blotting to determine optimum concentrations of KAI1 reducing VEGF-A, bFGF, and PDGF-bb.
Figure 27B:
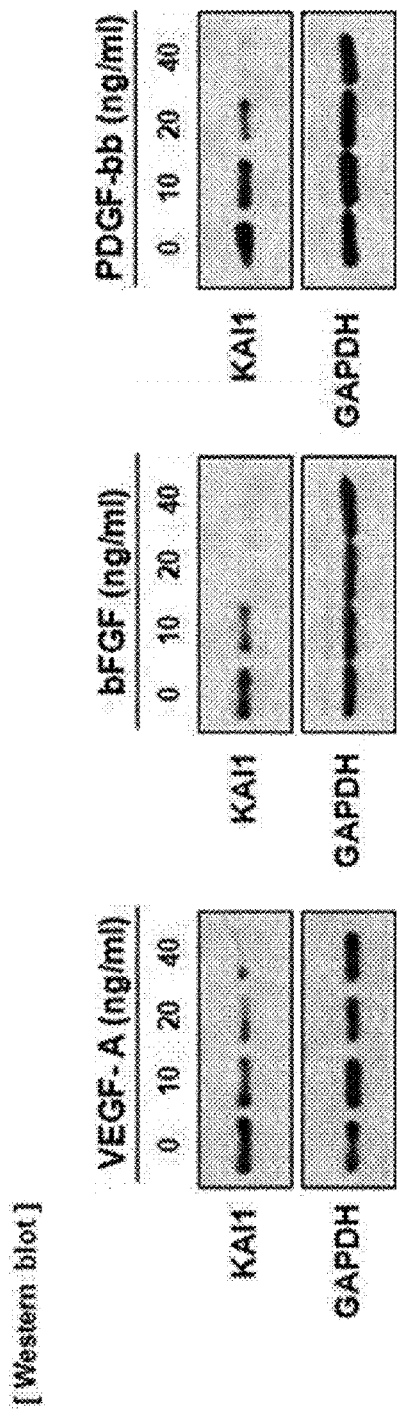

To prove the decrease in KAI1 expressed in pericytes in angiogenic conditions, an angiogenic environment was induced in vitro by treating 10T1/2 (mouse pericytes) with typical angiogenic factors such as VEGF-A, bFGF, and PDGF-bb per concentration (0, 10, 20, and 40 ng/ml), and then an optimum concentration reducing KAI1 was selected using qRT-PCR and Western blotting, and the result is shown in FIGS. 27A and 27B.

Figure 40:
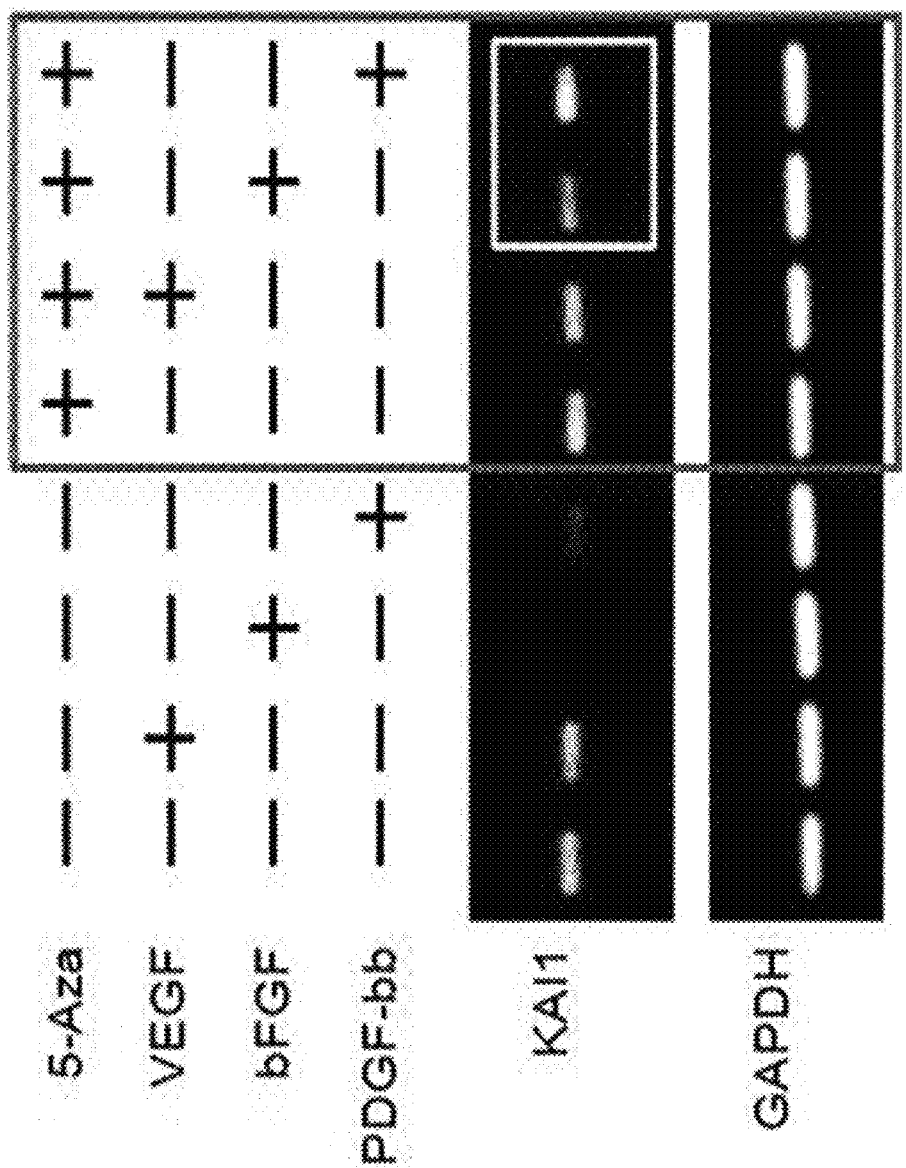
FIG. 40 shows the result of confirming a change in KAI1 expression according to the experimental process of FIG. 39.

As shown in FIGS. 27A and 27B, 40 ng/ml was determined as the optimum cytokine concentration reducing KAI1.

Figure 28:
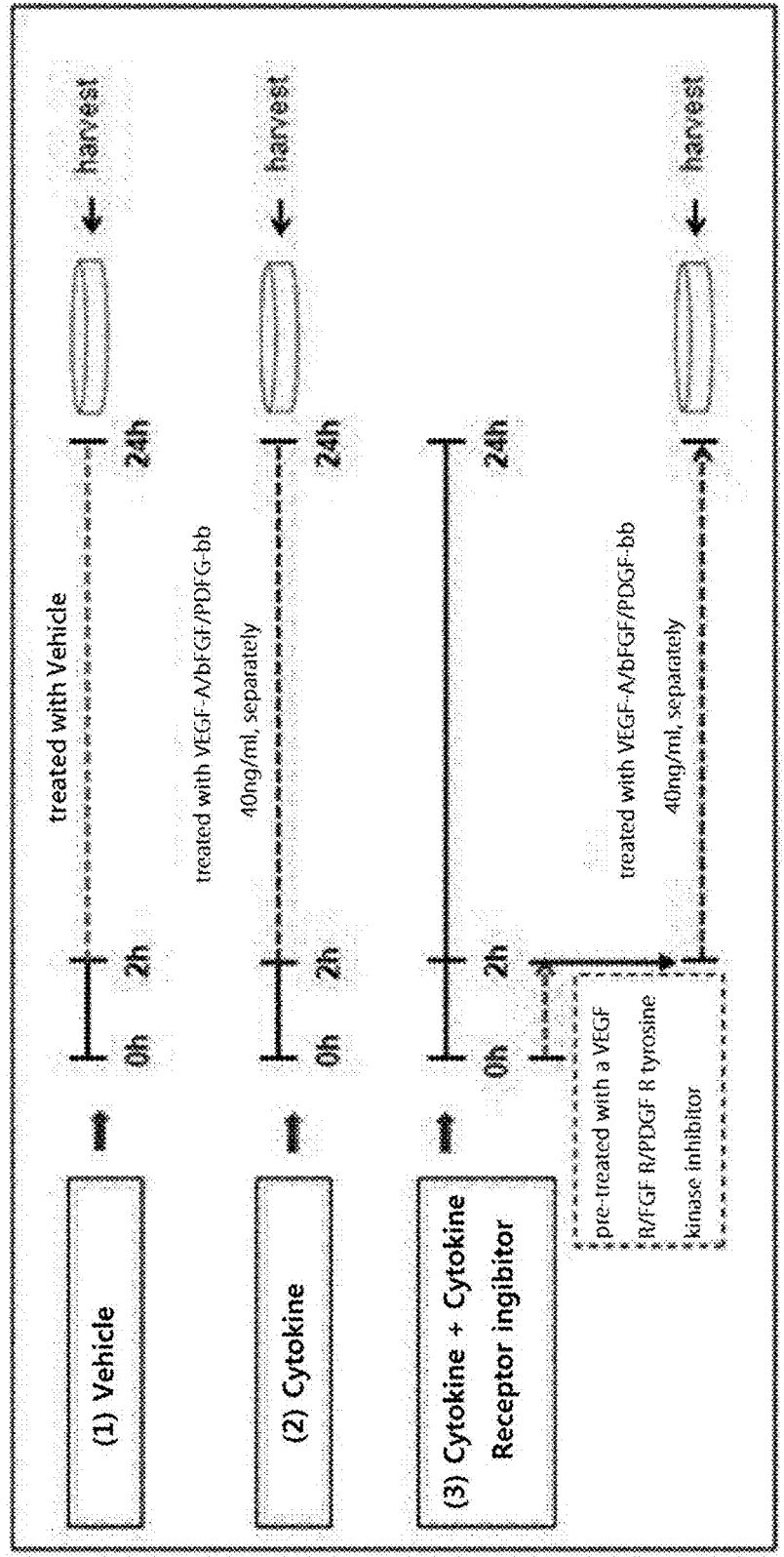
FIG. 28 shows a schematic process of an experiment to confirm whether the decrease in KAI1 expression by a cytokine is a receptor-mediated response.

8-2. Confirmation Whether Decrease in KAI1 Expression by Cytokine was Receptor-Mediated Response To confirm whether the decrease in KAI1 expression by a cytokine was a receptor-mediated response, an experiment was performed as follows, and a schematic process of the experiment is shown in FIG. 28.

Before 10T1/2 was treated with 40 ng/ml of a cytokine (VEGF-A, bFGF or PDGF-bb) selected in Example 8-1, a cytokine receptor inhibitor was treated beforehand. To this end, VEGF-A- and PDGF-bb-treated groups were treated with a tyrosine kinase inhibitor named SU11248, and a bFGF-treated group was pre-treated with a tyrosine kinase inhibitor named PD173074 for 2 hours, treated with 40 ng/ml of each cytokine (VEGF-A, bFGF, and PDGF-bb) as an angiogenic factor for 24 hours, and then harvested to confirm KAI1 expression through RT-qPCR and Western blotting, and the result is shown in FIGS. 29A and 29B.

Figure 29A:
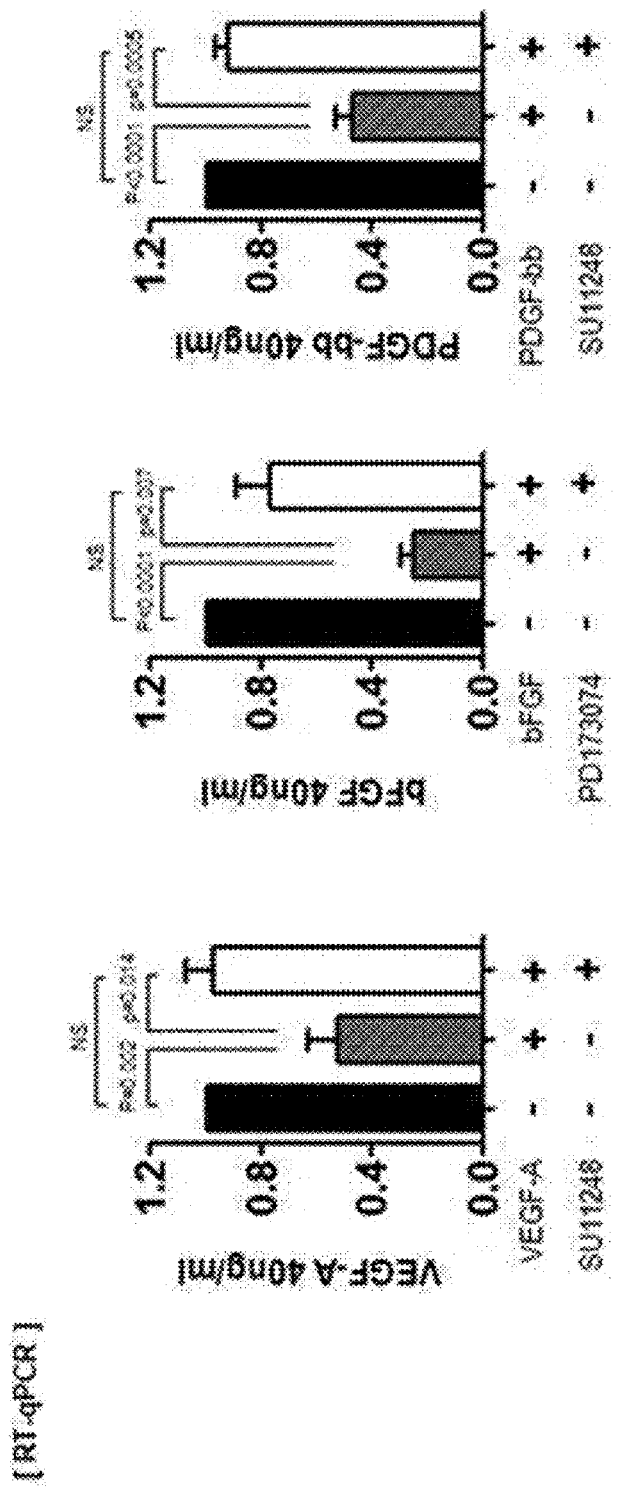
FIGS. 29A and 29B shows the results of RT-qPCR and Western blotting to confirm KAI1 expression according to the experimental process of FIG. 28.
Figure 29B:
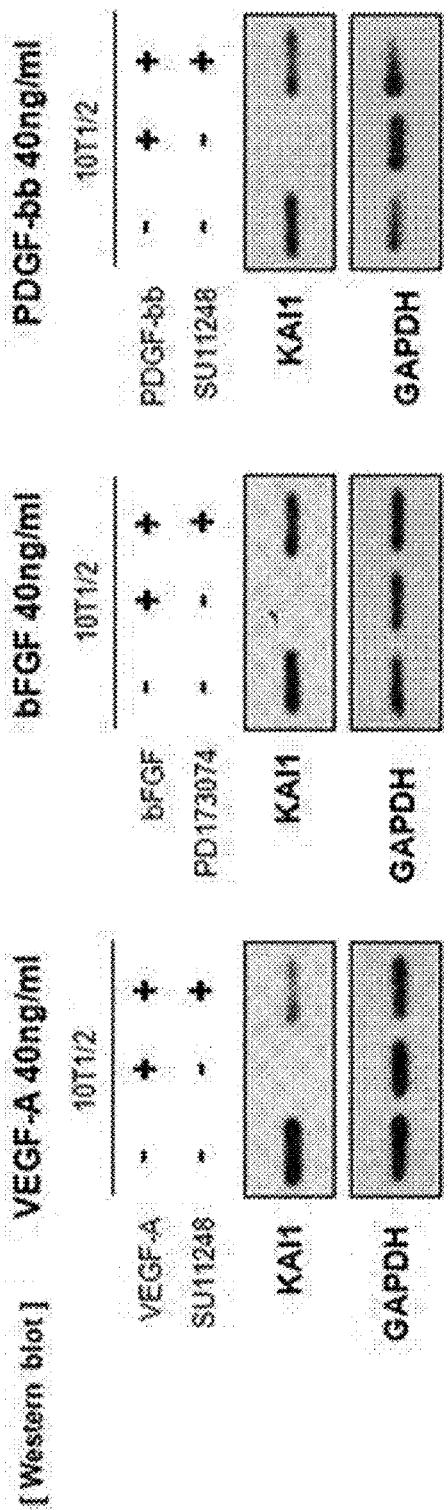

As shown in FIGS. 29A and 29B, it can be confirmed that a decreasing effect of a cytokine on the KAI1 expression of 10T1/2 was compensated by treatment using a cytokine receptor inhibitor. From the result, it can be seen that the decrease in KAI1 expression caused by a cytokine (VEGF-A, bFGF, or PDGF-bb) was a receptor-mediated response.

8-3. Confirmation of KAI1 Expression-Reduced Pattern by Cytokine Type

Figure 30:
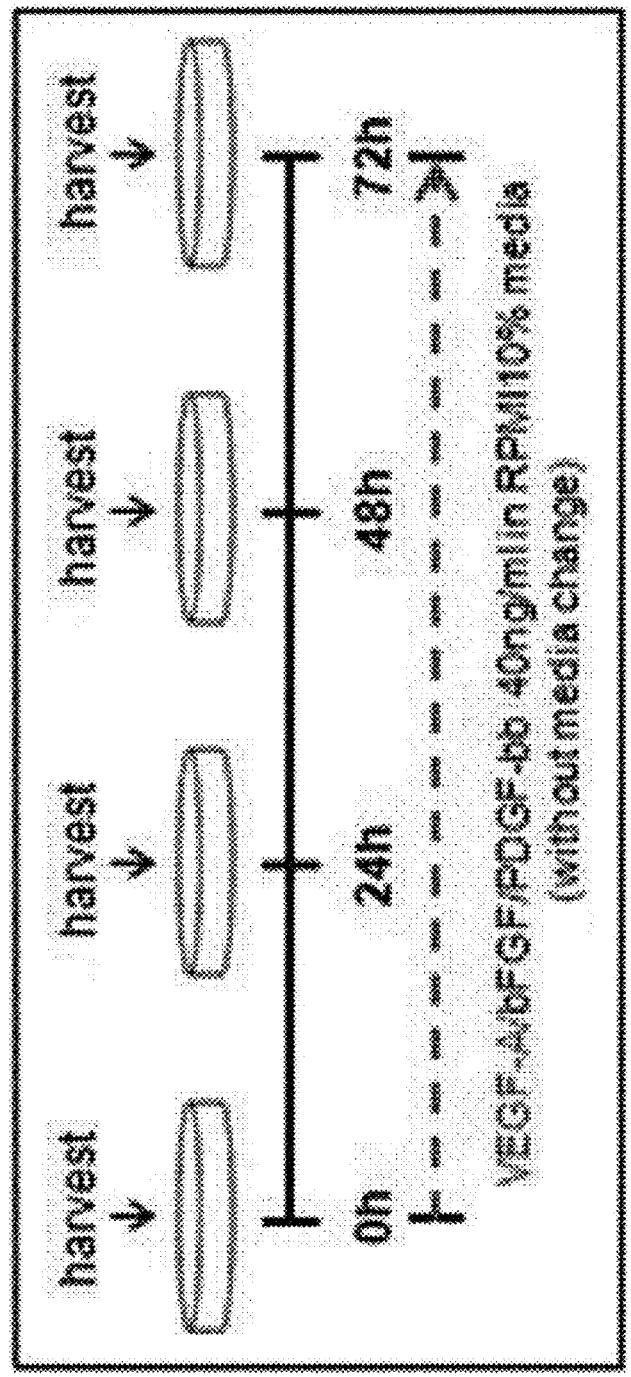
FIG. 30 shows a schematic process of an experiment to identify a KAI1 expression reduction pattern per cytokine type.

Since KAI1 expression-reduced patterns in 10T1/2 by cytokines may be different according to cytokines, to confirm this, an experiment was performed as follows, and thus a schematic process of the experiment is shown in FIG. 30.

Figure 31A:
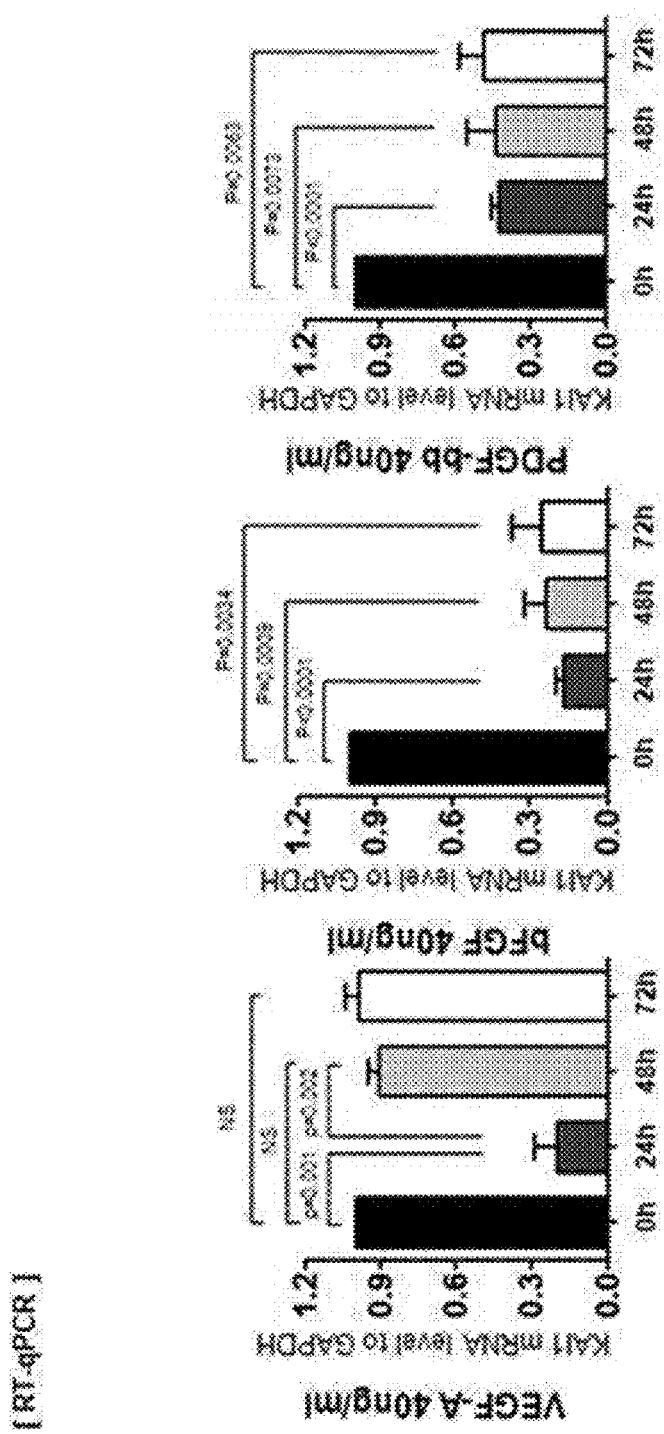
FIGS. 31A and 31B and FIG. 32 show the results of RT-qPCR, Western blotting, and immunostaining to confirm the change in KAI1 expression according to the experimental process of FIG. 30.
Figure 31B:
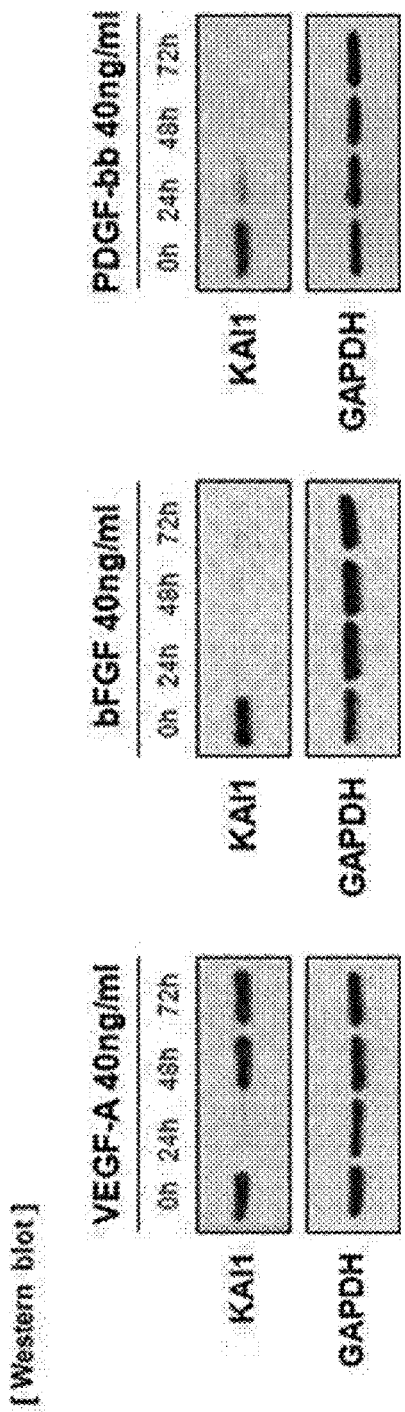
Figure 32:
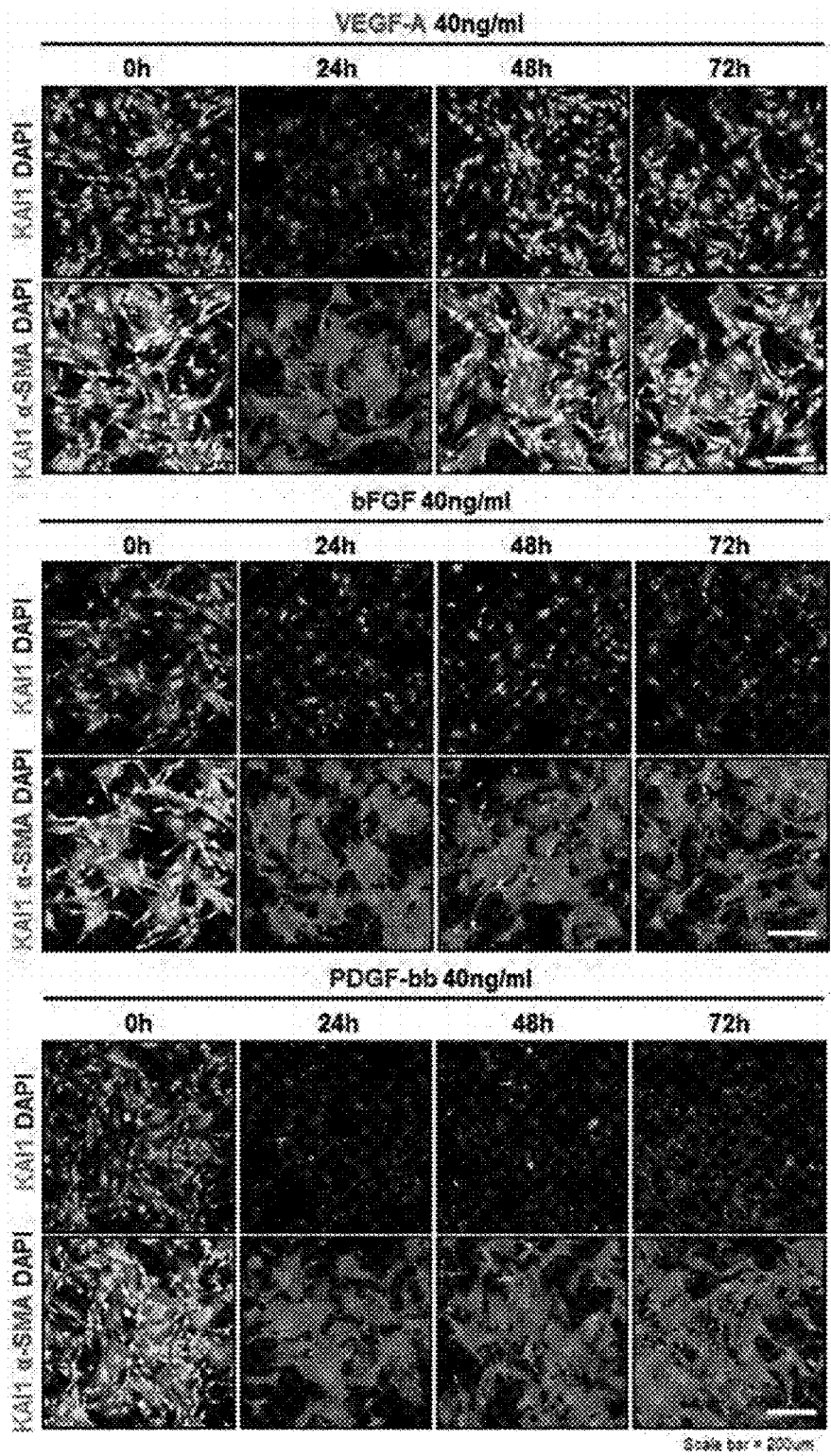

That is, the change in KAI1 expression according to time (24 hrs, 48 hrs or 72 hrs) after 10T1/2 was treated with 40 ng/ml of each cytokine (VEGF-A, bFGF or PDGF-bb) was identified through RT-qPCR, Western blotting and immunostaining, and thus the results are shown in FIGS. 31A and 31B and 32. Here, each group of 10T1/2 was treated with 40 ng/ml of each cytokine (VEGF-A, bFGF, and PDGF-bb) as an angiogenic factor and cultured in RPMI 1640 HEPES supplemented with 10% (v/v) fetal bovine serum (FBS) and 1% antibiotics-antimycotics for up to 72 hours without change in a culture medium.

As shown in FIGS. 31A and 31B and 32, it can be confirmed that KAI1 expression reduction patterns differed according to a cytokine type. More specifically, when treated with VEGF-A, KAI1 expression was temporarily decreased until 24 hours, but after 48 hours, the expression level was recovered. However, when treated with bFGF or PDGF-bb, KAI1 expression was continuously decreased until 72 hours.

8-4. Confirmation Whether Decrease in KAI1 Expression was Reversible

Figure 33:
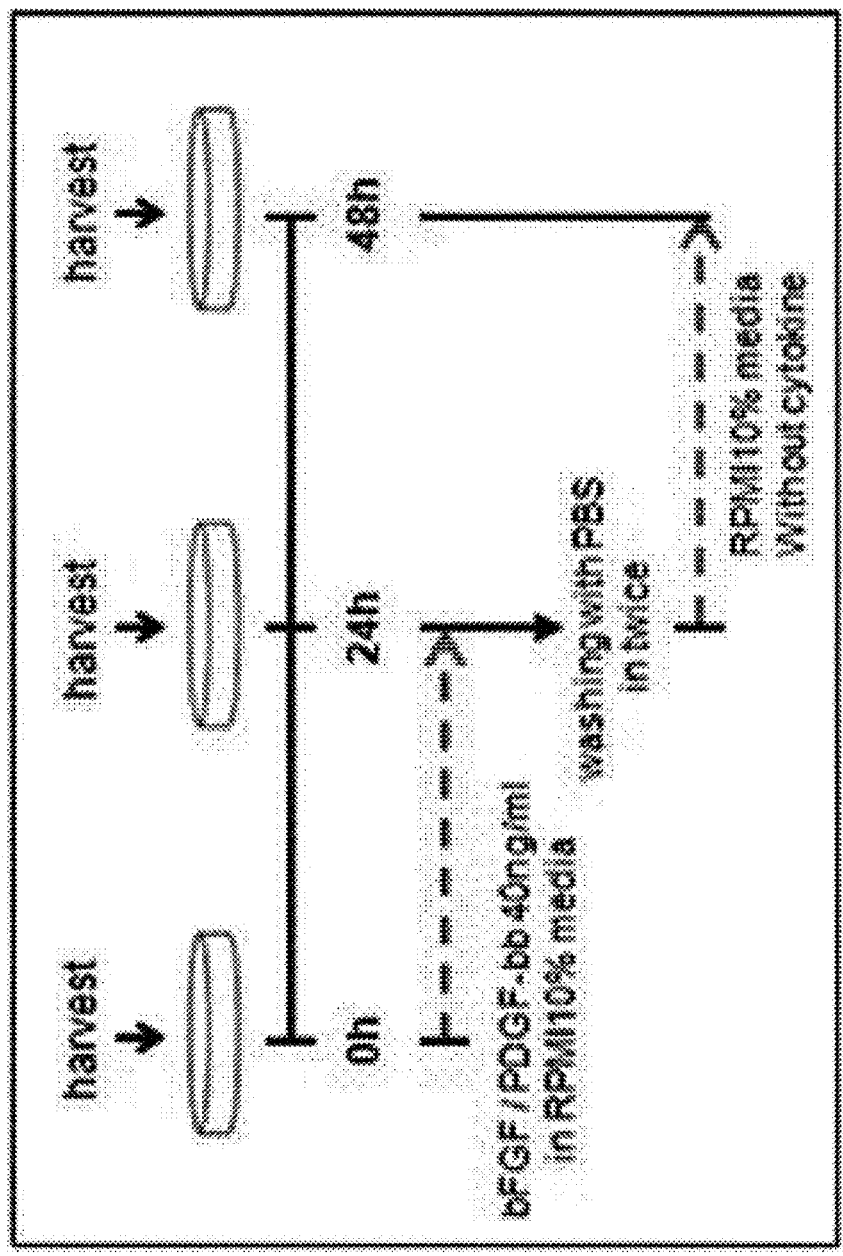
FIG. 33 shows a schematic process of an experiment to confirm whether the decrease in KAI1 expression is reversible.

While the decrease in KAI1 expression was continuously induced by FGF and PDGF stimulation to 10T1/2, to confirm whether KAI1 expression of 10T1/2 was recovered when FGF and PDGF stimulation was removed, an experiment was performed as follows, and a schematic process of the experiment is shown in FIG. 33.

Figure 34A:
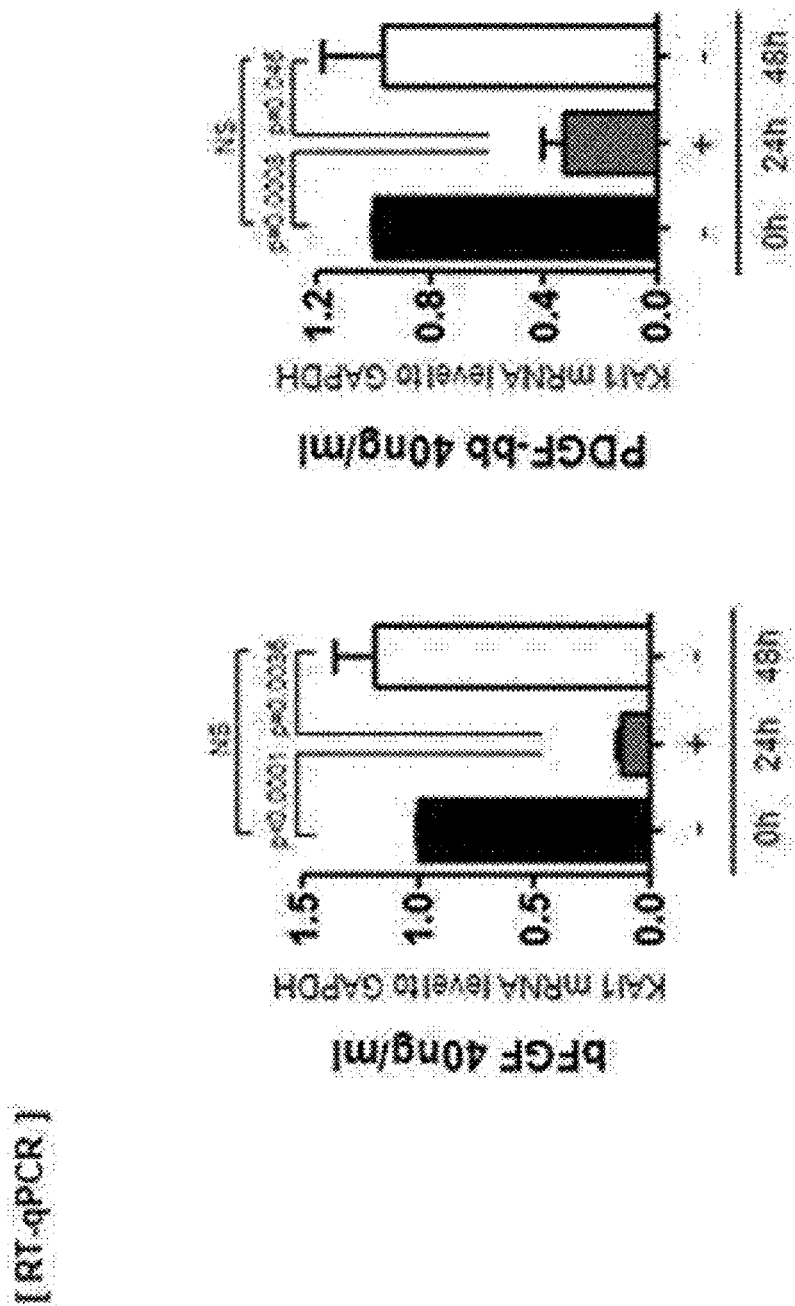
FIGS. 34A and 34B shows the results of RT-qPCR and Western blotting to confirm the change in KAI1 expression according to the experimental process of FIG. 33.
Figure 34B:
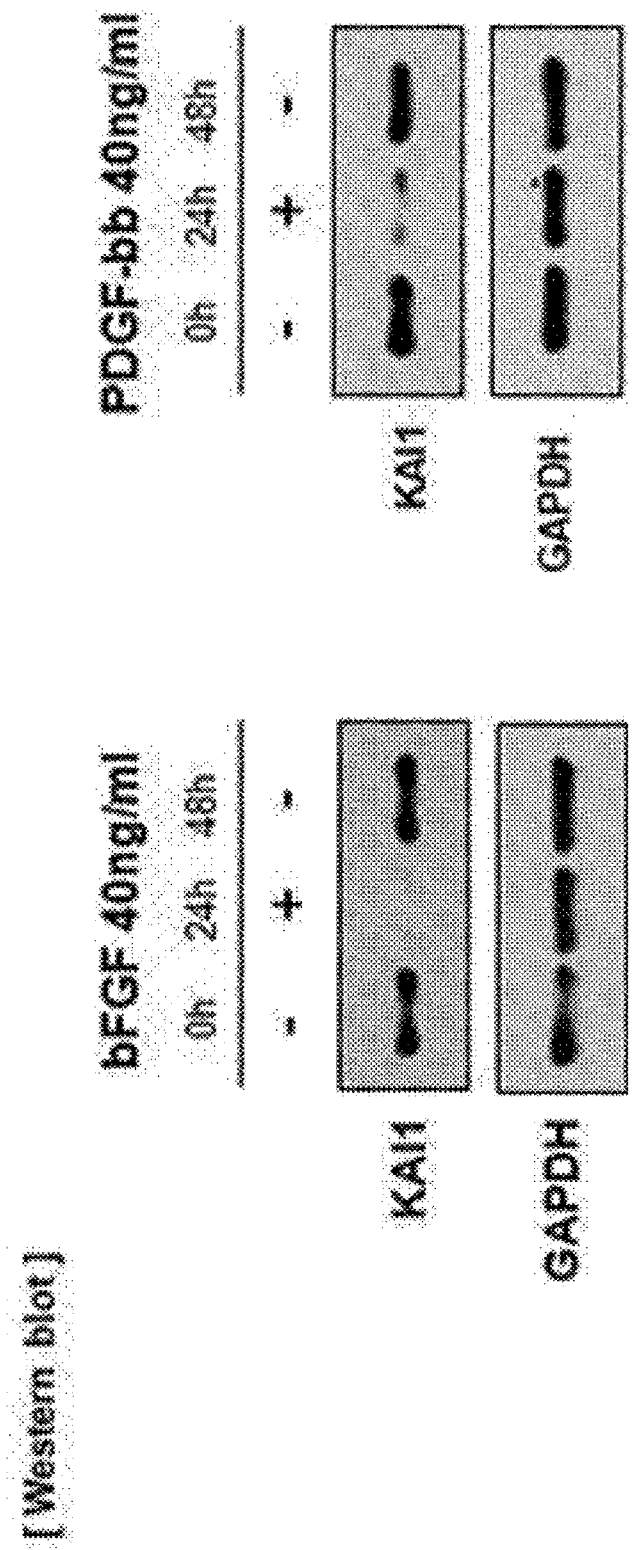
Figure 35:
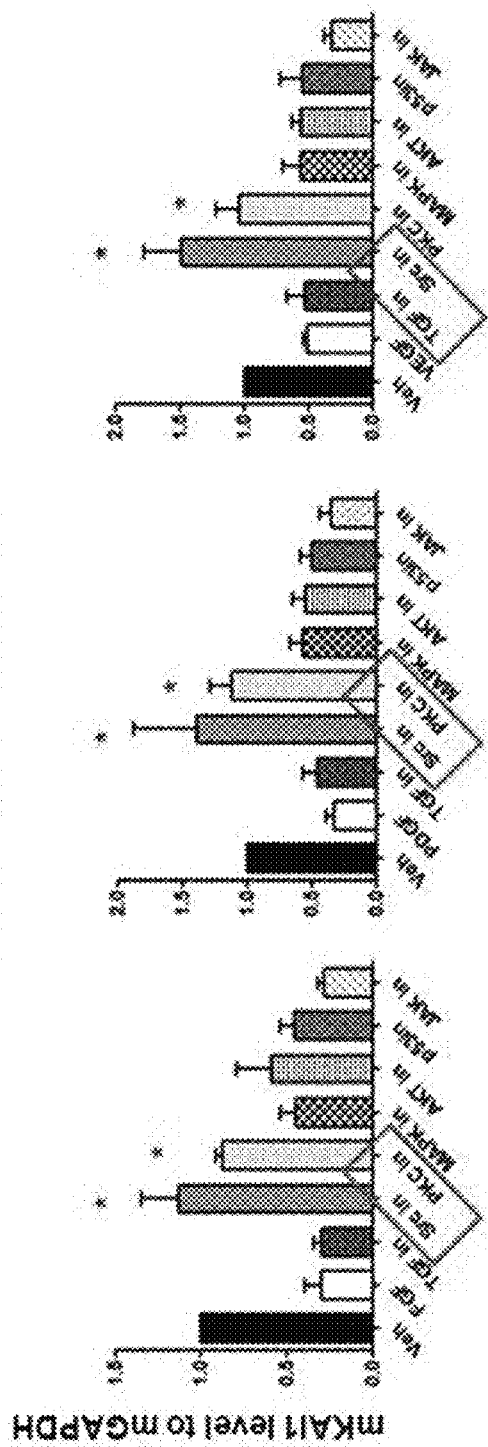
FIGS. 35 to 38 show the results of RT-qPCR and Western blotting to confirm whether the decrease in KAI1 expression in 10T1/2 due to a cytokine is blocked by treatment of signal molecule inhibitors (Src, Pkc, TGF-β, MAPK, AKT, p53, and JAK inhibitors) before cytokine stimulation to 10T1/2, to identify signaling by a cytokine for reducing KAI1 expression in 10T1/2.
Figure 36:
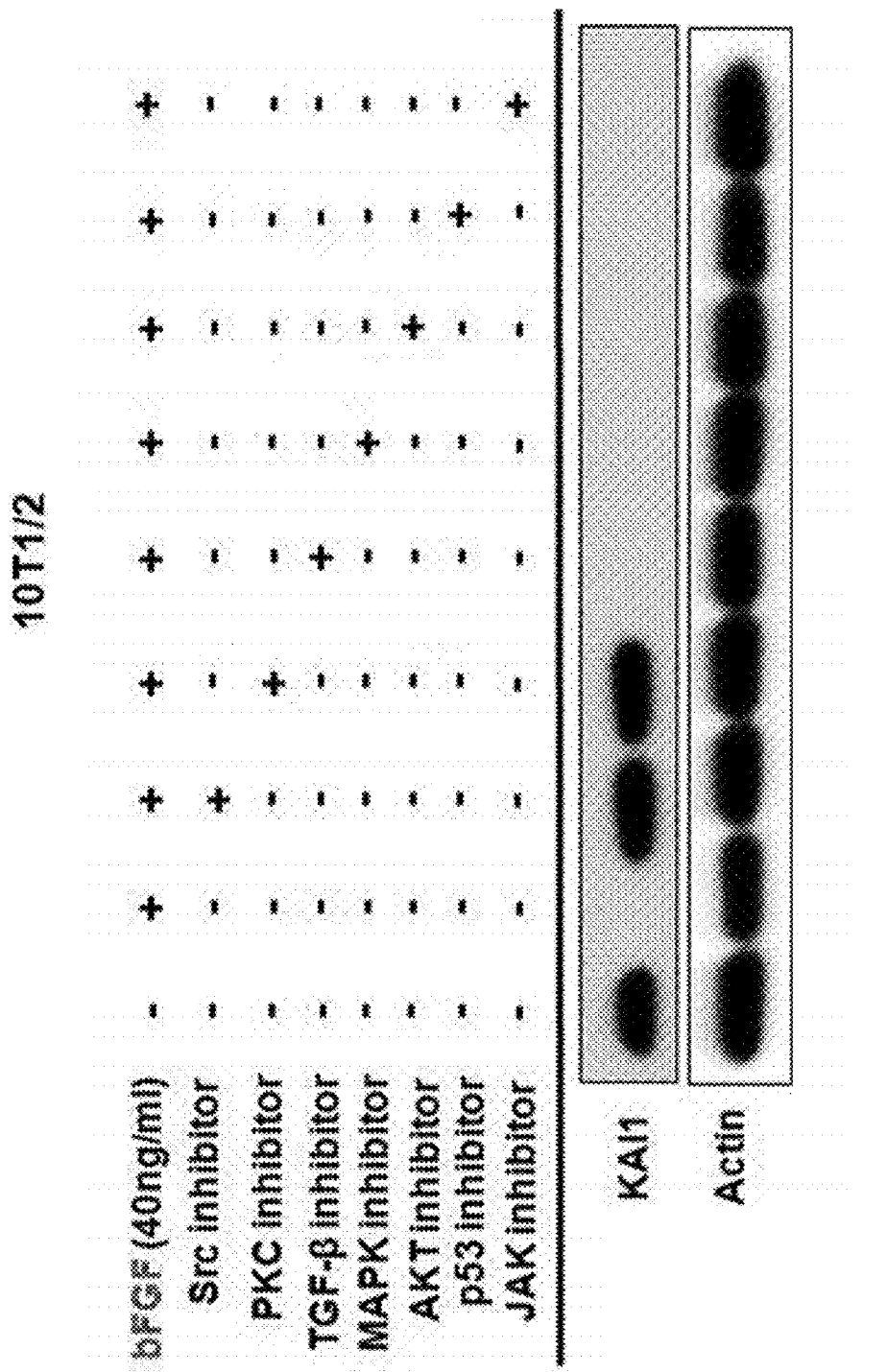
Figure 37:
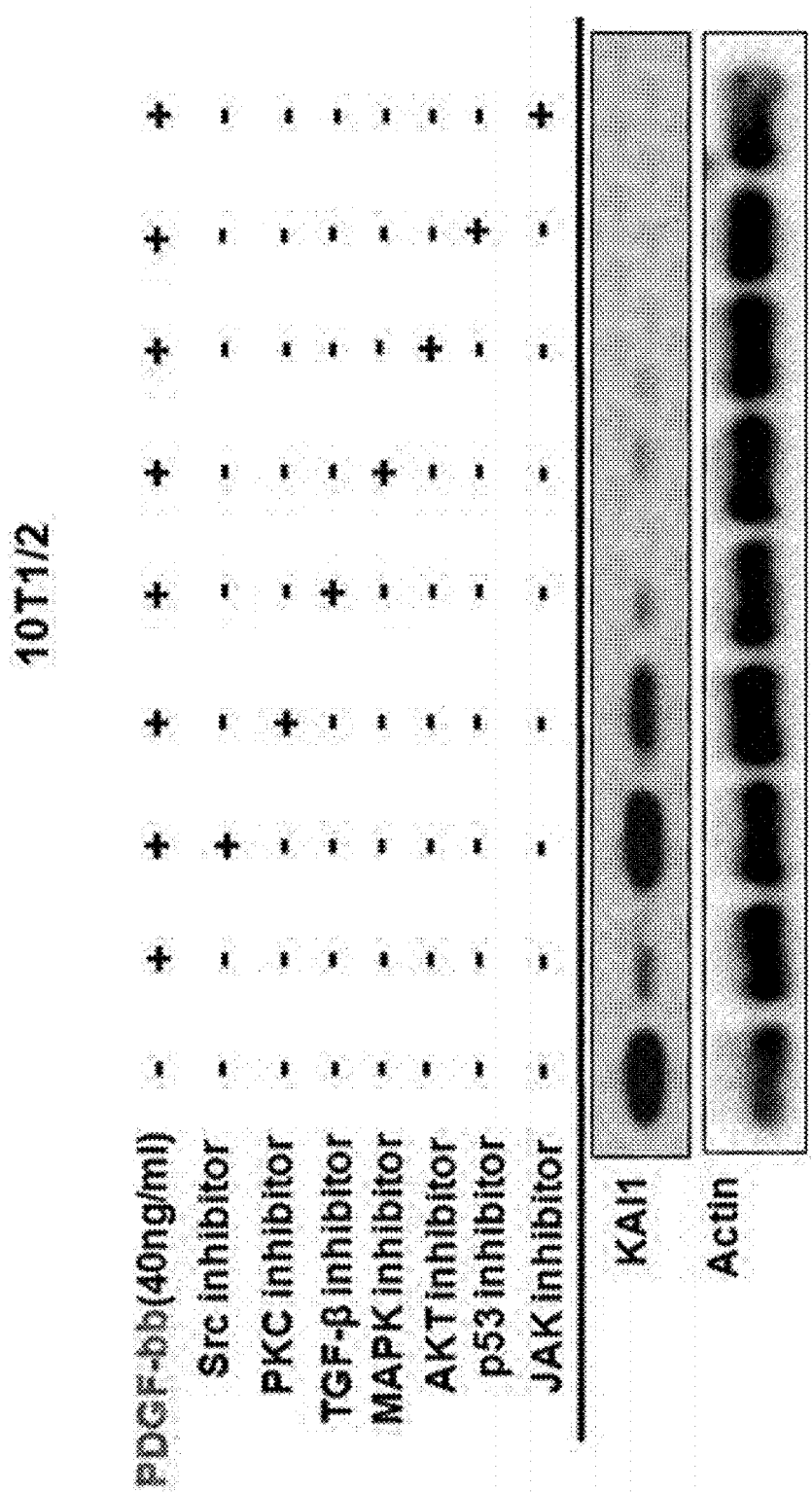
Figure 38:
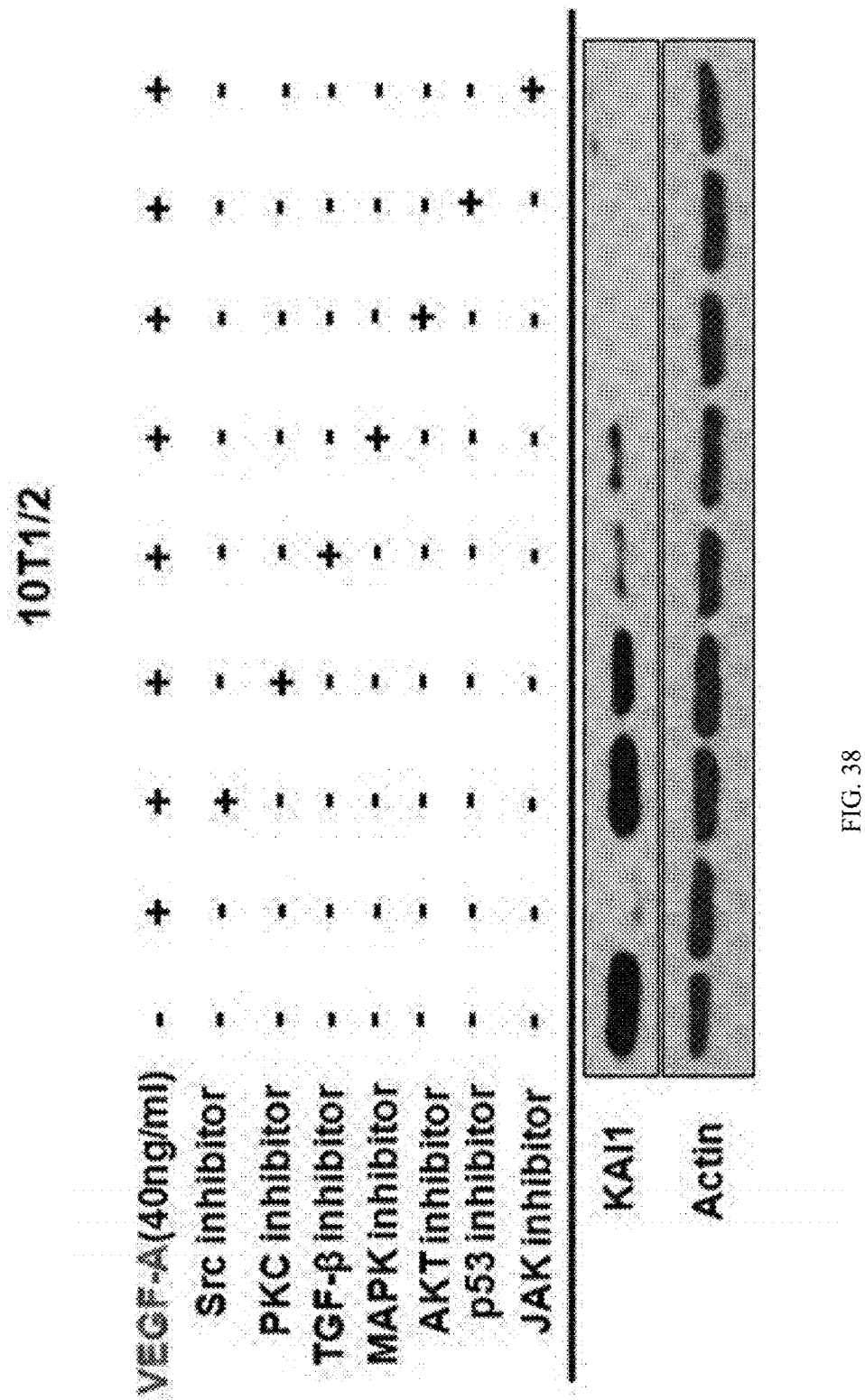

After FGF or PDGF stimulation was given to 10T1/2, 24 hours later, the media was changed with fresh culture media (general culture media), and then RT-qPCR and Western blotting were conducted to confirm whether there was a change in the decreased expression of KAI1. The result is shown in FIGS. 34A and 34B. As shown in FIGS. 34A and 34B, after 10T1/2 was stimulated with both FGF and PDGF for 24 hours, and the stimulant was then removed, thereby confirming that KAI1 expression was recovered again. From the result, it can be seen that the decrease in KAI1 expression was reversible.

8-5. Confirmation of Signaling of Decrease in KAI1 Expression by Cytokine

To confirm signaling of the decrease in KAI1 expression in 10T1/2 by a cytokine, RT-qPCR and Western blotting were used to confirm whether the decrease in KAI1 expression in 10T1/2 by a cytokine was blocked by treating 10T1/2 with a signal molecule inhibitor (a Src, Pkc, TGF-β, MAPK, AKT, p53. or JAK inhibitor) before cytokine stimulation, and the result is shown in FIGS. 35 to 38.

As shown in FIGS. 35 to 38, it can be confirmed that the decreases in KAI1 expression caused by the cytokines (VEGF-A, bFGF, and PDGF-bb) were blocked in the groups treated with Src and Pkc inhibitors. From the result, it can be seen that KAI1 expression in 10T1/2 by a cytokine was decreased via Src or Pkc signaling.

Figure 39:
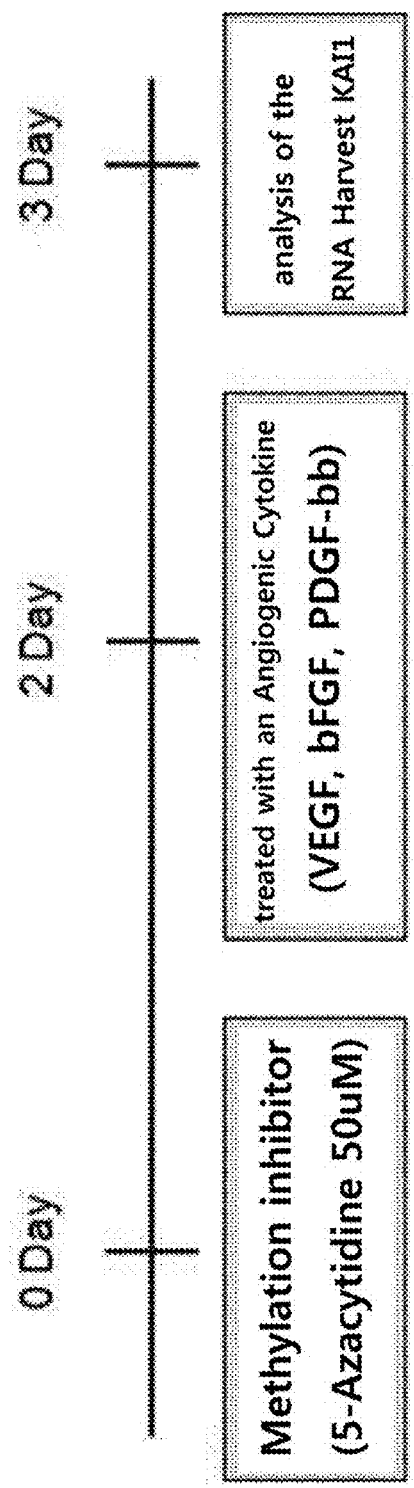
FIG. 39 shows a schematic process of an experiment to confirm a mechanism for inhibiting KAI1 at a gene level.

Example 9. Identification of Mechanism for Reducing KAI1 Expression 9-1. Identification at Gene Level To identify a mechanism for inhibiting KAI1 at a gene level, an experiment was performed as follows, and a schematic process of the experiment is shown in FIG. 39.

10T1/2 was treated with 50 µM of a methylation inhibitor (5-azacytidine), and then treated with each cytokine (VEGF-A, bFGF, and PDGF-bb), which is an angiogenic factor, to confirm KAI1 expression, and the result is shown in FIG. 40. As shown in FIG. 40, when 10T1/2 was treated with a methylation inhibitor as well as an angiogenic factor, it can be confirmed that KAI1 gene expression was not decreased.

Figure 41:
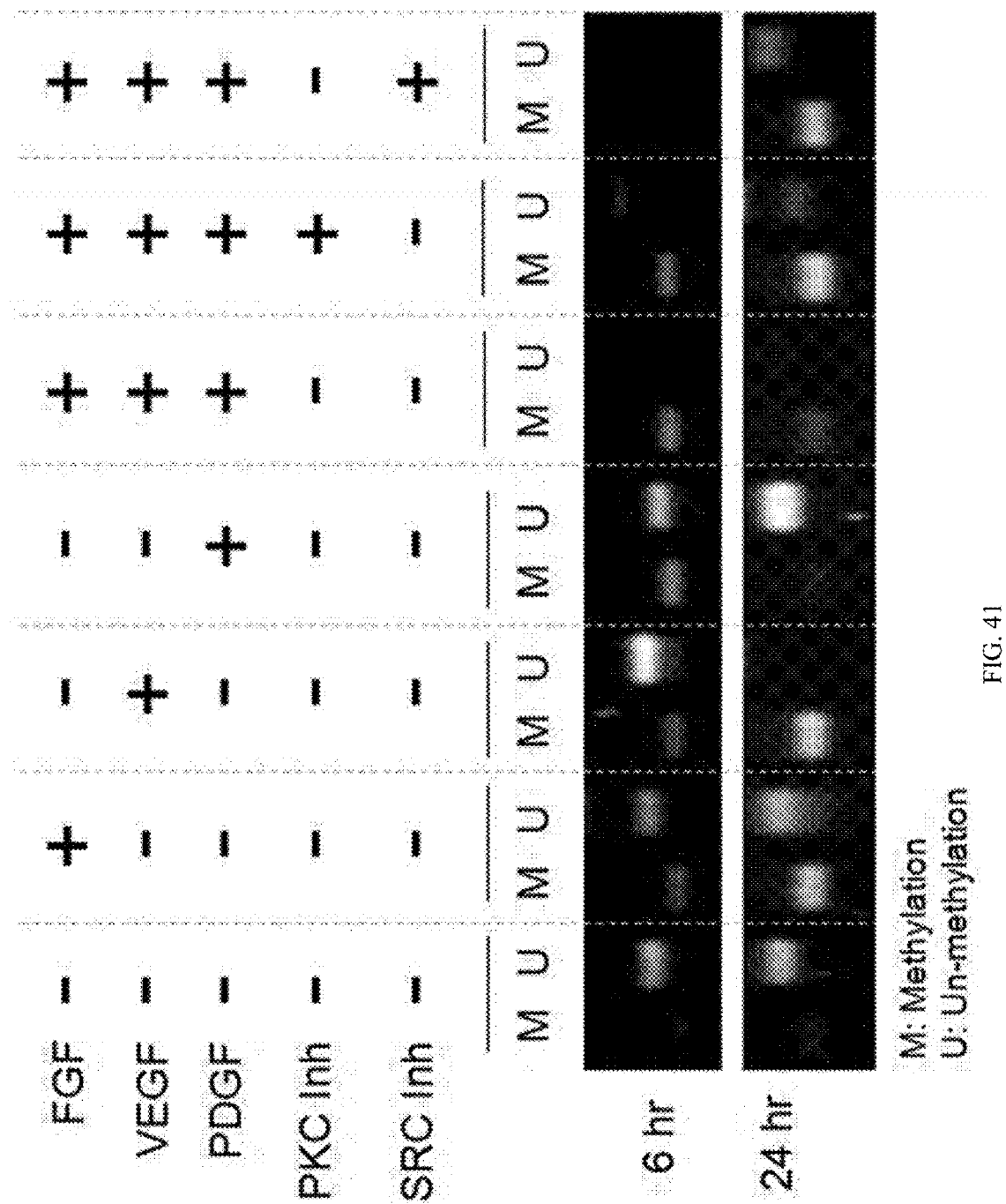
FIG. 41 shows the result of bisulfite sequencing to confirm whether methylation of CpG islands in KAI1 promoter is increased due to an angiogenic factor.
Figure 42:
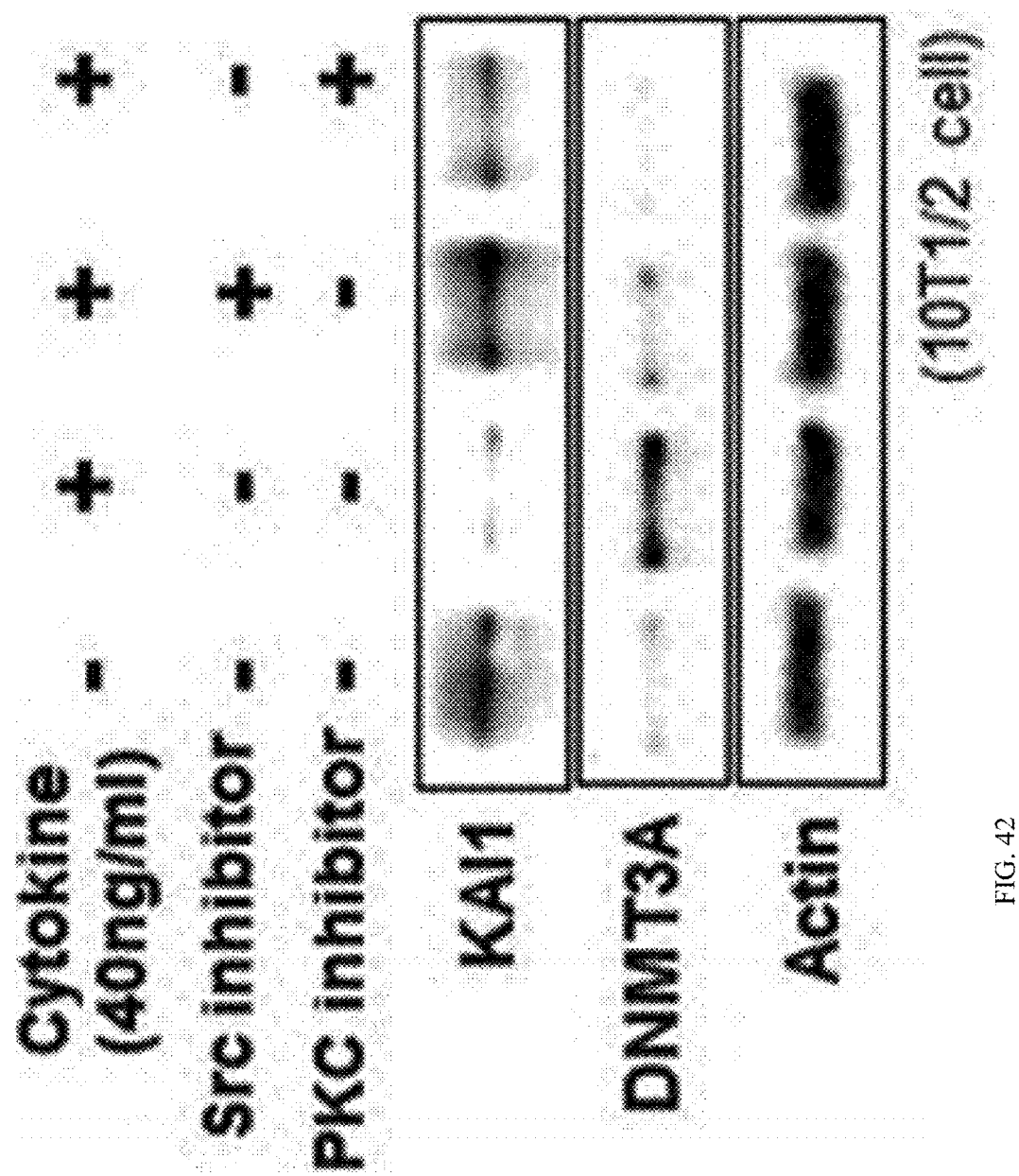
FIG. 42 shows the result of Western blotting to confirm that expression of DNA methyltransferase 3a (DNMT3a) is increased.
Figure 43:
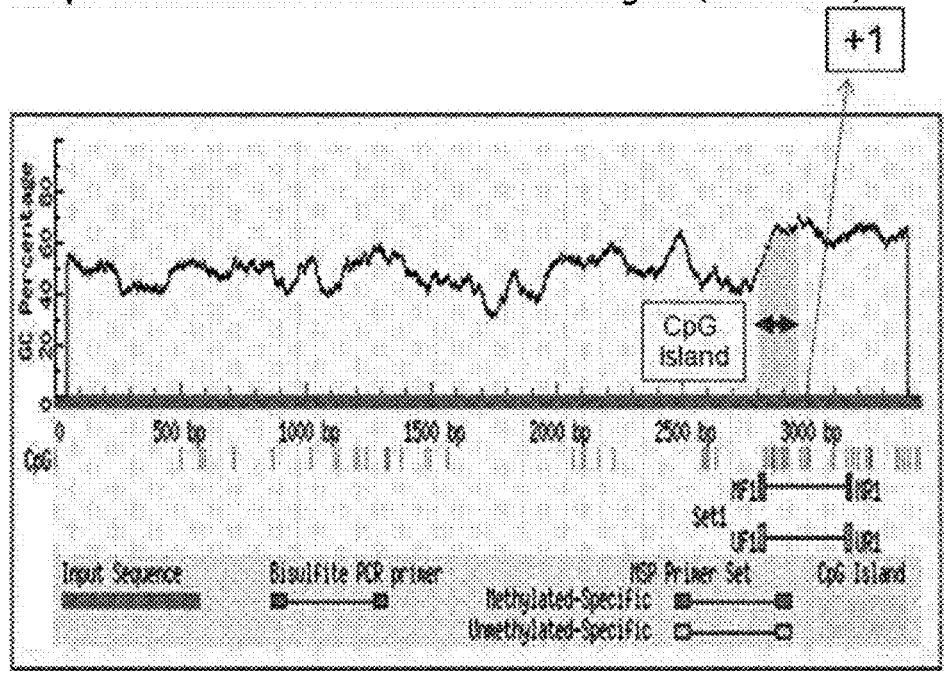
FIG. 43 schematically shows CpG islands in a mouse KAI1 promoter region.

In addition, bisulfite sequencing was performed to confirm whether the methylation of CpG islands present in a KAI1 promoter was increased by an angiogenic factor, and Western blotting was performed to confirm that the expression of DNA methyltransferase 3a (DNMT3a) was increased, and the results are shown in FIGS. 41 and 42.

As shown in FIGS. 41 and 42, it can be confirmed that the methylation of CpG islands present in the KAI1 promoter and DNMT3a were increased by an angiogenic factor.

From the result, it can be seen that the mechanism for inhibiting KAI1 at a gene level was CpG island methylation due to the increase in DNA methyltransferase 3a (DNMT3a) via Src or Pkc.

Example 10. Verification of Inhibiting Angiogenesis by KAI1 Expression

Figure 44:
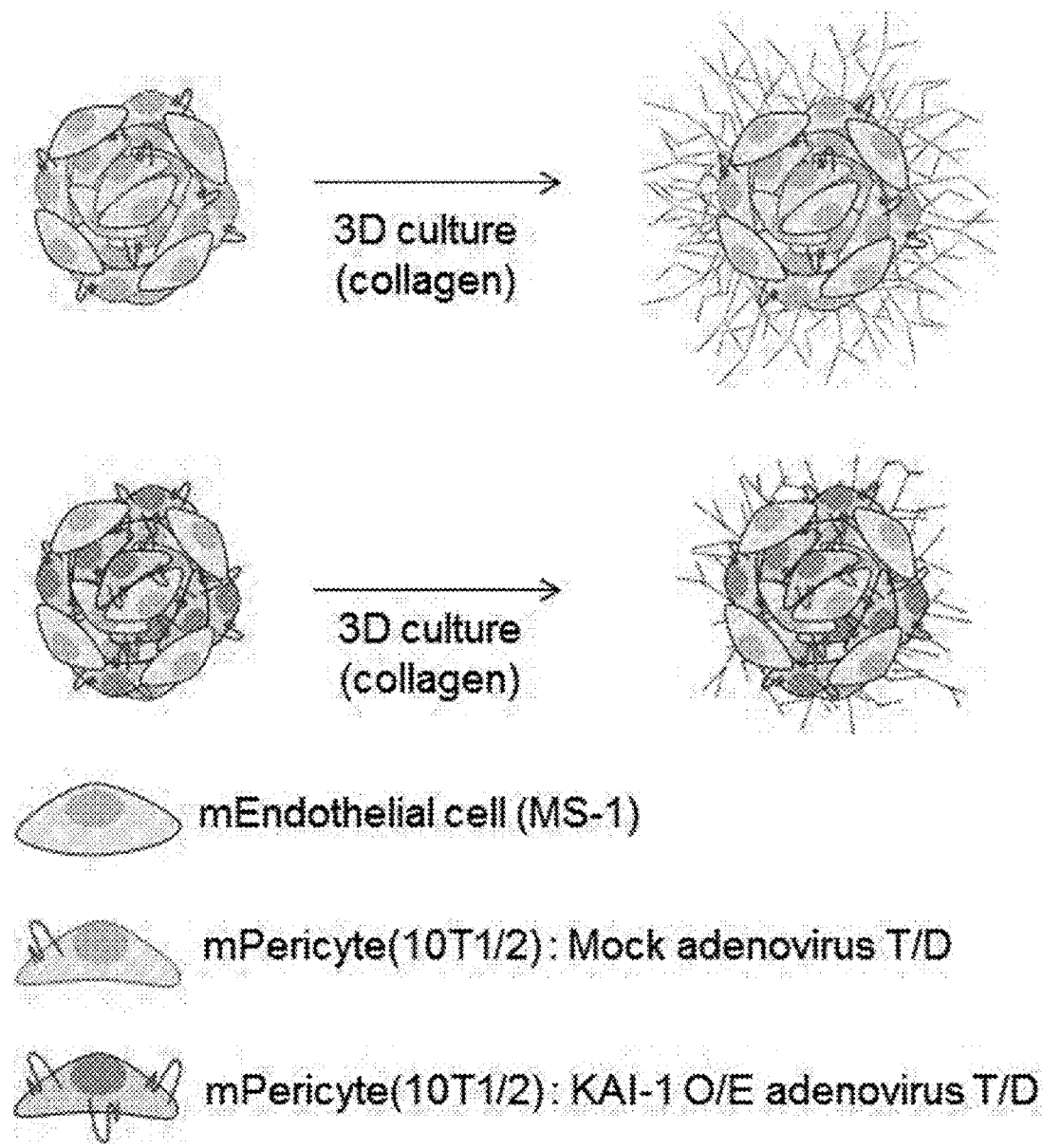
FIG. 44 shows a schematic process of an experiment to verify an angiogenesis inhibitory effect due to KAI1 expression.

To verify an angiogenesis inhibitory effect by KAI1 expression, an experiment was performed as follows, and a schematic process of the experiment is shown in FIG. 44.

Figure 46:
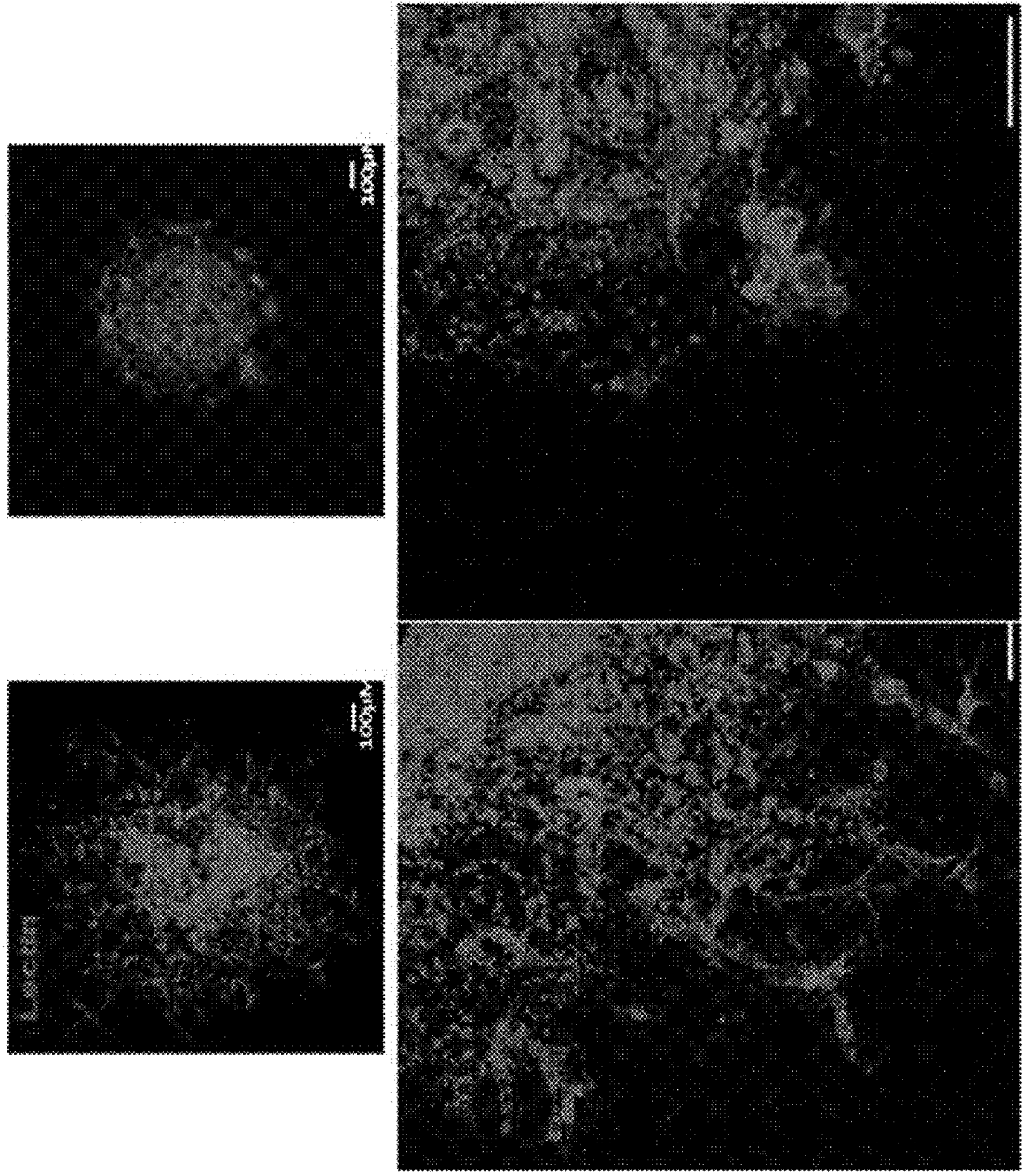

As shown in FIG. 44, to quantify a degree of vessel formation, a EC-pericyte hybrid spheroid was manufactured and embedded in collagen, and then a degree of vessel formation was observed over time. Here, a mouse endothelial cell line (MS-1) was used as ECs and 10T1/2 was used as pericytes. In addition, KAI1 was overexpressed using an adenovirus in pericytes. In the manufacture of the spheroid, a ratio of the number of each type of cell (EC:pericyte) was 2:1, and the total cell number was fixed at $3\times10^3$. As culture media used to grow the spheroids, 10% FBS and 1% antibiotics-antimycotics-containing Dulbecco's modified eagle medium (DMEM) was used. In addition, effective EC sprouting was induced by a treatment of 100 ng/ml of recombinant human VEGF. As a result, as shown in FIGS. 45 and 46, it can be confirmed that sprouting was inhibited in spheroids containing KAI1-overexpressed pericytes in which KAI1 was overexpressed by a KAI1 adenovirus (control: pericytes transduced with mock adenovirus).

Figure 47A:
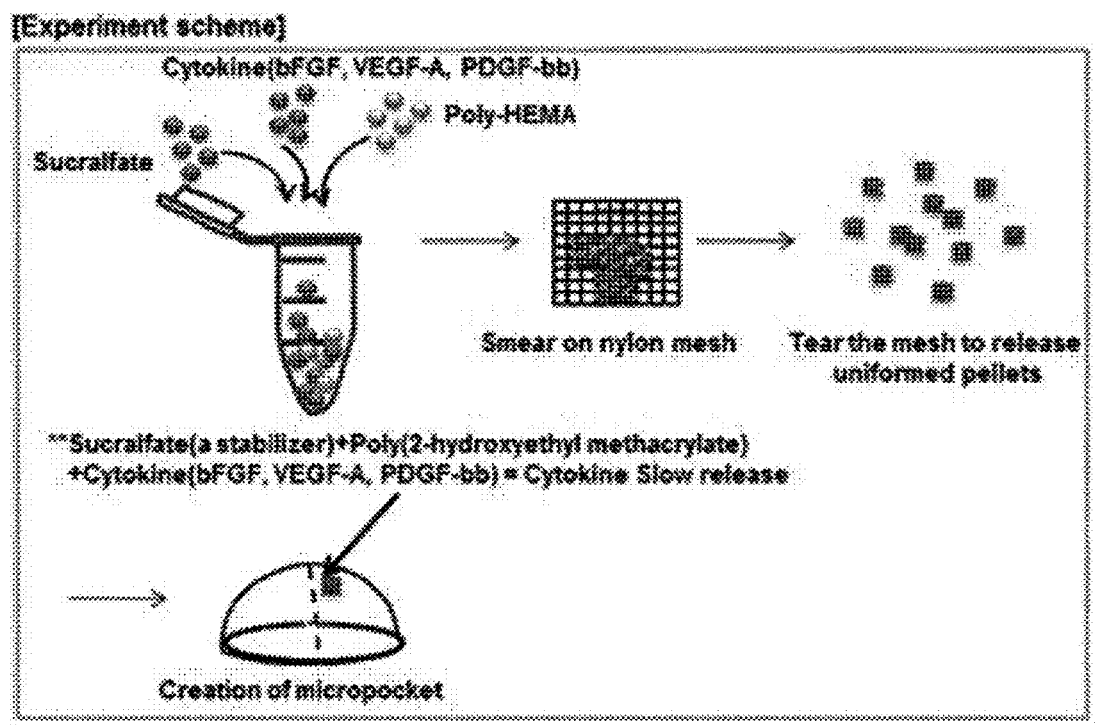
FIGS. 47A and 47B show the result of a mouse cornea micropocket assay to confirm whether angiogenesis is actually regulated by regulating KAI1 expression of a pericyte in vivo.
Figure 47B:
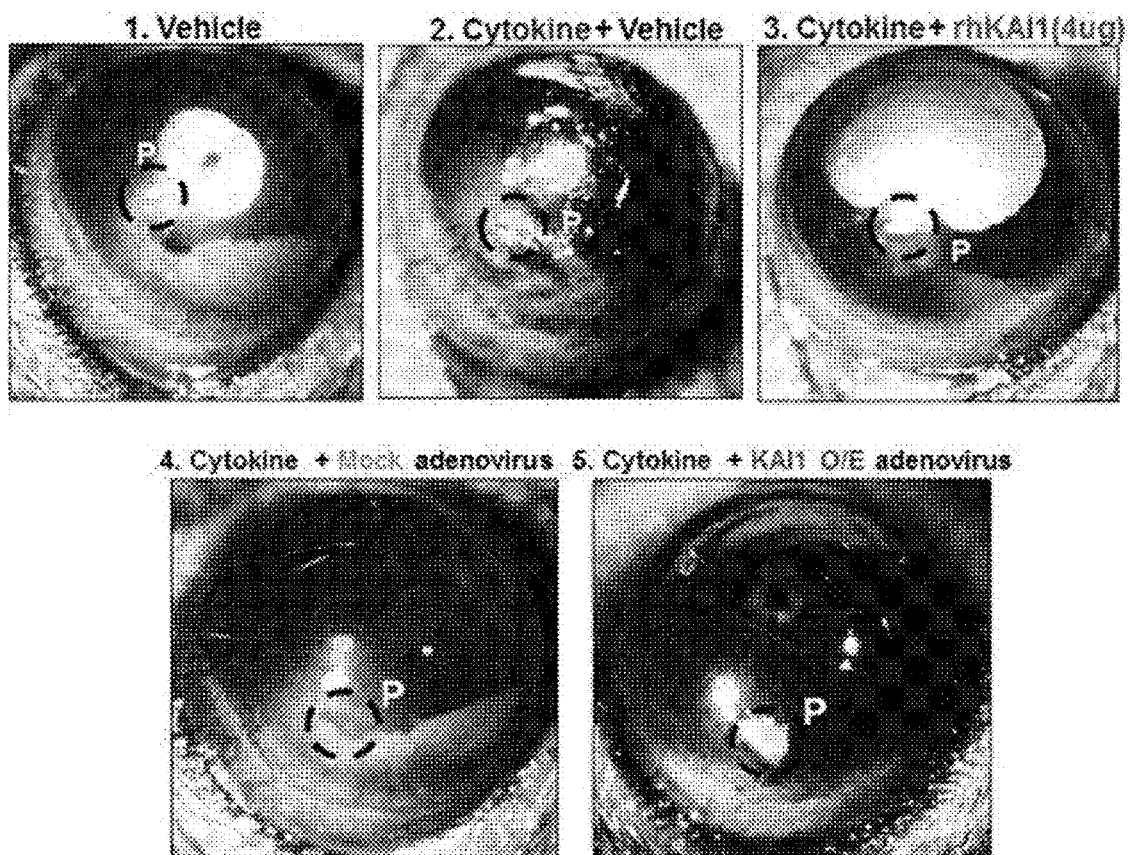

Based on the above-described in vitro experiment, a mouse cornea micropocket assay was performed to confirm whether angiogenesis was actually regulated by in vivo regulation of the KAI1 expression of pericytes. After a pocket formed by mixing cytokine, sucralfate and polyhema (from which the cytokine was slowly secreted little by little) was manufactured and added to the mouse cornea, a degree of angiogenesis per experimental group was examined for 10 days. As a result, as shown in FIGS. 47A and 47B, it can be confirmed that, compared to a vehicle, angiogenesis in the mouse cornea injected with a pellet containing only a cytokine was added was much increased. However, it can be confirmed that there was no angiogenesis in the mouse cornea injected with a pellet containing both cytokine and a recombinant KAI1 protein, similar to that of the vehicle. It can be confirmed that, in a KAI1 adenovirus-injected group, compared to a mock adenovirus-injected group, there was much less angiogenesis.

Example 11. Confirmation of Tumor Growth Inhibitory Effect of KAI1-Expressed Pericytes To confirm an effect of the KAI1 expression of pericytes on tumor growth, an experiment was performed as follows.

Figure 48A:
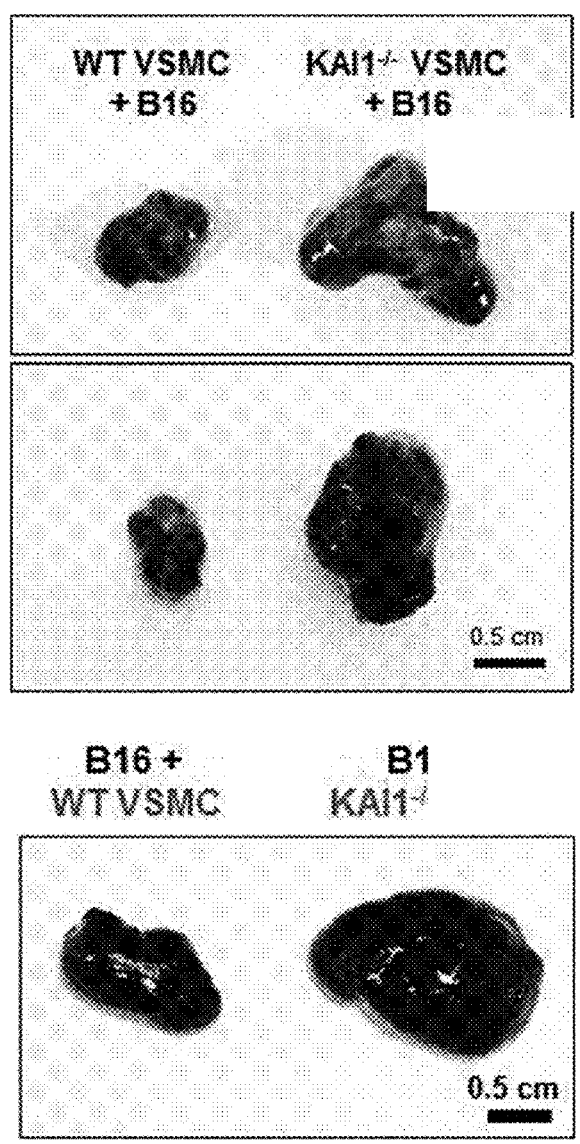
FIGS. 48A and 48B show the result of comparing tumor weights and volumes measured after a mouse melanoma cell line of B16, WT, or KAI1$^{-/-}$ mVSMC is mixed with a matrigel and transplanted into a dorsal area of a C57 mouse to confirm a tumor growth inhibitory effect of a KAI1-expressed pericyte.
Figure 48B:
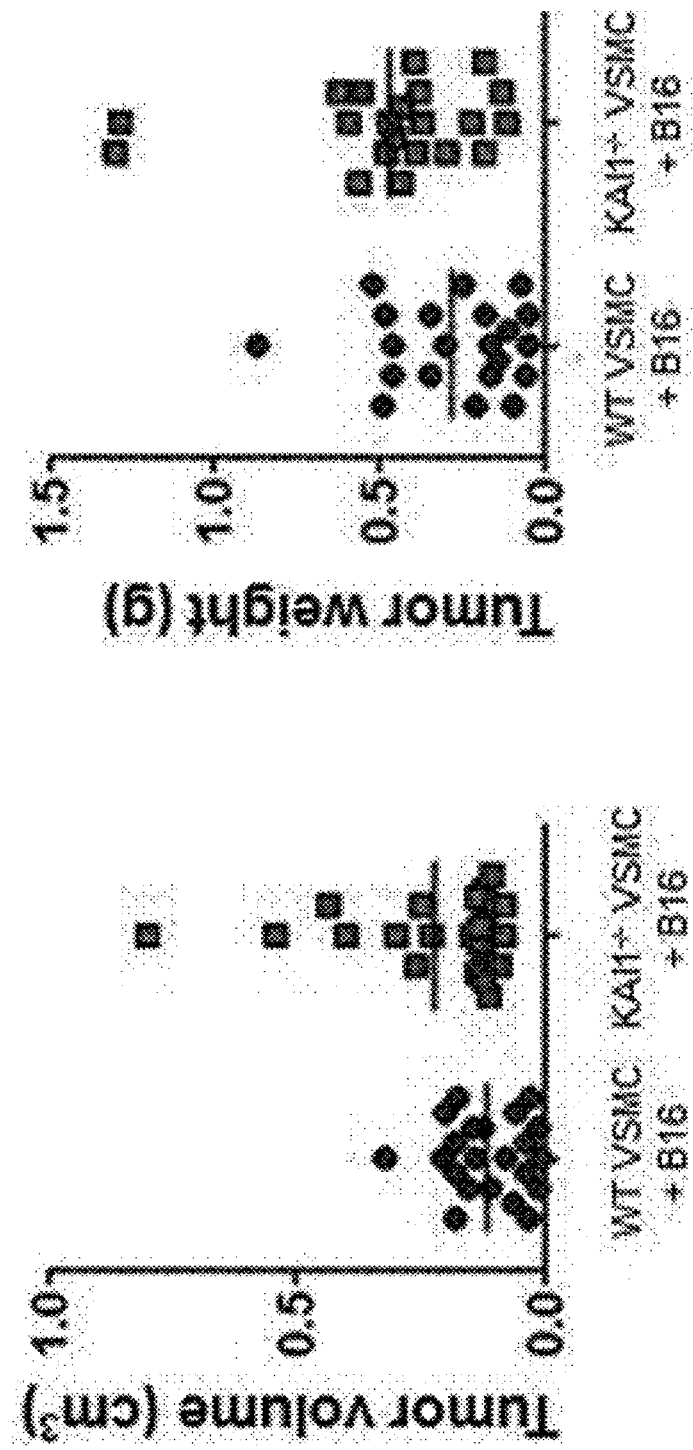

First, after a mouse melanoma cell line B16 and WT or KAI1$^{-/-}$ mVSMC were mixed with a matrigel and transplanted into the dorsal area of a C57 mouse, tumor weight and volume were measured and compared, and the result is shown in FIGS. 48A and 48B. As shown in FIGS. 48A and 48B, it can be confirmed that there was considerably less tumor growth in the WT mVSMC and B16-added group than in the KAI1$^{-/-}$ mVSMC and B16-added group.

Subsequently, a human tissue sample was collected, and an experiment for comparing KAI1 expression patterns in vascular pericytes of normal tissue and tumor tissue was conducted. Specifically, KAI1(488) and SMA(555) were stained with antibodies and compared through confocal images. As a result, as shown in FIG. 49, it can be confirmed that KAI1 expression in tumor tissue pericytes were lower than that of normal tissue pericytes.

Figure 50A:
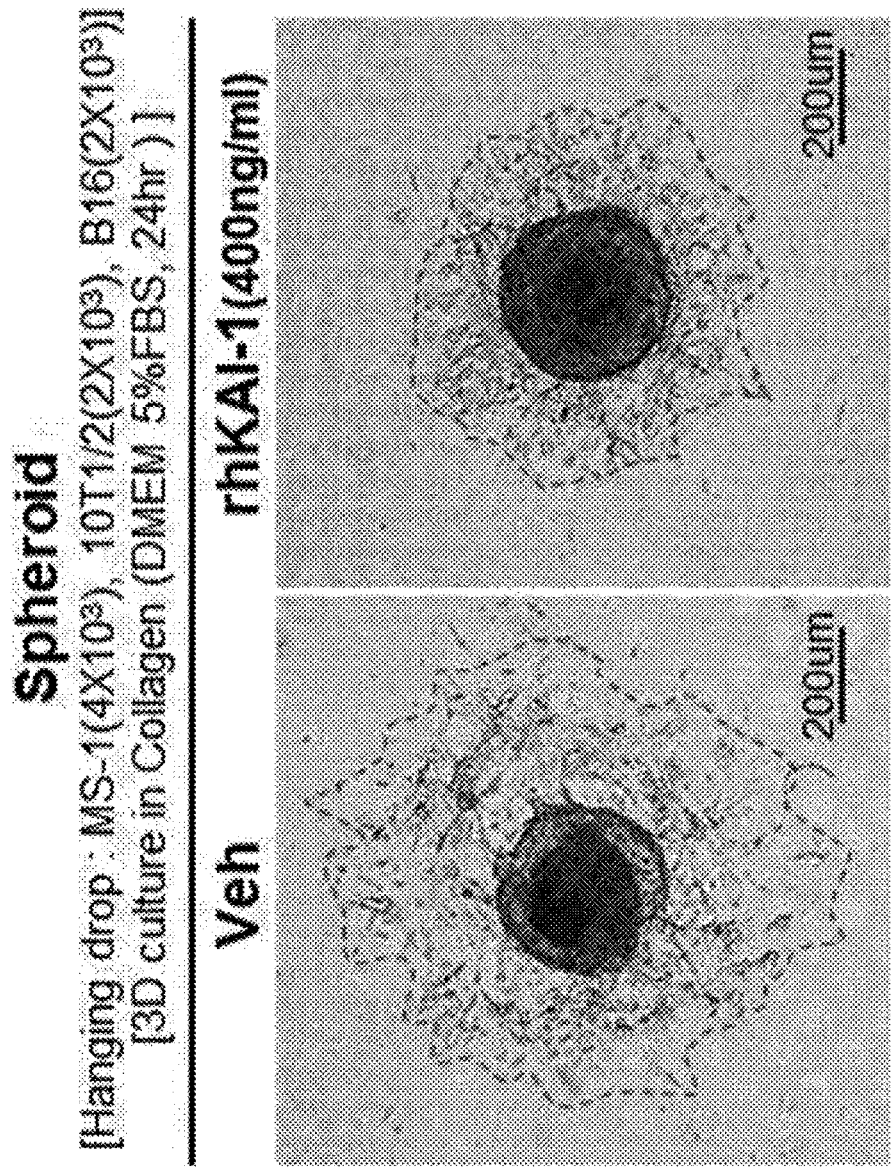
FIGS. 50A and 50B and FIG. 51 show the results of observing a degree of vascular development over time after B16 and an EC-pericyte hybrid spheroid are manufactured and embedded in collagen to verify an anticancer effect of treatment of KAI1 protein.
Figure 50B:
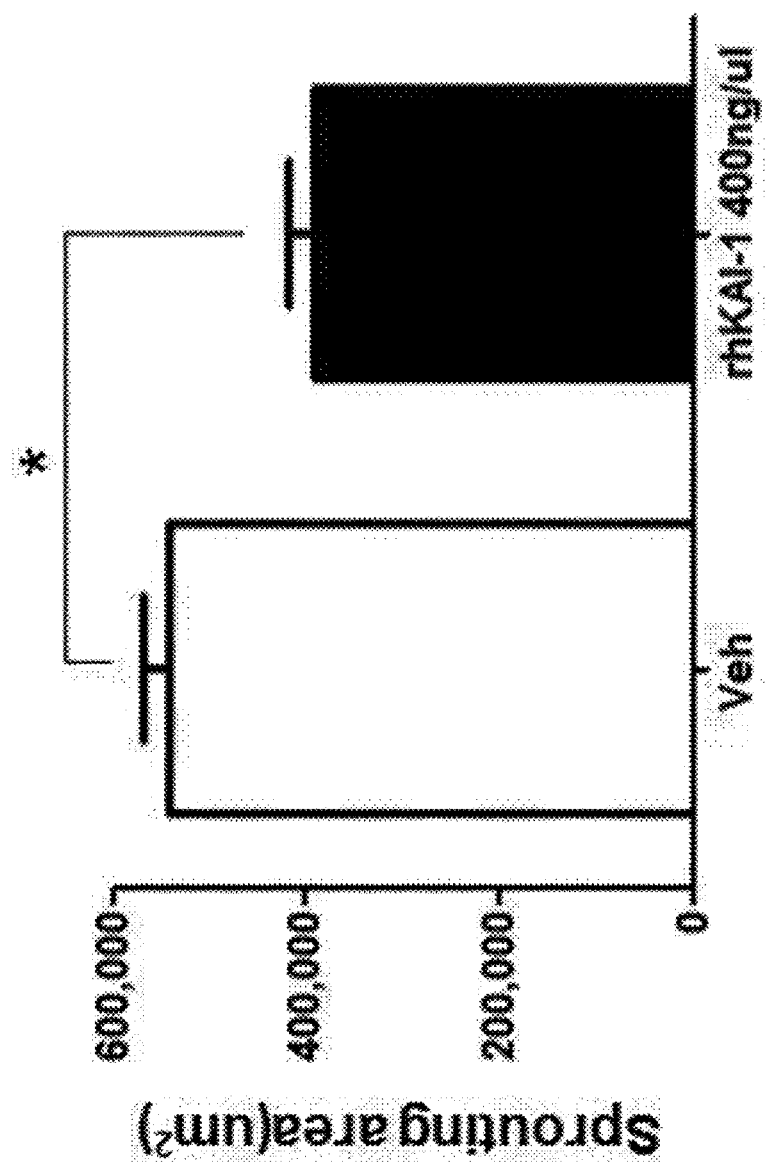
Figure 51:
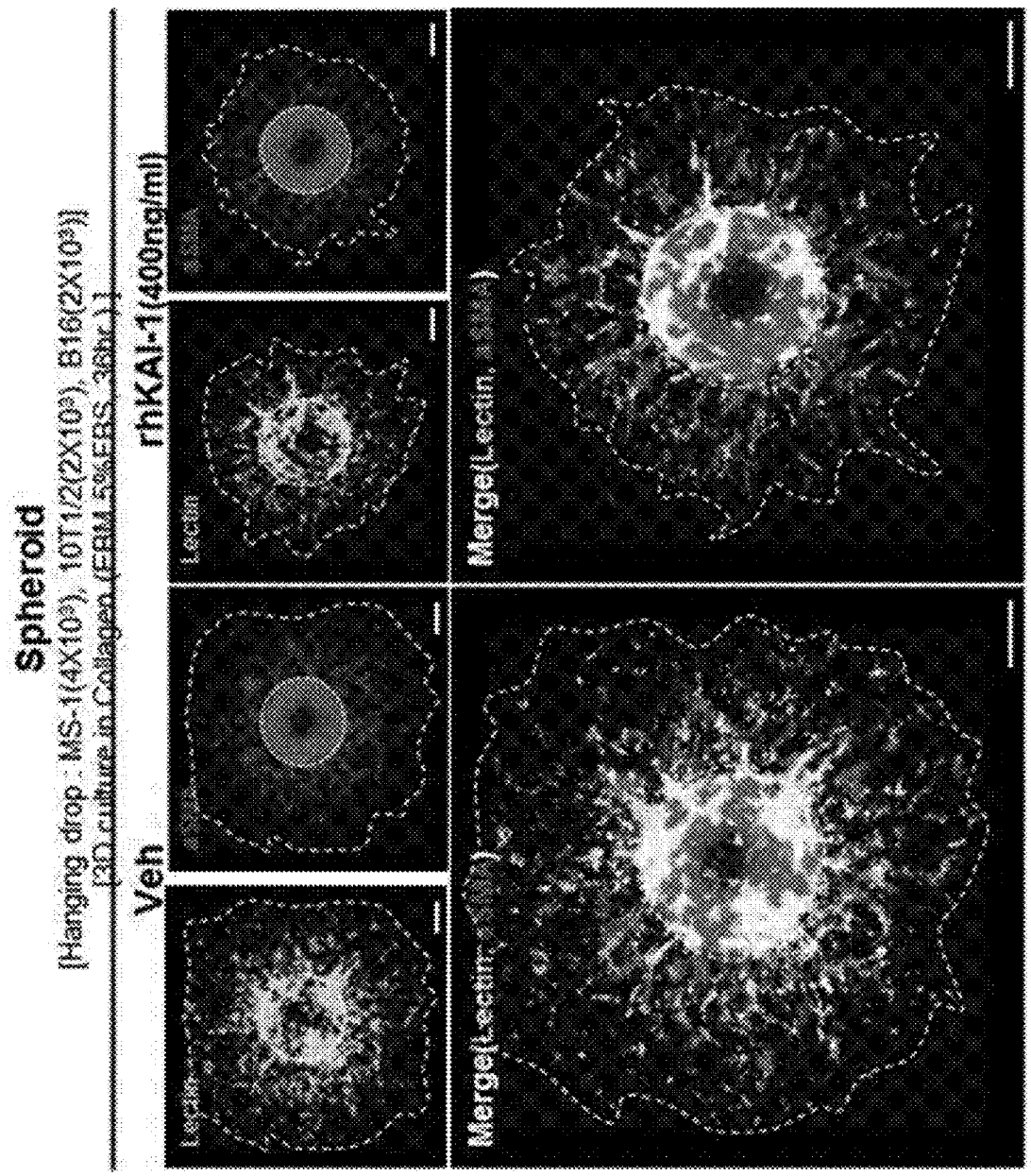

Afterwards, to verify an anticancer effect of a KAI1 protein treatment, B16 and an EC-pericyte hybrid spheroid were manufactured and embedded in collagen, and then a degree of vessel formation was observed by time. Here, a mouse endothelial cell line (MS-1) was used as ECs, and 10T1/2 was used as pericytes. In the manufacture of the spheroid, a ratio of the number of each type of cell (EC: pericyte) was 2:1, and the total cell number was fixed at $3\times10^3$. As culture media used to grow the spheroids, Dulbecco's modified eagle medium (DMEM) supplemented with 10% FBS and 1% antibiotics-antimycotics and a KAI1 protein was used. As a result, as shown in FIGS. 50A and 50B and 51, it can be confirmed that the sprouting of the KAI1 protein was inhibited in the spheroids. Therefore, an anticancer effect of the KAI1 protein was able to be expected.

Figure 52:
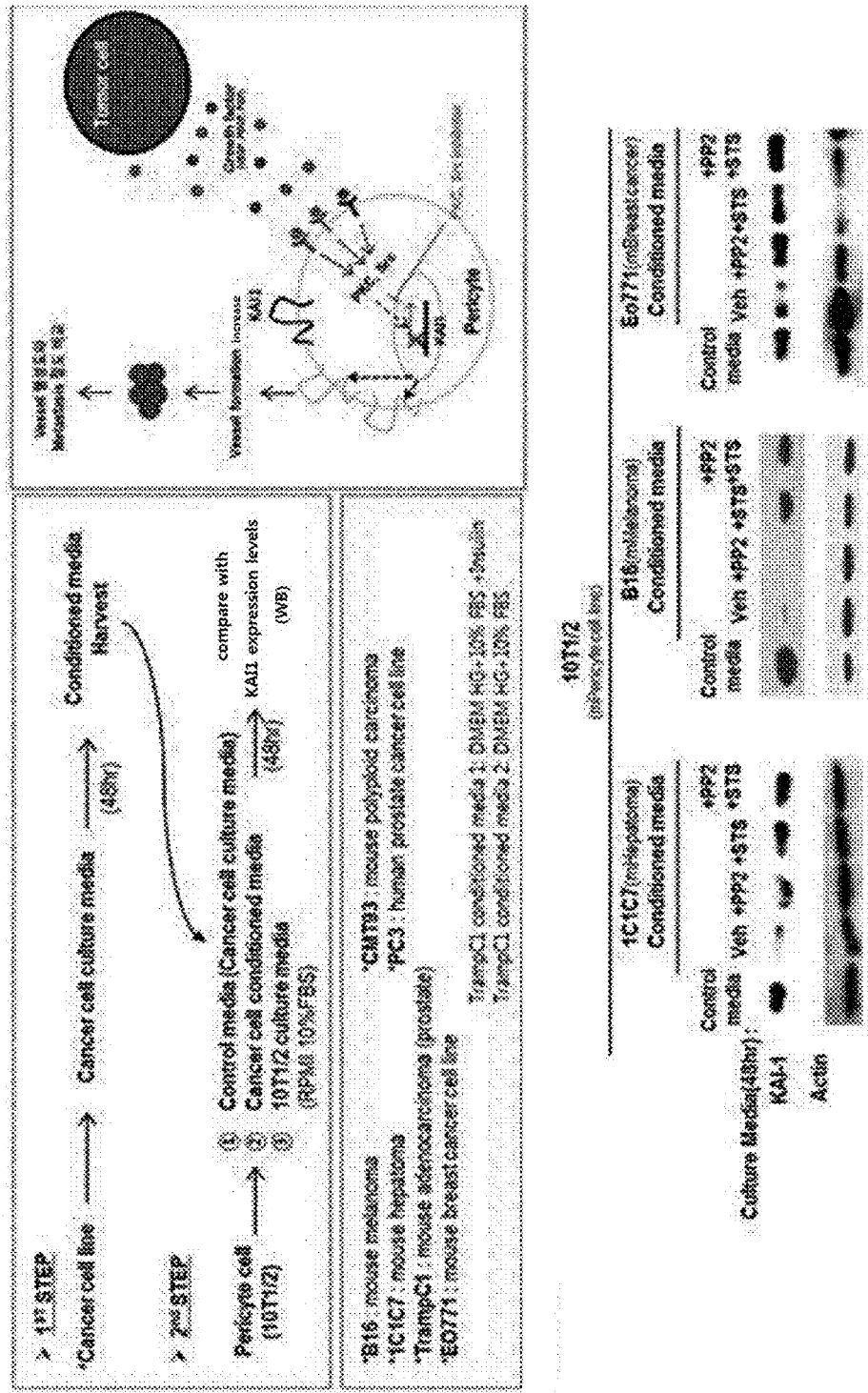
FIG. 52 shows the result of examining KAI1 expression when 10T1/2 and WT mVSMC were cultured with supernatants respectively obtained from cultures of a mouse melanoma cell line B16, a hepatoma cell line Hepa-1c1c7, and a breast cancer cell line EO771, and the result of comparing with a control.

Subsequently, when 10T1/2 and WT mVSMC were cultured with supernatants obtained by culturing a mouse melanoma cell line B16, a hepatoma cell line Hepa-1c1c7, and a breast cancer cell line EO771, KAI1 expression was confirmed, whereas in the control, it was not. As a result, as shown in FIG. 52, it can be confirmed that the KAI1 expression was lower than in the control.

Figure 53:
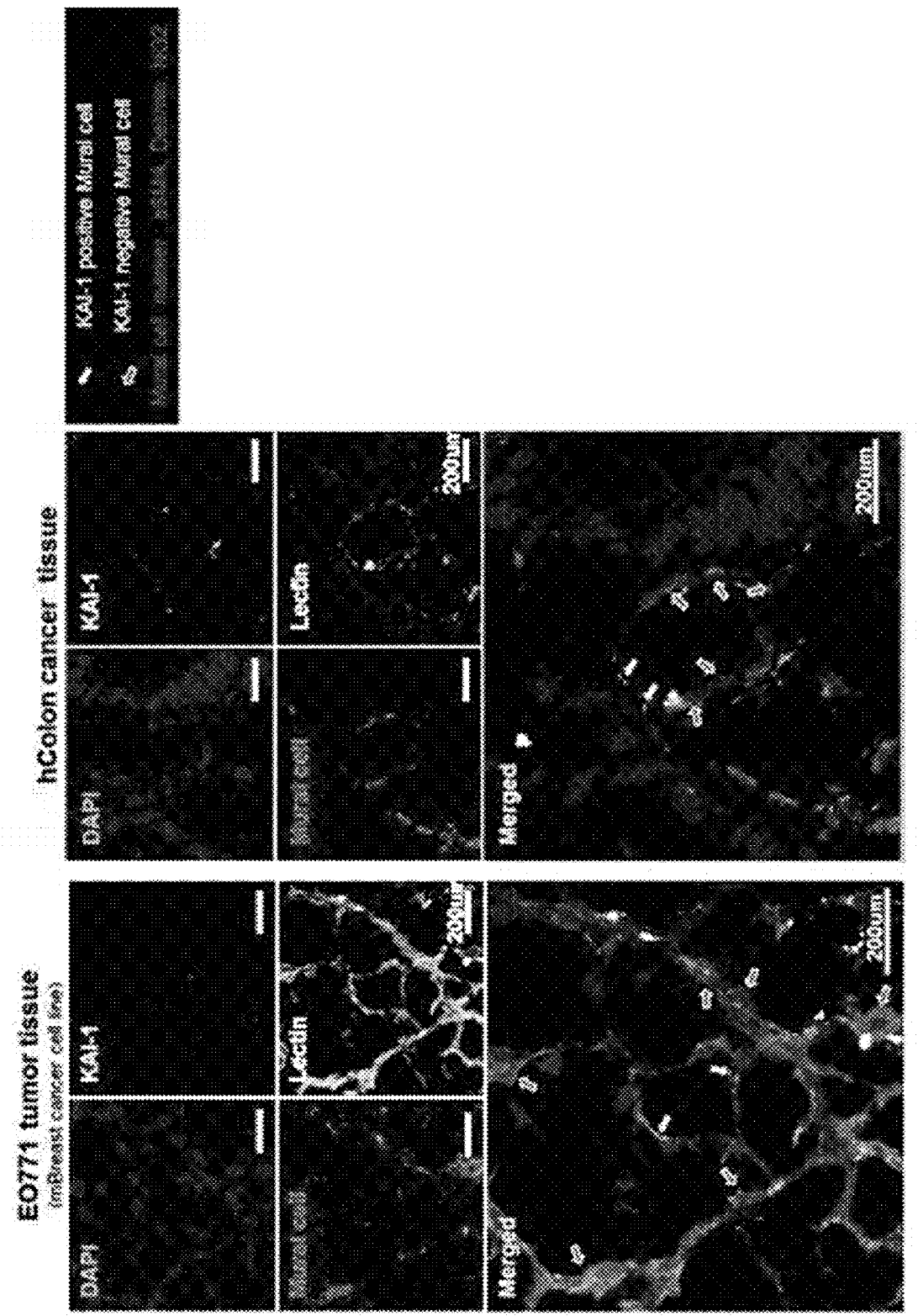
FIG. 53 shows the result of observing tumor tissues prepared by injecting Hepa-1C1C7 and EO771 into mice to form a tumor and immunostained with lectin (white), a mural cell marker (aSMA+NG2+Desmin, red), and KAI1 (green).

Afterwards, tumors were created by adding Hepa-1C1C7 and EO771 to mice, and their tissues were immunostained with lectin (white), mural cell marker (aSMA+NG2+ Desmin, red), and KAI1 (green) and then observed. As a result, as shown in FIG. 53, it can be confirmed that KAI1 expression was inhibited in most pericytes wrapping around vessels of the tumor tissue.

Then, based on the experiment, an experiment using animal subjects was carried out. A C57 mouse was treated with a tumor cell line or a combination of inhibitors of Src and Pkc, which signal to block KAI1 expression via VEGF, FGF, and PDGFb. As a result, it can be confirmed that tumor growth and vasculogenesis around tumor tissue were more inhibited in the group treated with the Src and Pkc inhibitors than in the tumor cell line-treated group. In addition, immunostaining was used to confirm that such a result was caused by KAI1 expression of pericytes. Such a result also occurred in a group treated with LIF secreted from pericytes expressing rhKAI1 and KAI1.

Figure 54:
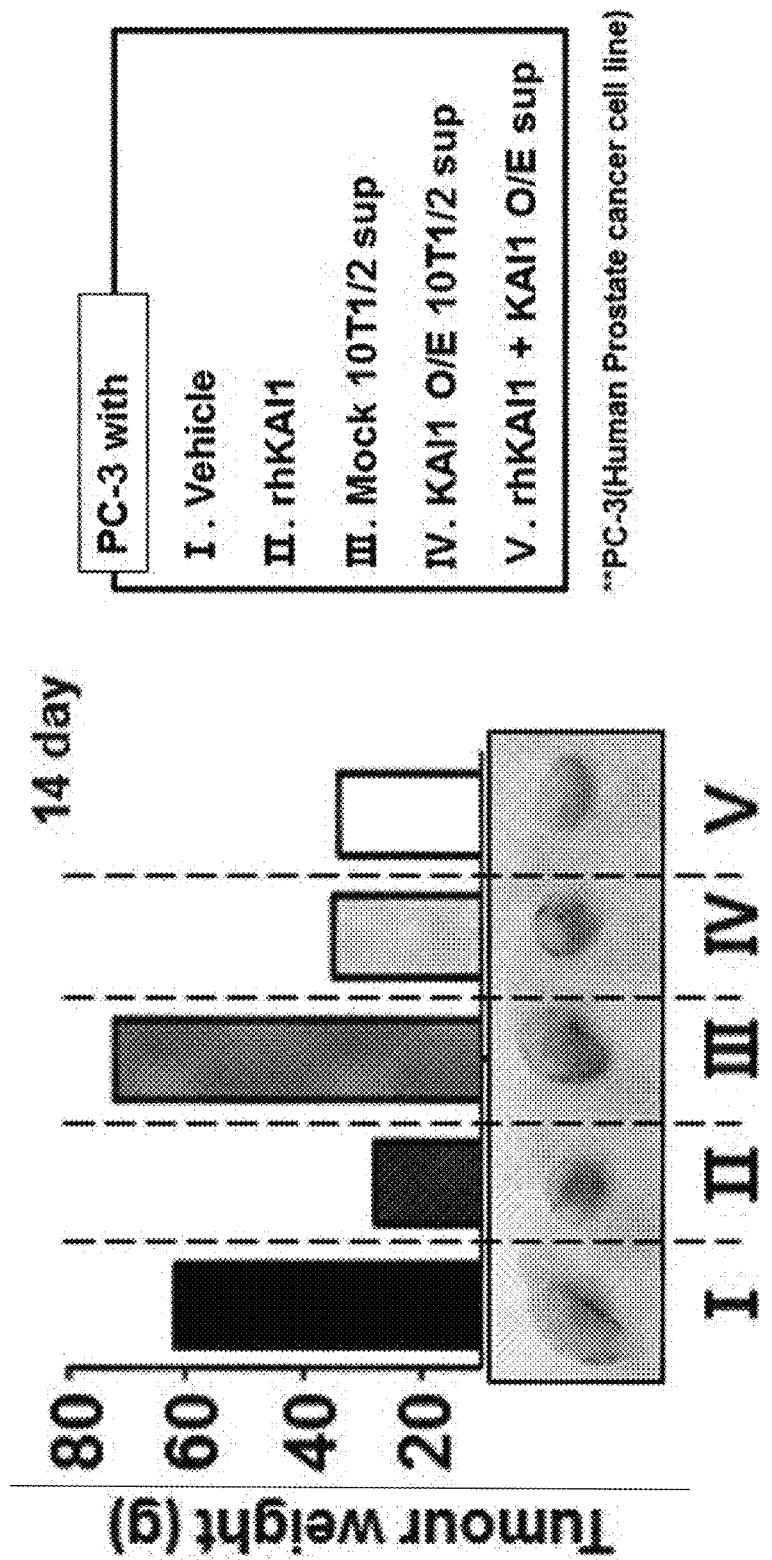
FIGS. 54 and 55 show the comparison of each experimental group after a prostate cancer cell line (PC-3) is mixed with a matrigel and injected into the S and C of a mouse to observe tumor mass formation to confirm whether a recombinant KAI1 protein can exhibit an anticancer effect.
Figure 55:
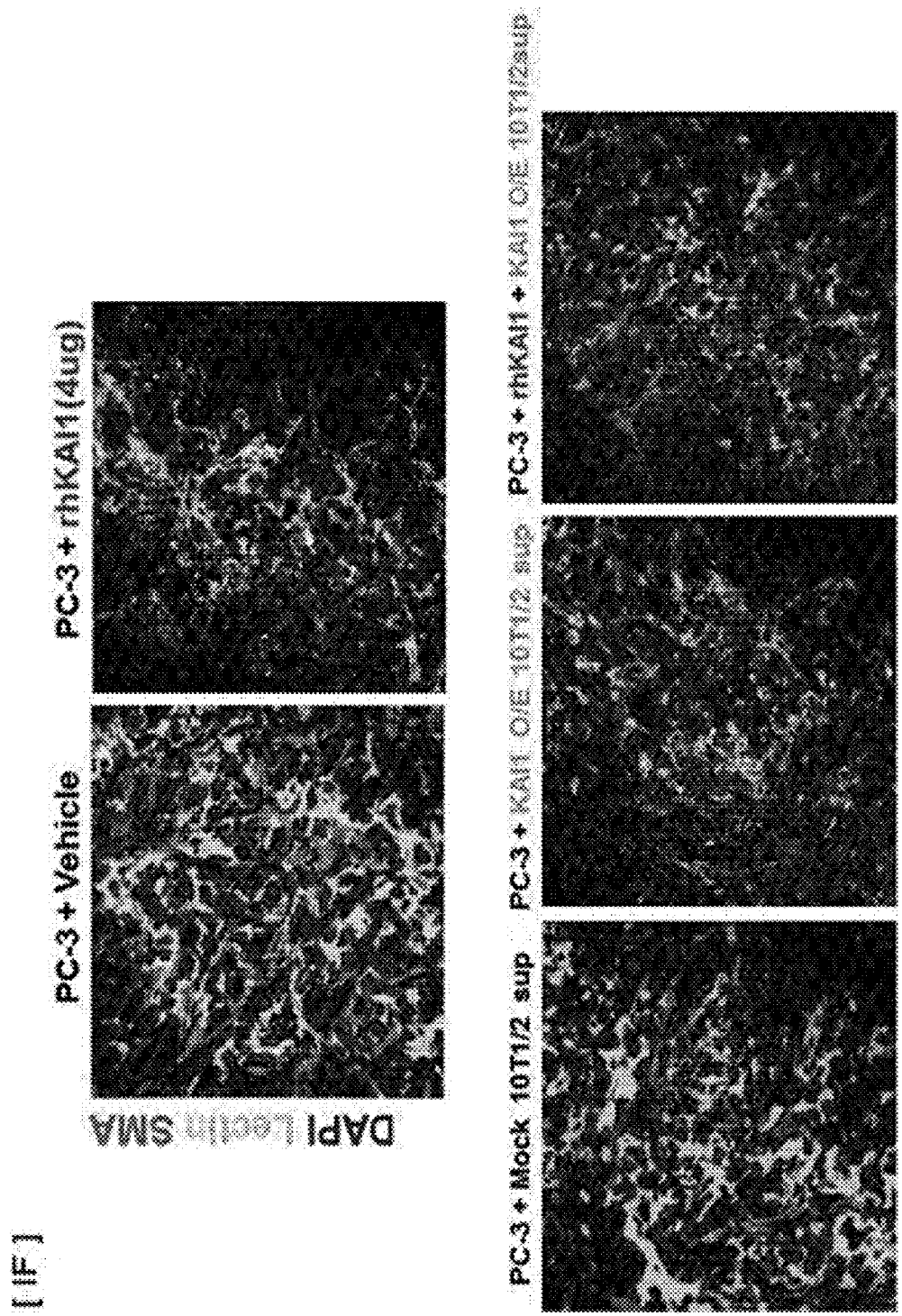

After that, an experiment using animal subjects was carried out to confirm whether a recombinant KAI1 protein exhibited an anticancer effect. More specifically, a prostate cancer cell line (PC-3) was mixed with a matrigel and subcutaneously injected into mice, and then tumor mass formation was observed and compared per experimental group. As a result, as shown in FIGS. 54 and 55, it can be confirmed that, compared to a vehicle, tumor mass was smaller in a group injected with a recombinant KAI1 protein. In addition, it can be confirmed that tumor mass was smaller in a group injected with a supernatant of KAI1 O/E 10T1/2 than in a group injected with a supernatant of mock 10T1/2. After the tumor mass obtained in the above-mentioned experiment was fixed with PFA, the cross-section was formed into sections, and a degree of angiogenesis per experimental group was determined by IF. Antibodies used herein were BS-1 Lectin (EC marker, 488 fluorescence), α-SMA (Pericyte marker, 555 fluorescence), and DAPI (nucleus marker, 405 fluorescence).

Example 12. Confirmation of Retinal Disease Treating Effect of KAI1-Expressed Pericytes Retinal diseases such as diabetic retinopathy and central serous (chorio)retinopathy are diseases of the loss of eyesight as vessel permeability is increased by a VEGF, body fluids gather around the retina (macular edema), and pathological angiogenesis occur.

A KAI1 protein was injected into the orbit of a model mouse with such a disease, and a degree of angiogenesis inhibition was compared with a control (not treated). As a result, when the KAI1 protein was injected, the inhibition of angiogenesis in the presence of VEGF was able to be confirmed through immunofluorescence using retinal endothelial cells and a pericyte-specific marker, whereas it was not confirmed in the control.

Example 13. Comparison of Effect of KAI1 Expressions in ECs and Pericytes on Regulation of Vessel Formation To compare and observe the effect of KAI1 expression of ECs and that of pericytes on angiogenesis, an experiment was carried out as follows.

Figure 56:
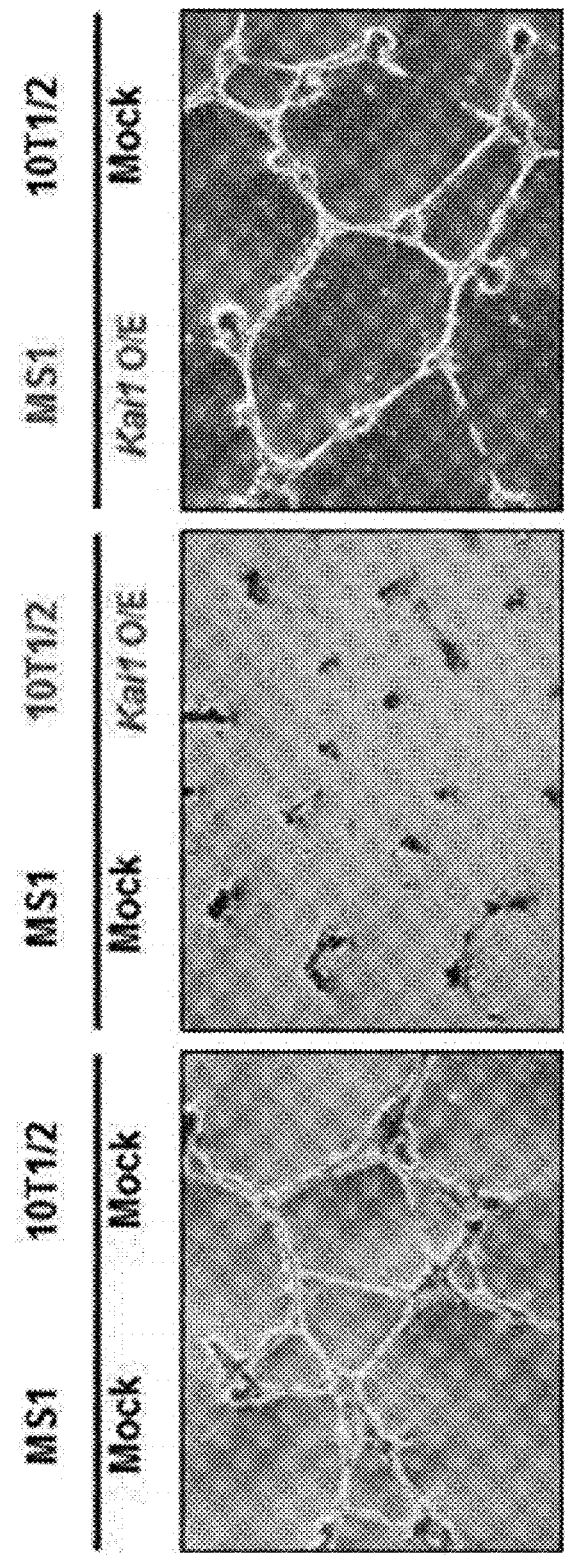
FIG. 56 shows the result of co-tube formation performed on a matrigel after overexpression is induced in both an EC and a pericyte using KAI1 adenovirus to compare an effect of KAI1 expression of EC on angiogenesis with that of the pericyte.

That is, overexpression was induced in ECs and pericytes using a KAI1 adenovirus, and co-tube formation was performed on a matrigel. Culture media used herein were DMEM supplemented with 10% FBS and 1× Antibiotics-antimycotics. As a result, as shown in FIG. 56, it was confirmed that in a group in which co-tube formation of mock adenovirus-transduced ECs and KAI1-overexpressed pericytes occurred, tube formation was more inhibited than in a group in which co-tube formation of KAI1-overexpressed ECs and mock adenovirus-transduced pericytes occurred. From the result, it can be seen that KAI1 expression of pericytes, rather than KAI1 expression of ECs, was a critical factor in inhibiting vasculogenesis.

It would be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

The invention claimed is:

1. A method of treating a cancer comprising administering a composition comprising an effective amount of a KAI1 (Kang AI 1) polypeptide consisting of the amino acid sequence as set forth in SEQ ID NO: 1 or 2 to a subject in need thereof, wherein the cancer is selected from the group consisting of colon cancer, pancreatic cancer, colorectal cancer, prostate cancer, kidney cancer, melanoma, bone metastasis of prostate cancer, ovarian cancer, and blood cancer.

2. The method of claim 1, wherein the composition further comprising a DARC (Duffy Antigen Receptor for Chemokines) polypeptide.

3. The method of claim 2, wherein the DARC polypeptide consists of the amino acid sequence of SEQ ID NO: 3 or 4.

4. The method of claim 1, wherein the KAI1 polypeptide is expressed in pericytes to inhibit angiogenesis.

5. The method of claim 4, wherein the pericytes improve organ transplantation or regeneration ability.

* * * * *

SEQUENCE LISTING

```
<160> NUMBER OF SEQ ID NOS: 68

<210> SEQ ID NO 1
<211> LENGTH: 267
<212> TYPE: PRT
<213> ORGANISM: Homo sapiens

<400> SEQUENCE: 1

Met Gly Ser Ala Cys Ile Lys Val Thr Lys Tyr Phe Leu Phe Leu Phe
1               5                   10                  15

Asn Leu Ile Phe Phe Ile Leu Gly Ala Val Ile Leu Gly Phe Gly Val
            20                  25                  30

Trp Ile Leu Ala Asp Lys Ser Ser Phe Ile Ser Val Leu Gln Thr Ser
        35                  40                  45

Ser Ser Ser Leu Arg Met Gly Ala Tyr Val Phe Ile Gly Val Gly Ala
    50                  55                  60

Val Thr Met Leu Met Gly Phe Leu Gly Cys Ile Gly Ala Val Asn Glu
65                  70                  75                  80

Val Arg Cys Leu Leu Gly Leu Tyr Phe Ala Phe Leu Leu Leu Ile Leu
                85                  90                  95

Ile Ala Gln Val Thr Ala Gly Ala Leu Phe Tyr Phe Asn Met Gly Lys
            100                 105                 110

Leu Lys Gln Glu Met Gly Gly Ile Val Thr Glu Leu Ile Arg Asp Tyr
        115                 120                 125
```

```
Asn Ser Ser Arg Glu Asp Ser Leu Gln Asp Ala Trp Asp Tyr Val Gln
    130                 135                 140

Ala Gln Val Lys Cys Cys Gly Trp Val Ser Phe Tyr Asn Trp Thr Asp
145                 150                 155                 160

Asn Ala Glu Leu Met Asn Arg Pro Glu Val Thr Tyr Pro Cys Ser Cys
                165                 170                 175

Glu Val Lys Gly Glu Asp Asn Ser Leu Ser Val Arg Lys Gly Phe
            180                 185                 190

Cys Glu Ala Pro Gly Asn Arg Thr Gln Ser Gly Asn His Pro Glu Asp
            195                 200                 205

Trp Pro Val Tyr Gln Glu Gly Cys Met Glu Lys Val Gln Ala Trp Leu
    210                 215                 220

Gln Glu Asn Leu Gly Ile Ile Leu Gly Val Gly Val Gly Val Ala Ile
225                 230                 235                 240

Val Glu Leu Leu Gly Met Val Leu Ser Ile Cys Leu Cys Arg His Val
                245                 250                 255

His Ser Glu Asp Tyr Ser Lys Val Pro Lys Tyr
            260                 265

<210> SEQ ID NO 2
<211> LENGTH: 266
<212> TYPE: PRT
<213> ORGANISM: Mus musculus

<400> SEQUENCE: 2

Met Gly Ala Gly Cys Val Lys Val Thr Lys Tyr Phe Leu Phe Leu Phe
1               5                   10                  15

Asn Leu Leu Phe Phe Ile Leu Gly Ala Val Ile Leu Gly Phe Gly Val
                20                  25                  30

Trp Ile Leu Ala Asp Lys Asn Ser Phe Ile Ser Val Leu Gln Thr Ser
            35                  40                  45

Ser Ser Ser Leu Gln Val Gly Ala Tyr Val Phe Ile Gly Val Gly Ala
        50                  55                  60

Ile Thr Ile Val Met Gly Phe Leu Gly Cys Ile Gly Ala Val Asn Glu
65                  70                  75                  80

Val Arg Cys Leu Leu Gly Leu Tyr Phe Val Phe Leu Leu Leu Ile Leu
                85                  90                  95

Ile Ala Gln Val Thr Val Gly Val Leu Phe Tyr Phe Asn Ala Asp Lys
            100                 105                 110

Leu Lys Lys Glu Met Gly Asn Thr Val Met Asp Ile Ile Arg Asn Tyr
        115                 120                 125

Thr Ala Asn Ala Thr Ser Ser Arg Glu Glu Ala Trp Asp Tyr Val Gln
130                 135                 140

Ala Gln Val Lys Cys Cys Gly Trp Val Ser His Tyr Asn Trp Thr Glu
145                 150                 155                 160

Asn Glu Glu Leu Met Gly Phe Thr Lys Thr Thr Tyr Pro Cys Ser Cys
                165                 170                 175

Glu Lys Ile Lys Glu Glu Asp Asn Gln Leu Ile Val Lys Lys Gly Phe
            180                 185                 190

Cys Glu Ala Asp Asn Ser Thr Val Ser Glu Asn Pro Glu Asp Trp
        195                 200                 205

Pro Val Asn Thr Glu Gly Cys Met Glu Lys Ala Gln Ala Trp Leu Gln
    210                 215                 220

Glu Asn Phe Gly Ile Leu Leu Gly Val Cys Ala Gly Val Ala Val Ile
225                 230                 235                 240
```

Glu Leu Leu Gly Leu Phe Leu Ser Ile Cys Leu Cys Arg Tyr Ile His
            245                 250                 255

Ser Glu Asp Tyr Ser Lys Val Pro Lys Tyr
            260                 265

<210> SEQ ID NO 3
<211> LENGTH: 338
<212> TYPE: PRT
<213> ORGANISM: Homo sapiens

<400> SEQUENCE: 3

Met Ala Ser Ser Gly Tyr Val Leu Gln Ala Glu Leu Ser Pro Ser Thr
 1               5                  10                  15

Glu Asn Ser Ser Gln Leu Asp Phe Glu Asp Val Trp Asn Ser Ser Tyr
                20                  25                  30

Gly Val Asn Asp Ser Phe Pro Asp Gly Asp Tyr Gly Ala Asn Leu Glu
            35                  40                  45

Ala Ala Ala Pro Cys His Ser Cys Asn Leu Leu Asp Asp Ser Ala Leu
        50                  55                  60

Pro Phe Phe Ile Leu Thr Ser Val Leu Gly Ile Leu Ala Ser Ser Thr
65                  70                  75                  80

Val Leu Phe Met Leu Phe Arg Pro Leu Phe Arg Trp Gln Leu Cys Pro
                85                  90                  95

Gly Trp Pro Val Leu Ala Gln Leu Ala Val Gly Ser Ala Leu Phe Ser
            100                 105                 110

Ile Val Val Pro Val Leu Ala Pro Gly Leu Gly Ser Thr Arg Ser Ser
            115                 120                 125

Ala Leu Cys Ser Leu Gly Tyr Cys Val Trp Tyr Gly Ser Ala Phe Ala
        130                 135                 140

Gln Ala Leu Leu Leu Gly Cys His Ala Ser Leu Gly His Arg Leu Gly
145                 150                 155                 160

Ala Gly Gln Val Pro Gly Leu Thr Leu Gly Leu Thr Val Gly Ile Trp
                165                 170                 175

Gly Val Ala Ala Leu Leu Thr Leu Pro Val Thr Leu Ala Ser Gly Ala
            180                 185                 190

Ser Gly Gly Leu Cys Thr Leu Ile Tyr Ser Thr Glu Leu Lys Ala Leu
        195                 200                 205

Gln Ala Thr His Thr Val Ala Cys Leu Ala Ile Phe Val Leu Leu Pro
210                 215                 220

Leu Gly Leu Phe Gly Ala Lys Gly Leu Lys Lys Ala Leu Gly Met Gly
225                 230                 235                 240

Pro Gly Pro Trp Met Asn Ile Leu Trp Ala Trp Phe Ile Phe Trp Trp
                245                 250                 255

Pro His Gly Val Val Leu Gly Leu Asp Phe Leu Val Arg Ser Lys Leu
            260                 265                 270

Leu Leu Leu Ser Thr Cys Leu Ala Gln Gln Ala Leu Asp Leu Leu Leu
        275                 280                 285

Asn Leu Ala Glu Ala Leu Ala Ile Leu His Cys Val Ala Thr Pro Leu
    290                 295                 300

Leu Leu Ala Leu Phe Cys His Gln Ala Thr Arg Thr Leu Leu Pro Ser
305                 310                 315                 320

Leu Pro Leu Pro Glu Gly Trp Ser Ser His Leu Asp Thr Leu Gly Ser
                325                 330                 335

Lys Ser

<210> SEQ ID NO 4
<211> LENGTH: 334
<212> TYPE: PRT
<213> ORGANISM: Mus musculus

<400> SEQUENCE: 4

Met Gly Asn Cys Leu Tyr Pro Val Glu Asn Leu Ser Leu Asp Lys Asn
1               5                   10                  15

Gly Thr Gln Phe Thr Phe Asp Ser Trp Asn Tyr Ser Phe Glu Asp Asn
            20                  25                  30

Tyr Ser Tyr Glu Leu Ser Ser Asp Tyr Ser Leu Thr Pro Ala Ala Pro
        35                  40                  45

Cys Tyr Ser Cys Asn Leu Leu Gly Arg Ser Ser Leu Pro Phe Phe Met
    50                  55                  60

Leu Thr Ser Val Leu Gly Met Leu Ala Ser Gly Gly Ile Leu Phe Ala
65                  70                  75                  80

Ile Leu Arg Pro Phe Phe His Trp Gln Ile Cys Pro Ser Trp Pro Ile
                85                  90                  95

Leu Ala Glu Leu Ala Val Gly Ser Ala Leu Phe Ser Ile Ala Val Pro
            100                 105                 110

Ile Leu Ala Pro Gly Leu His Ser Ala His Ser Thr Ala Leu Cys Asn
        115                 120                 125

Leu Gly Tyr Trp Val Trp Tyr Thr Ser Ala Phe Ala Gln Ala Leu Leu
    130                 135                 140

Ile Gly Cys Tyr Ala Cys Leu Asn Pro Arg Leu Asn Ile Gly Gln Leu
145                 150                 155                 160

Arg Gly Phe Thr Leu Gly Leu Ser Val Gly Leu Trp Gly Ala Ala Ala
                165                 170                 175

Leu Leu Gly Leu Pro Val Ala Leu Ala Ser Asp Ala Tyr Asn Gly Phe
            180                 185                 190

Cys Ala Phe Pro Ser Ser Arg Asp Met Glu Ala Leu Lys Tyr Met His
        195                 200                 205

Tyr Ala Ile Cys Phe Thr Ile Phe Thr Val Leu Pro Pro Thr Leu Leu
    210                 215                 220

Ala Ala Lys Gly Leu Lys Ile Ala Leu Ser Lys Gly Pro Gly Pro Trp
225                 230                 235                 240

Val Ser Val Leu Trp Ile Trp Phe Ile Phe Trp Trp Pro His Gly Met
                245                 250                 255

Val Leu Ile Phe Asp Ala Leu Val Arg Ser Lys Ile Val Leu Leu Tyr
            260                 265                 270

Thr Cys Gln Ser Gln Lys Ile Leu Asp Ala Met Leu Asn Val Thr Glu
        275                 280                 285

Ala Leu Ser Met Leu His Cys Val Ala Thr Pro Leu Leu Leu Ala Leu
    290                 295                 300

Phe Cys His Gln Thr Thr Arg Arg Ser Leu Ser Ser Leu Ser Leu Pro
305                 310                 315                 320

Thr Arg Gln Ala Ser Gln Met Asp Ala Leu Ala Gly Lys Ser
                325                 330

<210> SEQ ID NO 5
<211> LENGTH: 22
<212> TYPE: DNA
<213> ORGANISM: Artificial Sequence
<220> FEATURE:
<223> OTHER INFORMATION: KAI1 forward primer

```
<400> SEQUENCE: 5
cagccactac aactggacag ag                                              22

<210> SEQ ID NO 6
<211> LENGTH: 22
<212> TYPE: DNA
<213> ORGANISM: Artificial Sequence
<220> FEATURE:
<223> OTHER INFORMATION: KAI1 reverse primer

<400> SEQUENCE: 6
tacttgggga ccttgctgta gt                                              22

<210> SEQ ID NO 7
<211> LENGTH: 20
<212> TYPE: DNA
<213> ORGANISM: Artificial Sequence
<220> FEATURE:
<223> OTHER INFORMATION: alpha SMA forward primer

<400> SEQUENCE: 7
ctgacagagg caccactgaa                                                 20

<210> SEQ ID NO 8
<211> LENGTH: 21
<212> TYPE: DNA
<213> ORGANISM: Artificial Sequence
<220> FEATURE:
<223> OTHER INFORMATION: alpha SMA reverse primer

<400> SEQUENCE: 8
atctcacgct cggcagtagt a                                               21

<210> SEQ ID NO 9
<211> LENGTH: 20
<212> TYPE: DNA
<213> ORGANISM: Artificial Sequence
<220> FEATURE:
<223> OTHER INFORMATION: Desmin forward primer

<400> SEQUENCE: 9
tgcagccact ctagctcgta                                                 20

<210> SEQ ID NO 10
<211> LENGTH: 20
<212> TYPE: DNA
<213> ORGANISM: Artificial Sequence
<220> FEATURE:
<223> OTHER INFORMATION: Desmin reverse primer

<400> SEQUENCE: 10
ctcatcaggg agtcgttggt                                                 20

<210> SEQ ID NO 11
<211> LENGTH: 20
<212> TYPE: DNA
<213> ORGANISM: Artificial Sequence
<220> FEATURE:
<223> OTHER INFORMATION: CD31 forward primer

<400> SEQUENCE: 11
gaatgacacc caagcgtttt                                                 20

<210> SEQ ID NO 12
```

```
<211> LENGTH: 20
<212> TYPE: DNA
<213> ORGANISM: Artificial Sequence
<220> FEATURE:
<223> OTHER INFORMATION: CD31 reverse primer

<400> SEQUENCE: 12
ggcttccaca ctaggctcag                                              20

<210> SEQ ID NO 13
<211> LENGTH: 20
<212> TYPE: DNA
<213> ORGANISM: Artificial Sequence
<220> FEATURE:
<223> OTHER INFORMATION: VE-CAD forward primer

<400> SEQUENCE: 13
attgagacag accccaaacg                                              20

<210> SEQ ID NO 14
<211> LENGTH: 20
<212> TYPE: DNA
<213> ORGANISM: Artificial Sequence
<220> FEATURE:
<223> OTHER INFORMATION: VE-CAD reverse primer

<400> SEQUENCE: 14
attcggaaga attggcctct                                              20

<210> SEQ ID NO 15
<211> LENGTH: 23
<212> TYPE: DNA
<213> ORGANISM: Artificial Sequence
<220> FEATURE:
<223> OTHER INFORMATION: GAPDH forward primer type I

<400> SEQUENCE: 15
cccttcattg acctcaacta cat                                          23

<210> SEQ ID NO 16
<211> LENGTH: 23
<212> TYPE: DNA
<213> ORGANISM: Artificial Sequence
<220> FEATURE:
<223> OTHER INFORMATION: GAPDH reverse primer type I

<400> SEQUENCE: 16
cattgctgac aatcttgagt gag                                          23

<210> SEQ ID NO 17
<211> LENGTH: 21
<212> TYPE: DNA
<213> ORGANISM: Artificial Sequence
<220> FEATURE:
<223> OTHER INFORMATION: Ang2 forward primer

<400> SEQUENCE: 17
gaaggactgg gaaggcaacg a                                            21

<210> SEQ ID NO 18
<211> LENGTH: 21
<212> TYPE: DNA
<213> ORGANISM: Artificial Sequence
<220> FEATURE:
<223> OTHER INFORMATION: Ang2 reverse primer

<400> SEQUENCE: 18
```
ccaccagcct cctgagagca t                                            21

<210> SEQ ID NO 19
<211> LENGTH: 23
<212> TYPE: DNA
<213> ORGANISM: Artificial Sequence
<220> FEATURE:
<223> OTHER INFORMATION: PDGFb forward primer

<400> SEQUENCE: 19
acagggaagt ggactccgat act                                          23

<210> SEQ ID NO 20
<211> LENGTH: 21
<212> TYPE: DNA
<213> ORGANISM: Artificial Sequence
<220> FEATURE:
<223> OTHER INFORMATION: PDGFb reverse primer

<400> SEQUENCE: 20
acatccgtgt cctgttcccg a                                            21

<210> SEQ ID NO 21
<211> LENGTH: 22
<212> TYPE: DNA
<213> ORGANISM: Artificial Sequence
<220> FEATURE:
<223> OTHER INFORMATION: Apelin forward primer

<400> SEQUENCE: 21
cgagttgcag catgaatctg ag                                           22

<210> SEQ ID NO 22
<211> LENGTH: 22
<212> TYPE: DNA
<213> ORGANISM: Artificial Sequence
<220> FEATURE:
<223> OTHER INFORMATION: Apelin reverse primer

<400> SEQUENCE: 22
tgttccatct ggaggcaaca tc                                           22

<210> SEQ ID NO 23
<211> LENGTH: 23
<212> TYPE: DNA
<213> ORGANISM: Artificial Sequence
<220> FEATURE:
<223> OTHER INFORMATION: Unc5b forward primer

<400> SEQUENCE: 23
gagtggctat gcttgtgatt tgg                                          23

<210> SEQ ID NO 24
<211> LENGTH: 22
<212> TYPE: DNA
<213> ORGANISM: Artificial Sequence
<220> FEATURE:
<223> OTHER INFORMATION: Unc5b reverse primer

<400> SEQUENCE: 24
catagcaaag cctttccctg tg                                           22

<210> SEQ ID NO 25
<211> LENGTH: 20
<212> TYPE: DNA

```
<213> ORGANISM: Artificial Sequence
<220> FEATURE:
<223> OTHER INFORMATION: Dll4 forward primer

<400> SEQUENCE: 25
aggtgccact tcggttacac                                              20

<210> SEQ ID NO 26
<211> LENGTH: 20
<212> TYPE: DNA
<213> ORGANISM: Artificial Sequence
<220> FEATURE:
<223> OTHER INFORMATION: Dll4 reverse primer

<400> SEQUENCE: 26
gggagagcaa atggctgata                                              20

<210> SEQ ID NO 27
<211> LENGTH: 20
<212> TYPE: DNA
<213> ORGANISM: Artificial Sequence
<220> FEATURE:
<223> OTHER INFORMATION: VEGFR3 forward primer

<400> SEQUENCE: 27
tggtaccggc tcaacctctc                                              20

<210> SEQ ID NO 28
<211> LENGTH: 20
<212> TYPE: DNA
<213> ORGANISM: Artificial Sequence
<220> FEATURE:
<223> OTHER INFORMATION: VEGFR3 reverse primer

<400> SEQUENCE: 28
cacgtttttg cagtccagca                                              20

<210> SEQ ID NO 29
<211> LENGTH: 25
<212> TYPE: DNA
<213> ORGANISM: Artificial Sequence
<220> FEATURE:
<223> OTHER INFORMATION: VEGFR1 forward primer

<400> SEQUENCE: 29
gaggaggatg agggtgtcta taggt                                        25

<210> SEQ ID NO 30
<211> LENGTH: 23
<212> TYPE: DNA
<213> ORGANISM: Artificial Sequence
<220> FEATURE:
<223> OTHER INFORMATION: VEGFR1 reverse primer

<400> SEQUENCE: 30
gtgatcagct ccaggtttga ctt                                          23

<210> SEQ ID NO 31
<211> LENGTH: 20
<212> TYPE: DNA
<213> ORGANISM: Artificial Sequence
<220> FEATURE:
<223> OTHER INFORMATION: Jag1 forward primer

<400> SEQUENCE: 31
gaggcgtcct ctgaaaaaca                                              20
```

```
<210> SEQ ID NO 32
<211> LENGTH: 21
<212> TYPE: DNA
<213> ORGANISM: Artificial Sequence
<220> FEATURE:
<223> OTHER INFORMATION: Jag1 reverse primer

<400> SEQUENCE: 32
acccaagcca ctgttaagac a                                              21

<210> SEQ ID NO 33
<211> LENGTH: 19
<212> TYPE: DNA
<213> ORGANISM: Artificial Sequence
<220> FEATURE:
<223> OTHER INFORMATION: GAPDH forward primer type II

<400> SEQUENCE: 33
tgtccgtcgt ggatctgac                                                 19

<210> SEQ ID NO 34
<211> LENGTH: 20
<212> TYPE: DNA
<213> ORGANISM: Artificial Sequence
<220> FEATURE:
<223> OTHER INFORMATION: GAPDH reverse primer type II

<400> SEQUENCE: 34
cctgcttcac caccttcttg                                                20

<210> SEQ ID NO 35
<211> LENGTH: 20
<212> TYPE: DNA
<213> ORGANISM: Artificial Sequence
<220> FEATURE:
<223> OTHER INFORMATION: SOX17 forward primer

<400> SEQUENCE: 35
cagcaagatg ctgggaaagt                                                20

<210> SEQ ID NO 36
<211> LENGTH: 20
<212> TYPE: DNA
<213> ORGANISM: Artificial Sequence
<220> FEATURE:
<223> OTHER INFORMATION: SOX17 reverse primer

<400> SEQUENCE: 36
gttggggtag tcctgcatgt                                                20

<210> SEQ ID NO 37
<211> LENGTH: 22
<212> TYPE: DNA
<213> ORGANISM: Artificial Sequence
<220> FEATURE:
<223> OTHER INFORMATION: VEGFR2 forward primer

<400> SEQUENCE: 37
atcggagaag aacgtggtta aa                                             22

<210> SEQ ID NO 38
<211> LENGTH: 22
<212> TYPE: DNA
<213> ORGANISM: Artificial Sequence
<220> FEATURE:
```

<223> OTHER INFORMATION: VEGFR2 reverse primer

<400> SEQUENCE: 38
caaatgttcc accaactctg aa                                               22

<210> SEQ ID NO 39
<211> LENGTH: 20
<212> TYPE: DNA
<213> ORGANISM: Artificial Sequence
<220> FEATURE:
<223> OTHER INFORMATION: OPTC forward primer

<400> SEQUENCE: 39 tgaggggtg tctagctgtc                                                   20

<210> SEQ ID NO 40
<211> LENGTH: 20
<212> TYPE: DNA
<213> ORGANISM: Artificial Sequence
<220> FEATURE:
<223> OTHER INFORMATION: OPTC reverse primer

<400> SEQUENCE: 40
tctgagggag gggtaggagt                                                  20

<210> SEQ ID NO 41
<211> LENGTH: 20
<212> TYPE: DNA
<213> ORGANISM: Artificial Sequence
<220> FEATURE:
<223> OTHER INFORMATION: PF4 forward primer

<400> SEQUENCE: 41
agtcctgagc tgctgcttct                                                  20

<210> SEQ ID NO 42
<211> LENGTH: 20
<212> TYPE: DNA
<213> ORGANISM: Artificial Sequence
<220> FEATURE:
<223> OTHER INFORMATION: PF4 reverse primer

<400> SEQUENCE: 42
ggcaaatttt cctcccattc                                                  20

<210> SEQ ID NO 43
<211> LENGTH: 20
<212> TYPE: DNA
<213> ORGANISM: Artificial Sequence
<220> FEATURE:
<223> OTHER INFORMATION: HOXA5 forward primer

<400> SEQUENCE: 43
aaaaactccc tgggcaactc                                                  20

<210> SEQ ID NO 44
<211> LENGTH: 20
<212> TYPE: DNA
<213> ORGANISM: Artificial Sequence
<220> FEATURE:
<223> OTHER INFORMATION: HOXA5 reverse primer

<400> SEQUENCE: 44
tgggccacct atattgtcgt                                                  20

-continued

<210> SEQ ID NO 45
<211> LENGTH: 20
<212> TYPE: DNA
<213> ORGANISM: Artificial Sequence
<220> FEATURE:
<223> OTHER INFORMATION: SULF1 forward primer

<400> SEQUENCE: 45
ccaaacgaca caatccactg                                              20

<210> SEQ ID NO 46
<211> LENGTH: 20
<212> TYPE: DNA
<213> ORGANISM: Artificial Sequence
<220> FEATURE:
<223> OTHER INFORMATION: SULF1 reverse primer

<400> SEQUENCE: 46
tgaaggggtg aaggtgactc                                              20

<210> SEQ ID NO 47
<211> LENGTH: 20
<212> TYPE: DNA
<213> ORGANISM: Artificial Sequence
<220> FEATURE:
<223> OTHER INFORMATION: Serpinf1 forward primer

<400> SEQUENCE: 47
actgcccctg agaagaacct                                              20

<210> SEQ ID NO 48
<211> LENGTH: 20
<212> TYPE: DNA
<213> ORGANISM: Artificial Sequence
<220> FEATURE:
<223> OTHER INFORMATION: Serpinf1 reverse primer

<400> SEQUENCE: 48
gcctgcaccc agttgttaat                                              20

<210> SEQ ID NO 49
<211> LENGTH: 22
<212> TYPE: DNA
<213> ORGANISM: Artificial Sequence
<220> FEATURE:
<223> OTHER INFORMATION: LIF forward primer

<400> SEQUENCE: 49
taccgcatag tcgtgtacct tg                                           22

<210> SEQ ID NO 50
<211> LENGTH: 21
<212> TYPE: DNA
<213> ORGANISM: Artificial Sequence
<220> FEATURE:
<223> OTHER INFORMATION: LIF reverse primer

<400> SEQUENCE: 50
actggggttg aggatcttct g                                            21

<210> SEQ ID NO 51
<211> LENGTH: 20
<212> TYPE: DNA
<213> ORGANISM: Artificial Sequence
<220> FEATURE:
<223> OTHER INFORMATION: CD59A forward primer

<400> SEQUENCE: 51
agccggaatg caagtgtatc                                               20

<210> SEQ ID NO 52
<211> LENGTH: 20
<212> TYPE: DNA
<213> ORGANISM: Artificial Sequence
<220> FEATURE:
<223> OTHER INFORMATION: CD59A reverse primer

<400> SEQUENCE: 52
atggtgtctt ccccaaggat                                               20

<210> SEQ ID NO 53
<211> LENGTH: 20
<212> TYPE: DNA
<213> ORGANISM: Artificial Sequence
<220> FEATURE:
<223> OTHER INFORMATION: CCL2 forward primer

<400> SEQUENCE: 53
caggtccctg tcatgcttct                                               20

<210> SEQ ID NO 54
<211> LENGTH: 20
<212> TYPE: DNA
<213> ORGANISM: Artificial Sequence
<220> FEATURE:
<223> OTHER INFORMATION: CCL2 reverse primer

<400> SEQUENCE: 54
tctggaccca ttccttcttg                                               20

<210> SEQ ID NO 55
<211> LENGTH: 20
<212> TYPE: DNA
<213> ORGANISM: Artificial Sequence
<220> FEATURE:
<223> OTHER INFORMATION: KLF4 forward primer

<400> SEQUENCE: 55
ccaaagaggg gaagaaggtc                                               20

<210> SEQ ID NO 56
<211> LENGTH: 20
<212> TYPE: DNA
<213> ORGANISM: Artificial Sequence
<220> FEATURE:
<223> OTHER INFORMATION: KLF4 reverse primer

<400> SEQUENCE: 56
cctgtgtgtt tgcggtagtg                                               20

<210> SEQ ID NO 57
<211> LENGTH: 20
<212> TYPE: DNA
<213> ORGANISM: Artificial Sequence
<220> FEATURE:
<223> OTHER INFORMATION: Anigotensin forward primer

<400> SEQUENCE: 57
ccagacaccc ctgctacagt                                               20

<210> SEQ ID NO 58
<211> LENGTH: 20

```
<212> TYPE: DNA
<213> ORGANISM: Artificial Sequence
<220> FEATURE:
<223> OTHER INFORMATION: Anigotensin reverse primer

<400> SEQUENCE: 58
tctgtactga ccccctccag                                              20

<210> SEQ ID NO 59
<211> LENGTH: 20
<212> TYPE: DNA
<213> ORGANISM: Artificial Sequence
<220> FEATURE:
<223> OTHER INFORMATION: ADAMTS1 forward primer

<400> SEQUENCE: 59
ggtcaccttg cagtgcctac                                              20

<210> SEQ ID NO 60
<211> LENGTH: 20
<212> TYPE: DNA
<213> ORGANISM: Artificial Sequence
<220> FEATURE:
<223> OTHER INFORMATION: ADAMTS1 reverse primer

<400> SEQUENCE: 60
ccagtgcacc acagggtagt                                              20

<210> SEQ ID NO 61
<211> LENGTH: 20
<212> TYPE: DNA
<213> ORGANISM: Artificial Sequence
<220> FEATURE:
<223> OTHER INFORMATION: ROCK2 forward primer

<400> SEQUENCE: 61
cagggaggta cgacttggaa                                              20

<210> SEQ ID NO 62
<211> LENGTH: 20
<212> TYPE: DNA
<213> ORGANISM: Artificial Sequence
<220> FEATURE:
<223> OTHER INFORMATION: ROCK2 reverse primer

<400> SEQUENCE: 62
tcgggaaggt ctctacatcg                                              20

<210> SEQ ID NO 63
<211> LENGTH: 20
<212> TYPE: DNA
<213> ORGANISM: Artificial Sequence
<220> FEATURE:
<223> OTHER INFORMATION: ROCK1 forward primer

<400> SEQUENCE: 63
cctgccctag agtgtcgaag                                              20

<210> SEQ ID NO 64
<211> LENGTH: 20
<212> TYPE: DNA
<213> ORGANISM: Artificial Sequence
<220> FEATURE:
<223> OTHER INFORMATION: ROCK1 reverse primer

<400> SEQUENCE: 64
```

-continued

```
tcttgttgac agcgttcgag                                              20

<210> SEQ ID NO 65
<211> LENGTH: 20
<212> TYPE: DNA
<213> ORGANISM: Artificial Sequence
<220> FEATURE:
<223> OTHER INFORMATION: Thrombospondin2 forward primer

<400> SEQUENCE: 65
gggtctgtgg acttcagtgg                                              20

<210> SEQ ID NO 66
<211> LENGTH: 20
<212> TYPE: DNA
<213> ORGANISM: Artificial Sequence
<220> FEATURE:
<223> OTHER INFORMATION: Thrombospondin2 reverse primer

<400> SEQUENCE: 66
gccagtacca gtcgtggagt                                              20

<210> SEQ ID NO 67
<211> LENGTH: 20
<212> TYPE: DNA
<213> ORGANISM: Artificial Sequence
<220> FEATURE:
<223> OTHER INFORMATION: STAT1 forward primer

<400> SEQUENCE: 67
cagctgagtt ccgacacctg                                              20

<210> SEQ ID NO 68
<211> LENGTH: 20
<212> TYPE: DNA
<213> ORGANISM: Artificial Sequence
<220> FEATURE:
<223> OTHER INFORMATION: STAT1 reverse primer

<400> SEQUENCE: 68
caccacgaca ggaagagagg                                              20
```